United States Patent
Wang et al.

(10) Patent No.: US 7,667,021 B2
(45) Date of Patent: Feb. 23, 2010

(54) NEUTRALIZING HUMAN ANTI-IGFR ANTIBODY

(75) Inventors: Yan Wang, Scotch Plains, NJ (US); Robert Greenberg, Sparta, NJ (US); Leonard Presta, San Francisco, CA (US); Jonathan A. Pachter, Setauket, NY (US); Judith Hailey, Edison, NJ (US); Peter Brams, Sacramento, CA (US); Denise Williams, San Jose, CA (US); Mohan Srinivasan, Cupertino, CA (US); Diane Feingersh, Union City, CA (US)

(73) Assignee: Schering Corporation, Kenilworth, NJ (US)

( * ) Notice: Subject to any disclaimer, the term of this patent is extended or adjusted under 35 U.S.C. 154(b) by 213 days.

(21) Appl. No.: 11/598,618

(22) Filed: Nov. 13, 2006

(65) Prior Publication Data

US 2007/0059305 A1    Mar. 15, 2007

Related U.S. Application Data

(62) Division of application No. 10/443,466, filed on May 22, 2003, now Pat. No. 7,217,796.

(60) Provisional application No. 60/383,459, filed on May 24, 2002, provisional application No. 60/393,214, filed on Jul. 2, 2002, provisional application No. 60/436,254, filed on Dec. 23, 2002.

(51) Int. Cl.
| C07H 21/04 | (2006.01) |
| C12P 21/04 | (2006.01) |
| C12N 15/00 | (2006.01) |
| C12N 5/06 | (2006.01) |
| A61K 39/395 | (2006.01) |
| C07K 16/00 | (2006.01) |
| C12P 21/08 | (2006.01) |

(52) U.S. Cl. .............. 536/23.53; 424/133.1; 424/141.1; 424/143.1; 424/155.1; 435/69.6; 435/70.21; 435/320.1; 435/328; 530/387.3; 530/388.1; 530/388.22; 530/388.8

(58) Field of Classification Search ....................... None
See application file for complete search history.

(56) References Cited

U.S. PATENT DOCUMENTS

| 4,543,439 A | 9/1985 | Frackelton, Jr. et al. |
| 4,604,463 A | 8/1986 | Miyasaka et al. |
| 4,659,516 A | 4/1987 | Bowler et al. |
| 5,198,340 A | 3/1993 | Mukku |
| 5,260,291 A | 11/1993 | Lunt et al. |
| 5,262,308 A | 11/1993 | Baserga |
| 5,362,718 A | 11/1994 | Skotnicki et al. |
| 5,719,148 A | 2/1998 | Bishop et al. |
| 5,942,412 A | 8/1999 | Prager et al. |
| 5,958,872 A | 9/1999 | O'Connor et al. |
| 5,977,307 A | 11/1999 | Friden et al. |
| 6,084,085 A | 7/2000 | Baserga et al. |
| 6,217,866 B1 | 4/2001 | Schlessinger et al. |
| 6,294,330 B1 | 9/2001 | Michnick et al. |
| 6,300,129 B1 | 10/2001 | Lonberg et al. |
| 6,316,462 B1 | 11/2001 | Bishop et al. |
| 6,333,031 B1 | 12/2001 | Olsson et al. |
| 6,346,390 B1 | 2/2002 | Olsson et al. |
| 6,372,250 B1 | 4/2002 | Pardridge |
| 6,403,569 B1 | 6/2002 | Achterrath |
| 6,537,988 B2 | 3/2003 | Lee |
| 6,645,775 B1 | 11/2003 | Clark et al. |
| 6,774,122 B2 | 8/2004 | Evans et al. |
| 6,794,370 B2 | 9/2004 | Achterrath |
| 6,884,879 B1 | 4/2005 | Baca et al. |
| 7,037,498 B2 | 5/2006 | Cohen et al. |
| 7,060,269 B1 | 6/2006 | Baca et al. |
| 7,169,901 B2 | 1/2007 | Baca et al. |
| 7,217,796 B2 | 5/2007 | Wang et al. |
| 7,235,576 B1 | 6/2007 | Riedl et al. |
| 7,297,334 B2 | 11/2007 | Baca et al. |
| 7,326,567 B2 | 2/2008 | Saha |
| 7,375,193 B2 | 5/2008 | Baca et al. |
| 2002/0022023 A1 | 2/2002 | Ullrich et al. |
| 2002/0025313 A1 | 2/2002 | Micklus et al. |
| 2002/0107187 A1 | 8/2002 | Kingston et al. |
| 2002/0132275 A1 | 9/2002 | Fidler et al. |
| 2002/0155095 A1 | 10/2002 | Nagabhushan et al. |
| 2002/0164333 A1 | 11/2002 | Nemerow et al. |
| 2002/0169116 A1 | 11/2002 | Kingston et al. |
| 2002/0187925 A1 | 12/2002 | Kingston et al. |
| 2002/0197262 A1 | 12/2002 | Hasan et al. |
| 2003/0021780 A1 | 1/2003 | Smith et al. |

(Continued)

FOREIGN PATENT DOCUMENTS

DE    197 19 001 C2    5/2001

(Continued)

OTHER PUBLICATIONS

Fundamental Immunology, 3rd Edition, William E. Paul, MD ed., pp. 292-295, 1993.*

(Continued)

Primary Examiner—David J. Blanchard

(57) ABSTRACT

The present invention includes isolated nucleic acids encoding fully human, neutralizing, monoclonal antibodies against human Insulin-like Growth Factor Receptor-I (IGFR1). Also included are methods of using and producing the antibodies of the invention.

46 Claims, No Drawings

U.S. PATENT DOCUMENTS

| | | |
|---|---|---|
| 2003/0031658 A1 | 2/2003 | Brodt et al. |
| 2003/0045676 A1 | 3/2003 | Kingston et al. |
| 2003/0087342 A1 | 5/2003 | Mermod et al. |
| 2003/0088061 A1 | 5/2003 | Staunton |
| 2003/0092631 A1 | 5/2003 | Deshayes et al. |
| 2003/0138430 A1 | 7/2003 | Stimmel et al. |
| 2003/0165502 A1 | 9/2003 | Fujita-Yamaguchi |
| 2003/0195147 A1 | 10/2003 | Pillutla et al. |
| 2003/0235582 A1 | 12/2003 | Singh et al. |
| 2003/0236190 A1 | 12/2003 | Pillutla et al. |
| 2004/0009154 A1 | 1/2004 | Khan et al. |
| 2004/0009906 A1 | 1/2004 | Kakkis et al. |
| 2004/0018191 A1 | 1/2004 | Wang et al. |
| 2004/0023887 A1 | 2/2004 | Pillutla et al. |
| 2004/0038394 A1 | 2/2004 | Kim et al. |
| 2004/0047835 A1 | 3/2004 | Bianco |
| 2004/0057950 A1 | 3/2004 | Waksal et al. |
| 2004/0086503 A1 | 5/2004 | Cohen et al. |
| 2004/0086511 A1 | 5/2004 | Zack et al. |
| 2004/0102360 A1 | 5/2004 | Barnett et al. |
| 2004/0116330 A1 | 6/2004 | Naito et al. |
| 2004/0142381 A1 | 7/2004 | Hubbard et al. |
| 2004/0166580 A1 | 8/2004 | Plaetinck et al. |
| 2004/0202651 A1 | 10/2004 | Cohen et al. |
| 2004/0228859 A1 | 11/2004 | Graus et al. |
| 2004/0265307 A1 | 12/2004 | Singh et al. |
| 2005/0008642 A1 | 1/2005 | Graus et al. |
| 2005/0009988 A1 | 1/2005 | Harris et al. |
| 2005/0048050 A1 | 3/2005 | Fujita-Yamaguchi |
| 2005/0059672 A1 | 3/2005 | Zhu et al. |
| 2005/0069539 A1 | 3/2005 | Cohen et al. |
| 2005/0084906 A1 | 4/2005 | Goetsch et al. |
| 2005/0136063 A1 | 6/2005 | Wang et al. |
| 2005/0169933 A1 | 8/2005 | Steeves et al. |
| 2005/0176099 A1 | 8/2005 | Saha |
| 2005/0186203 A1 | 8/2005 | Singh et al. |
| 2005/0244408 A1 | 11/2005 | Cohen et al. |
| 2005/0249728 A1 | 11/2005 | Singh et al. |
| 2005/0249730 A1 | 11/2005 | Goetsch et al. |
| 2005/0272637 A1 | 12/2005 | Clinton et al. |
| 2005/0272755 A1 | 12/2005 | Denis et al. |
| 2005/0281812 A1 | 12/2005 | Cohen et al. |
| 2006/0018910 A1 | 1/2006 | Gualberto et al. |
| 2006/0140960 A1 | 6/2006 | Wang et al. |
| 2006/0205810 A1 | 9/2006 | Zong et al. |
| 2006/0233804 A1 | 10/2006 | Dehayes et al. |
| 2006/0233810 A1 | 10/2006 | Wang et al. |
| 2006/0233814 A1 | 10/2006 | Goldmakher |
| 2006/0286103 A1 | 12/2006 | Kolhe et al. |
| 2007/0059241 A1 | 3/2007 | Wang et al. |
| 2007/0059305 A1 | 3/2007 | Wang et al. |
| 2008/0014197 A1 | 1/2008 | Wang et al. |
| 2008/0112888 A1 | 5/2008 | Wang |

FOREIGN PATENT DOCUMENTS

| | | |
|---|---|---|
| FR | 2834900 | 7/2003 |
| FR | 2834990 | 7/2003 |
| FR | 2834991 | 7/2003 |
| WO | WO 91/04014 | 4/1991 |
| WO | WO 91/14438 | 10/1991 |
| WO | WO 97/44352 | 11/1997 |
| WO | WO98/17801 | 4/1998 |
| WO | WO 98/22092 | 5/1998 |
| WO | WO 98/45427 | 10/1998 |
| WO | WO 99/25378 | 5/1999 |
| WO | WO 99/28347 | 6/1999 |
| WO | WO 99/42127 | 8/1999 |
| WO | WO 99/60023 | 11/1999 |
| WO | WO 00/22130 | 4/2000 |
| WO | WO 00/50067 | 8/2000 |
| WO | WO 00/69454 | 11/2000 |
| WO | WO 00/69454 A1 | 11/2000 |
| WO | WO 01/07084 | 2/2001 |
| WO | WO 01/30964 A2 | 5/2001 |
| WO | WO 01/36632 | 5/2001 |
| WO | WO 01/70268 A1 | 9/2001 |
| WO | WO 01/70930 A2 | 9/2001 |
| WO | WO 01/72771 | 10/2001 |
| WO | WO 01/75064 A2 | 10/2001 |
| WO | WO 02/04522 A2 | 1/2002 |
| WO | WO 02/07783 | 1/2002 |
| WO | WO 02/27017 A2 | 4/2002 |
| WO | WO 02/31500 | 4/2002 |
| WO | WO 02/43758 A2 | 6/2002 |
| WO | WO 02/53596 A2 | 7/2002 |
| WO | WO 02/054066 | 7/2002 |
| WO | WO 02/072780 A2 | 9/2002 |
| WO | WO 2004/087756 | 10/2002 |
| WO | WO 02/088752 | 11/2002 |
| WO | WO 02/092599 A1 | 11/2002 |
| WO | WO 02/102854 A2 | 12/2002 |
| WO | WO 02/102972 | 12/2002 |
| WO | WO 02/102973 | 12/2002 |
| WO | WO 03/000928 | 1/2003 |
| WO | WO 03/014696 | 2/2003 |
| WO | WO 03/027246 A2 | 4/2003 |
| WO | WO03/039538 | 5/2003 |
| WO | WO 03/039538 A1 | 5/2003 |
| WO | WO 03/059951 A2 | 7/2003 |
| WO | WO 03/088910 A2 | 10/2003 |
| WO | WO03/100059 | 12/2003 |
| WO | WO 03/106621 A2 | 12/2003 |
| WO | WO 2004/030625 | 4/2004 |
| WO | WO 2004/030627 | 4/2004 |
| WO | WO 2004/056865 | 7/2004 |
| WO | WO 2004/071529 | 8/2004 |
| WO | WO 2004/083248 | 9/2004 |
| WO | WO2004/096224 A2 | 11/2004 |
| WO | WO 2005/005635 | 1/2005 |
| WO | WO 2005/016967 A2 | 2/2005 |
| WO | WO 2005/016970 A2 | 2/2005 |
| WO | WO 2005/016970 A3 | 2/2005 |
| WO | WO2005/052005 | 6/2005 |
| WO | WO2005/061541 | 7/2005 |
| WO | WO2005/117980 | 12/2005 |
| WO | WO2006/013472 | 2/2006 |
| WO | WO2006/020258 | 2/2006 |
| WO | WO2006/069202 | 6/2006 |
| WO | WO 2006/069202 | 6/2006 |
| WO | WO2007/093008 | 8/2007 |

OTHER PUBLICATIONS

Rudikoff et al. Proc. Natl. Acad. Sci. USA, 79(6):1979-1983, Mar. 1982.*

Colman P. M. Research in Immunology, 145:33-36, 1994.*

Bendig M. M. Methods: A Companion to Methods in Enzymology, 8:83-93, 1995.*

MacCallum et al. J. Mol. Biol., 262, 732-745, 1996.*

Casset et al. Biochemical and Biophysical Research Communications, 307:198-205, 2003.*

Stefania Benini et al., Inhibition of Insulin-like Growth Factor I Receptor Increases the Antitumor Activity of Doxorubicin and Vincristine Against Ewing's Sarcoma Cells, Clinical Cancer Research, vol. 7, 1790-1797, Jun. 2001.

V.M. Macaulay, Insulin-like Growth Factors and Cancer, Br. J. Cancer, 65, 311-320, 1992.

Mariana Resnicoff et al., The Role of the Insulin-like Growth Factor I Receptor in Transformation and Apoptosis, Kimmel Cancer Institute, Thomas Jefferson University pp. 76-81.

Xiangdang Liu et al., Inhibition of Insulin-like Growth Factor I Receptor Expression in Neuroblastoma Cells Induces the Regression of Established Tumors in Mice, Cancer Research 58, 5432-5438, Dec. 1, 1998.

Jamie L. Resnik et al., Elevated Insulin-like Growth Factor I Receptor Autophosphorylation and Kinase Activity in Human Breast Cancer, Cancer Research 58, 1159-1164, Mar. 15, 1998.

Fredrika Pekonen et al., Receptors for Epidermal Growth Factor and Insulin-like Growth Factor I and Their Relation to Steroid Receptors in Human Breast Cancer, Cancer Research 48, 1343-1347, Mar. 1, 1988.

Quynh T. Rohlik et al., An Antibody to the Receptor for Insulin-like Growth Factor I Inhibits the Growth of MCF-7 Cells in Tissue Culture, Biochemical and Biophysical Research Communications, vol. 149, No. 1, 276-281, 1987.

Carlos L. Arteaga et al., Blockade of the Type I Somatomedin Receptor Inhibits Growth of Human Breast Cancer Cells in Athymic Mice, J. Clin. Invest., vol. 84, 1418-1423, Nov. 1989.

Ted Gansler et al., Rapid Communication Antibody to Type I Insulin-like Growth Factor Receptor Inhibits Growth of Wilms' Tumor in Culture and in Athymic Mice, American Journal of Pathology, vol. 135, No. 6, 961-966, Dec. 1989.

Krzysztof Reiss et al., Inhibition of Tumor Growth by a Dominant Negative Mutant of the Insulin-like Growth Factor I Receptor with a Bystander Effect, Clinical Cancer Research, vol. 4, 2647-2655, Nov. 1998.

Carlos L. Arteaga et al., Growth Inhibition of Human Breast Cancer Cells in Vitro with an Antobody Against the Type I Somatomedin Receptor, Cancer Research, 49, 6237-6241, Nov. 15, 1989.

Sandra E. Dunn et al., A Dominant Negative Mutant of the Insulin-like Growth Factor-I Receptor Inhibits the Adhesion, Invasion, and Metastasis of Breast Cancer, Cancer Research, 58, 3353-3361, Aug. 1, 1998.

Peter Burfeind, Antisense RNA to the Type I Insulin-like Growth Factor Receptor Suppresses Tumor Growth and Prevents Invasion by Rate Prostate Cancer Cells In Vivo, Proc. Natl. Acad. Sci. USA, vol. 93 7263-7268, Jul. 1996.

Diane Prager et al., Dominant Negative Inhibition of Tumorigenesis In Vivo by Human Insulin-like Growth Factor I Receptor Mutant, Proc. Natl. Acad. Sci. USA, vol. 91, 2181-2185, Mar. 1994.

Deepali Sachdev, A Chimeric Humanized Single-Chain Antibody Against the Type I Insulin-like Growth Factor (IGF) Receptor Renders Breast Cancer Cells Refractory to the Mitogenic Effects of IGF-1, Cancer Research 63: 627-635, 2003.

Hakam et al., Human Pathology (1999) 30(10): 1128-1133.

Sepp-Lorenzino, Breast Cancer Research and Treatment (1998) 47: 235-253.

Happerfield, et al., "The localization of insulin-like growth factor receptor 1 (IGFR1) in benign and malignant breast tissue" Journal of Pathology 183:412-417 (1997).

Xiong et al., "Growth-stimulatory monoclonal antibodies against human insulin-like growth factor I receptor" Proc. Nat. Acad. Sci. 89: 5356-5360 (1992).

Li et al., "Two new monoclonal antibodies against the α subunit of the human insulin-like growth factor-I receptor" Biochem. Biophys. Res. Comm. 196(1):92-98 (1993).

Kull et al., "Monoclonal antibodies to receptors for insulin and somatomedin-C" J. Biol. Chem. 258(10):6561-6566 (1983).

Butler et al., "Insulin-like growth factor-I receptor signal transduction: at the interface between physiology and cell biology" Comp. Biochem. Physiol. (B) 121(1):19-26 (1998).

Chan et al., "Plasma insulin-like growth factor-I and prostate cancer risk: a prospective study" Science. 279(5350):563-566 (1998).

Xie et al., "Expression of insulin-like growth factor-1 receptor in synovial sarcoma: association with an aggressive phenotype" Cancer Res. 59(15):3588-3591 (1999).

Steller et al., "Overexpression of the insulin-like growth factor-1 receptor and autocrine stimulation in human cervical cancer cells" Cancer Res. 56(8):1761-1765 (1996).

Pandini et al., "Insulin and insulin-like growth factor-I (IGF-I) receptor overexpression in breast cancers leads to insulin/IGF-I hybrid receptor overexpression: evidence for a second mechanism of IGF-I signaling" Clin. Cancer Res. 5(7):1935-1944 (1999).

Webster et al., "Repression of the insulin receptor promoter by the tumor suppressor gene product p53: a possible mechanism for receptor overexpression in breast cancer" Cancer Res. 56(12):2781-2788 (1996).

Ben-Schlomo et al., "Acromegaly" Endocrin. Metab. Clin. N. America 30(3):565-583 (2001).

Li et al., "Single-chain antibodies against human insulin-like growth factor I receptor: expression, purification, and effect on tumor growth", Cancer Immunol. Immunother. 49: 243-252 (2000).

Burtrum et al., "A fully human monoclonal antibody to the insulin-like growth factor I receptor blocks ligand-dependent signaling and inhibits human tumor growth in vivo." Cancer Res. Dec. 15, 2003;63(24):8912-21.

Business Wire, "Imclone systems incorporated reports advancements in several pipeline programs" (Jul. 14, 2003).

Zhenping Zhu, "Monoclonal Antibodies in Cancer-Fourth International Congress (Part II), Colorado Springs, CO, USA" Investigational Drug Database Meeting Report (Sep. 3-6, 2004).

Laura Williams, "American Association for Cancer Research-94th Annual Meeting (Part III)-Overnight Report, Washington, D.C., USA" Investigational Drug Database Meeting Report (Jul. 11-14, 2003).

Imclone Systems, Inc. Form 10-K (filed Mar. 15, 2004).

Holt et al., Domain antibodies: proteins for therapy, Trends in Biotechnology 21(11): 484-490 (2003).

Maloney et al., An Anti-Insulin-like Growth Factor I Receptor Antibody That Is a Potent Inhibitor of Cancer Cell Proliferation, Cancer Research 63, 5073-5083 (2003).

Lu et al., Simultaneous Blockade of Both the Epidermal Growth Factor Receptor and the Insulin-like Growth . . . J. Bio. Chem.279(4): 2856-65 (2004).

Tang et al., Use of a peptide mimotope to guide the humanization of MRK-16, an anti-P-glycoprotein monoclonal antibody. J Biol Chem. Sep. 24, 1999;274(39):27371-8.

Boylan et al., The anti-proliferative effect of suramin towards tamoxifen-sensitive and resistant human breast cancer cell lines in relation to expression of receptors for epidermal growth factor and insulin-like growth factor-I: growth stimulation in the presence of tamoxifen. Ann Oncol. Feb. 1998;9(2):205-11.

Happerfield et al., The localization of the insulin-like growth factor receptor 1 (IGFR-1) in benign and malignant breast tissue. J Pathol. Dec. 1997;183(4):412-7.

Clarke et al., Type I insulin-like growth factor receptor gene expression in normal human breast tissue treated with oestrogen and progesterone. Br J Cancer. 1997;75(2):251-7.

Van den berg et al., Expression of receptors for epidermal growth factor and insulin-like growth factor I by ZR-75-1 human breast cancer cell variants is inversely related: the effect of steroid hormones on insulin-like growth factor I receptor expression. Br J Cancer. Feb. 1996;73(4):477-81.

Lebon et al., Purification of insulin-like growth factor I receptor from human placental membranes. J Biol Chem. Jun. 15, 1986;261(17):7685-9.

Warren et al., Induction of vascular endothelial growth factor by insulin-like growth factor 1 in colorectal carcinoma. J Biol Chem. Nov. 15, 1996;271(46):29483-8.

Auclair et al., Antiinsulin receptor autoantibodies induce insulin receptors to constitutively associate with insulin receptor substrate-1 and -2 and cause severe cell resistance to both insulin and insulin-like growth factor I. J Clin Endocrinol Metab. Sep. 1999;84(9):3197-3206.

Gori et al., Effects of androgens on the insulin-like growth factor system in an androgen-responsive human osteoblastic cell line. Endocrinology. Dec. 1999;140(12):5579-86.

Kasprzyk et al., Therapy of an animal model of human gastric cancer using a combination of anti-erbB-2 monoclonal antibodies. Cancer Res. May 15, 1992;52(10):2771-6.

Drebin et al., Monoclonal antibodies reactive with distinct domains of the neu oncogene-encoded p185 molecule exert synergistic antitumor effects in vivo. Oncogene. Mar. 1988;2(3):273-7.

Shin et al., Proapoptotic activity of cell-permeable anti-Akt single-chain antibodies. Cancer Res. Apr. 1, 2005;65(7):2815-24.

Lu et al., A fully human recombinant IgG-like bispecific antibody to both the epidermal growth factor receptor and the insulin-like growth factor receptor for enhanced antitumor activity. J Biol Chem. May 20, 2005;280(20):19665-72.

Cohen et al., Combination therapy enhances the inhibition of tumor growth with the fully human anti-type 1 insulin-like growth factor receptor monoclonal antibody CP-751,871. Clin Cancer Res. Mar. 1, 2005;11(5):2063-73.

Wu et al., In vivo effects of the human type I insulin-like growth factor receptor antibody A 12 on androgen-dependent and androgen-independent xenograft human prostate tumors. Clin Cancer Res. Apr. 15, 2005;11(8):3065-74.

Goetsch et al., A recombinant humanized anti-insulin-like growth factor receptor type I antibody (h7C10) enhances the antitumor activity of vinorelbine and anti-epidermal growth factor receptor therapy against human cancer xenografts. Int J Cancer. Jan. 10, 2005;113(2):316-28.

Granerus et al., Effects of insulin-like growth factor-binding protein 2 and an IGF-type I receptor-blocking antibody on apoptosis in human teratocarcinoma cells in vitro. Cell Biol Int. 2001;25(8):825-8.

Kaliman et al., Antipeptide antibody to the insulin-like growth factor-I receptor sequence 1232-1246 inhibits the receptor kinase activity. J Biol Chem. May 25, 1992;267(15):10645-51.

Rodeck et al., Interactions between growth factor receptors and corresponding monoclonal antibodies in human tumors. J Cell Biochem. Dec. 1987;35(4):315-20.

Iwakiri et al., Autocrine growth of Epstein-Barr virus-positive gastric carcinoma cells mediated by an Epstein-Barr virus-encoded small RNA. Cancer Res. Nov. 1, 2003;63(21):7062-7.

Kiess et al., Human neuroblastoma cells use either insulin-like growth factor-I or insulin-like growth factor-II in an autocrine pathway via the IGF-I receptor: variability of IGF, IGF binding protein (IGFBP) and IGF receptor gene expression and IGF and IGFBP secretion in human neuroblastoma cells in relation to cellular proliferation. Regul Pept. Sep. 26, 1997;72(1):19-29.

Pritchard et al., Synovial fibroblasts from patients with rheumatoid arthritis, like fibroblasts from Graves' disease, express high levels of IL-16 when treated with Igs against insulin-like growth factor-1 receptor. J Immunol. Sep. 1, 2004;173(5):3564-9.

Jackson-Booth et al., Inhibition of the biologic response to insulin-like growth factor I in MCF-7 breast cancer cells by a new monoclonal antibody to the insulin-like growth factor-I receptor. The importance of receptor down-regulation. Horm Metab Res. Nov.-Dec. 2003:35(11-12):850-6.

Carboni et al., Tumor development by transgenic expression of a constitutively active insulin-like growth factor I receptor. Cancer Res. May 1, 2005;65(9):3781-7.

Remacle-Bonnet et al., Insulin-like growth factor-I protects colon cancer cells from death factor-induced apoptosis by potentiating tumor necrosis factor alpha-induced mitogen-activated protein kinase and nuclear factor kappaB signaling pathways. Cancer Res. Apr. 1, 2000;60(7):2007-17.

Lahm et al., Blockade of the insulin-like growth-factor-I receptor inhibits growth of human colorectal cancer cells: evidence of a functional IGF-II-mediated autocrine loop. Int J Cancer. Aug. 1, 1994;58(3):452-9.

Steele-Perkins et al., Monoclonal antibody alpha IR-3 inhibits the ability of insulin-like growth factor II to stimulate a signal from the type I receptor without inhibiting its binding. Biochem Biophys Res Commun. Sep. 28, 1990;171(3):1244-51.

Scotlandi et al., Prognostic and therapeutic relevance of HER2 expression in osteosarcoma and Ewing's sarcoma. Eur J Cancer. Jun. 2005;41(9):1349-61.

Agus et al., Response of prostate cancer to anti-Her-2/neu antibody in androgen-dependent and -independent human xenograft models. Cancer Res. Oct. 1, 1999;59(19):4761-4.

Pietras et al., Monoclonal antibody to HER-2/neureceptor modulates repair of radiation-induced DNA damage and enhances radiosensitivity of human breast cancer cells overexpressing this oncogene. Cancer Res. Mar. 15, 1999;59(6):1347-55.

Goldenberg, Trastuzumab, a recombinant DNA-derived humanized monoclonal antibody, a novel agent for the treatment of metastatic breast cancer. Clin Ther. Feb. 1999;21(2):309-18. Review.

Kull et al., Monoclonal antibodies to receptors for insulin and somatomedin-C. J Biol Chem. May 25, 1983;258(10):6561-6.

Benini et al., Inhibition of insulin-like growth factor I receptor increases the antitumor activity of doxorubicin and vincristine against Ewing's sarcoma cells. Clin Cancer Res. Jun. 2001;7(6):1790-7.

Seely et al., Retroviral expression of a kinase-defective IGF-I receptor suppresses growth and causes apoptosis of CHO and U87 cells in-vivo. BMC Cancer. May 31, 2002;2:15.

Soos et al., A panel of monoclonal antibodies for the type I insulin-like growth factor receptor. Epitope mapping, effects on ligand binding, and biological activity. J Biol Chem. Jun. 25, 1992;267(18):12955-63.

Kalebic et al., In vivo treatment with antibody against IGF-1 receptor suppresses growth of human rhabdomyosarcoma and down-regulates p34cdc2. Cancer Res. Nov. 1, 1994;54(21):5531-4.

Baserga, The insulin-like growth factor I receptor: a key to tumor growth? Cancer Res. Jan. 15, 1995;55(2):249-52.

Rubini et al., Characterization of an antibody that can detect an activated IGF-I receptor in human cancers. Exp Cell Res. Aug. 25, 1999;251(1):22-32.

Hailey et al., Neutralizing anti-insulin-like growth factor receptor 1 antibodies inhibit receptor function and induce receptor degradation in tumor cells, Mol. Cancer Ther. Dec. 2002;1(14):1349-53.

Wang et al., Inhibition of insulin-like growth factor-I receptor (IGF-IR) signaling and tumor cell growth by a fully human neutralizing anti-IGF-IR antibody, Mol Cancer Ther. Aug. 2005;4(8):1214-21.

Davies et al., Antibody VH domains as small recognition units, Biotechnology (N Y). May 1995;13(5):475-9.

Davies et al., Single antibody domains as small recognition units: design and in vitro antigen selection of camelized, human VH domains with improved protein stability. Protein Eng. Jun. 1996;9(6):531-7.

Immunobiology, the immune system in health and disease, 6$^{th}$ edition, Garland Science (NY), 2005, pp. 104-107.

Conrad et al., Considerations on antibody-phage display methodology, Comb. Chem. High Throughput Screen. Mar. 2005;8(2):117-26.

Green, Larry L.; "Antibody engineering via genetic engineering of the mouse: XenoMouse strains are a vehicle for the facile generation of therapeutic human monoclonal antibodies"; Journal of Immunological Methods; 231:11-23 (1999).

Acland, Piers, et al., "Subcellular fate of the int-2 oncoprotein is determined by choice of initiation codon"; Nature 343:662-665 (1990).

Arakawa, Tsutomu, et al., "Factors affecting short-term and long-term stabilities of proteins"; Adv Drug Deliv Rev.; 46(1-3):307-326 (2001).

Back, Joan F., et al., "Increased thermal stability of proteins in the presence of sugars and polyols"; Biochemistry. 18(23):5191-5196 (1997).

Bebbington, Christopher R.; "Expression of antibody genes in nonlymphoid mammalian cells"; Methods: A companion to methods in Enzymology, Academic Press Inc., New York, NY, US, 2(2):136-145 (1991).

Beech, Derrick J., et al., "Insulin-like growth factor-1 receptor antagonism results in increased cytotoxicity of breast cancer cells to doxorubicin and taxol"; Oncology Reports; 8:325-329 (2001).

Bollag, W., et al., "Retinoids in cancer prevention and therapy"; Ann Oncol. 3(7):513-526 (1992).

Bomgaards, Lisa, et al.; "The development of camptothecin analogs in childhood cancers"; Oncologist; 6(6):506-516 (2001).

Burgess, Wilson H., et al.; "Possible dissociation of the heparin-binding and mitogenic activities of heparin-binding (acidic fibroblast) growth factor-1 from its receptor-binding activities by site-directed mutagenesis of a single lysine residue"; J. Cell. Bio.; 111:2129-2138 (1990).

Cordera, Renzo, et al.; "Inhibition of insulin and epidermal growth factor (EGF) receptor autophosphorylation by a human polyclonal IgG"; Biochemical and Biophysical Research Communications; 132(3):991-1000 (1985).

Davies, Julian, et al.; Antibody VH domains as small recognition units. Biotechnology (N Y). May 1995;13(5):475-9.

Davies, Julian, et al.; "Single antibody domains as small recognition units: design and in vitro antigen selection of camelized, human VH domains with improved protein stability"; Protein Eng.; 9(6):531-537 (1996).

Physicians' Desk Reference, 54th edition, Medical Economics Co., New Jersey (2000): Doxil.

Napier & Ledermann, "Novel chemotherapeutic agents in colorectal cancer", Eur J Surg Oncol. Sep. 2000;26(6):605-10.

Gradishar & Jordan, "Clinical potential of new antiestrogens", J Clin Oncol. Feb. 1997;15(2):840-52.

Flamez, Daisy, et al.; "Production in *Escherichia coli* of a functional murine and murine::human chimeric F(ab')2 fragment and mature antibody directed against human placental alkaline phosphatase"; J. Biotechnol. 42(2):133-143 (1995).

Freund, Gregory G., et al.; "Functional insulin and insulin-like growth factor-1 receptors are preferentially expressed in multiple myeloma cell lines as compared to B-lymphoblastoid cell lines"; Cancer Res.; 54(12):3179-3185 (1994).

Greenberger, Lee M., et al.; "A new antiestrogen, 2-(4-hydroxy-phenyl)-3-methyl-1-[4-(2-piperidin-1-yl-ethoxy)-benzyl]-1H-indol-5-ol hydrochloride (ERA-923), inhibits the growth of tamoxifen-sensitive and -resistant tumors and is devoid of uterotropic effects in mice and rats"; Clin Cancer Res.; 7(10):3166-3177 (2001).

Physicians' Desk Reference, 54th edition, Medical Economics Co., New Jersey (2000): Herceptin.

Hunt, John T., et al.; "Discovery of (R)-7-cyano-2,3,4, 5-tetrahydro-1-(1H-imidazol-4-ylmethyl)-3-(phenylmethyl)-4-(2-thienylsulfonyl)-1H-1,4-benzodiazepine (BMS-214662), a farnesyltransferase inhibitor with potent preclinical antitumor activity"; J Med Chem.; 43(20):3587-3595 (2000).

Immunobiology, the immune system in health and disease. 6th edition. Garland Science (NY) pp. 104-106 (2005).

Ciardiello, "Epidermal growth factor receptor tyrosine kinase inhibitors as anticancer agents" Drugs. 2000;60 Suppl 1:25-32.

Ju, Grace, et al.; "Nucleotide sequence analysis of the long terminal repeat (LTR) of avian retroviruses: structural similarities with transposable elements"; Cell.; 22(2 Pt 2):379-86 (1980).

Kaufman, Randal J.; "Selection and coamplification of heterogeneous genes in mammalian cells"; Methods in Enzymology; 185:537-566 (1990).

Ke, Hua Zhu, et al.; "Effects of CP-336,156, a new, nonsteroidal estrogen agonist/antagonist, on bone, serum cholesterol, uterus and body composition in rat models"; Endocrinology; 139(4):2068-2076 (1998).

Komm, Barry S., et al.; "Developing a SERM: stringent preclinical selection criteria leading to an acceptable candidate (WAY-140424) for clinical evaluation"; Ann N Y Acad Sci. 949:317-26: Preface (Sherman); The Basic Biology of SERMs (Margolis); Cancer treatment and prevention (Dunn et al.) (2001).

Lazar, Eliane, et al;"Transforming growth factor alpha: mutation of aspartic acid 47 and leucine 48 results in different biological activities"; Mol. Cell. Bio.; 8(3):1247-1252 (1988).

Lebon, Thomas R., et al., "Purification of insulin-like growth factor I receptor from human placental membranes"; J Biol Chem.; 261(17):7685-7689 (1986).

Lee, James C., et al.; "The stabilization of proteins by sucrose"; J Biol Chem.; 256(14):7193-7201 (1981).

Lin, Michael C., et al.; "Structure-function relationships in glucagon: properties of highly purified des-His-1-, monoiodo-, and (des-Asn-28, Thr-29)(homoserine lactone-27)-glucagon"; Biochemistry; 14(8):1559-1563 (1975).

Liu, Ming, et al., "Antitumor activity of SCH 66336, an orally bioavailable tricyclic inhibitor of farnesyl protein transferase, in human tumor xenograft models and wap-ras transgenic mice"; Cancer Res.; 58(21):4947-4956 (1998).

Malet, Catherine, et al., "Effect of 4-hydroxytamoxifen isomers on growth and ultrastructural aspects of normal human breast epithelial (HBE) cells in culture"; J Steroid Biochem Mol Biol.; 82(4-5):289-96 (2002).

Maurer, R., et al., "Opiate antagonistic properties of an octapeptide somatostatin analog"; Proc Natl Acad Sci U S A. 79(15):4815-4817 (1982).

Noble, Stuart, et al., "Gemcitabine. A review of its pharmacology and clinical potential in non-small cell lung cancer and pancreatic cancer"; Drugs; 54(3):447-472 (1997).

Nordenhaug, Lars, et al., "Versatile vectors for transient and stable expression of recombinant antibody molecules in mammalian cells"; J. Immunol. Methods; 204(1):77-87 (1997).

Page, Martin, J., et al.; "High level expression of the humanized monoclonal antibody campath-1h in Chinese hamster ovary cells"; Biotechnology, Nature publishing Co., New York, NY, US; 9(1):64-68 (1991).

Petit, T., et al., "Activity of SCH 66336, a tricyclic farnesyltransferase inhibitor, against human tumor colony-forming units"; Ann Oncol.; 10(4):449-453 (1999).

Tutrone et al., "Biologic therapy for psoriasis: a brief history, II", Cutis. Dec. 2001;68(6):367-72. Review.

Resnicoff, Mariana, et al., "Rat glioblastoma cells expressing an antisense RNA to the insulin-like growth factor-1 (IGF-1) receptor are nontumorigenic and induce regression of wild-type tumors"; Cancer Res.; 54(8):2218-2222 (1994).

Rudikoff, Stuart, et al.; "Single amino acid substitution altering antigen-binding specificity"; PNAS; 1979:1983 (1982).

Physicians' Desk Reference, 54th edition, Medical Economics Co., New Jersey (2000): Sandostatin.

Sato, Masahiko, et al.; "LY353381.HCl: a novel raloxifene analog with improved SERM potency and efficacy in vivo"; J Pharmacol Exp Ther.; 287(1):1-7 (1998).

Schwartz, Gerald, P., et al.; "A superactive insulin: [B10-aspartic acid]insulin(human)"; PNAS; 84:6408-6411 (1987).

Shepard et al, "Monoclonal Antibodies: A Practical Approach", 2000, Oxford University Press, pp. 58-65.

Physicians' Desk Reference, 54th edition, Medical Economics Co., New Jersey (2000): Synagis.

Takebe, Yutaka, et al., "SR alpha promoter: an efficient and versatile mammalian cDNA expression system composed of the simian virus 40 early promoter and the R-U5 segment of human T-cell leukemia virus type 1 long terminal repeat"; Mol Cell Biol.; 8(1):466-472 (1988).

Taylor, Carol, et al., "Estrogen receptor-mediated and cytotoxic effects of the antiestrogens tamoxifen and 4-hydroxytamoxifen"; Cancer Research; 44:1409-1414 (1984).

Yung et al.., "Multicenter phase II trial of temozolomide in patients with anaplastic astrocytoma or anaplastic oligoastrocytoma at first relapse. Temodal Brain Tumor Group", J Clin Oncol. Sep. 1999;17(9):2762-71.

Adams & Elliott, "New agents in cancer clinical trials", Oncogene. Dec. 27, 2000;19(56):6687-92.

Wahle, Elmar; "The end of the message: 3'-end processing leading to polyadenylated messenger RNA"; Bioessays. 14(2):113-8 (1992).

Wang, Yan, et al.; "Inhibition of insulin-like growth factor-I receptor (IGF-IR) signaling and tumor cell growth by a fully human neutralizing anti-IGF-IR antibody"; Mol Cancer Ther.; 4(8):1214-1221 (2005).

Wang, Wei, et al.; "Instability, stabilization, and formulation of liquid protein pharmaceuticals"; Int J Pharm.; 185(2):129-188 (1999).

Wilhelm, Scott, et al., "BAY 43-9006: preclinical data"; Curr Pharm Des; 8(25):2255-2257 (2002).

Schulman, "Development of a monoclonal anti-immunoglobulin E antibody (omalizumab) for the treatment of allergic respiratory disorders", Am J Respir Crit Care Med. Oct. 15, 2001;164(8 Pt 2):S6-11.

Yeo, Eun-Jin, et al., "YC-1: a potential anticancer drug targeting hypoxia-inducible factor 1"; J Natl Cancer Inst.; 95(7):516-525 (2003).

Zhang, R., et al., "An adenoviral vector expressing functional heterogeneous proteins herpes simplex viral thymidine kinase and human interleukin-2 has enhanced in vivo antitumor activity against medullary thyroid carcinoma"; Endocr. Relat. Cancer; 8(4):315-325 (2001).

Zujewski, J., et al., "Phase I and pharmacokinetic study of farnesyl protein transferase inhibitor R115777 in advanced cancer"; J. Clin Oncol.; 18(4):927-941 (2000).

* cited by examiner

SEQUENCE LISTING

```
<160> NUMBER OF SEQ ID NOS: 120

<210> SEQ ID NO 1
<211> LENGTH: 384
<212> TYPE: DNA
<213> ORGANISM: Homo sapiens
<220> FEATURE:
<221> NAME/KEY: CDS
<222> LOCATION: 1..384
<223> OTHER INFORMATION:
<220> FEATURE:
<221> NAME/KEY: sig_peptide
<222> LOCATION: 1..57
<223> OTHER INFORMATION:

<400> SEQUENCE: 1 atg tcg cca tca caa ctc att ggg ttt ctg ctg ctc tgg gtt cca gcc      48
Met Ser Pro Ser Gln Leu Ile Gly Phe Leu Leu Leu Trp Val Pro Ala
1               5                   10                  15 tcc agg ggt gaa att gtg ctg act cag gtt cca gac ttt cag tct gtg      96
Ser Arg Gly Glu Ile Val Leu Thr Gln Val Pro Asp Phe Gln Ser Val
                20                  25                  30 act cca aag gag aaa gtc acc atc acc tgc cgg gcc agt cag agc att     144
Thr Pro Lys Glu Lys Val Thr Ile Thr Cys Arg Ala Ser Gln Ser Ile
            35                  40                  45 ggt agt agc tta cac tgg tac cag cag aaa cca gat cag tct cca aag     192
Gly Ser Ser Leu His Trp Tyr Gln Gln Lys Pro Asp Gln Ser Pro Lys
        50                  55                  60 ctc ctc atc aag tat gct tcc cag tcc ctc tca ggg gtc ccc tcg agg     240
Leu Leu Ile Lys Tyr Ala Ser Gln Ser Leu Ser Gly Val Pro Ser Arg
65                  70                  75                  80 ttc agt ggc agt gga tct ggg aca gat ttc acc ctc acc atc aat agc     288
Phe Ser Gly Ser Gly Ser Gly Thr Asp Phe Thr Leu Thr Ile Asn Ser
                85                  90                  95 ctg gaa gct gaa gat gct gca gcg tat tac tgt cat cag agt agt cgt     336
Leu Glu Ala Glu Asp Ala Ala Ala Tyr Tyr Cys His Gln Ser Ser Arg
            100                 105                 110 tta cct cac act ttc ggc gga ggg acc aag gtg gag atc aaa cga act     384
Leu Pro His Thr Phe Gly Gly Gly Thr Lys Val Glu Ile Lys Arg Thr
        115                 120                 125

<210> SEQ ID NO 2
<211> LENGTH: 128
<212> TYPE: PRT
<213> ORGANISM: Homo sapiens

<400> SEQUENCE: 2

Met Ser Pro Ser Gln Leu Ile Gly Phe Leu Leu Leu Trp Val Pro Ala
1               5                   10                  15

Ser Arg Gly Glu Ile Val Leu Thr Gln Val Pro Asp Phe Gln Ser Val
                20                  25                  30

Thr Pro Lys Glu Lys Val Thr Ile Thr Cys Arg Ala Ser Gln Ser Ile
```

```
                    35                  40                  45
Gly Ser Ser Leu His Trp Tyr Gln Gln Lys Pro Asp Gln Ser Pro Lys
 50                  55                  60

Leu Leu Ile Lys Tyr Ala Ser Gln Ser Leu Ser Gly Val Pro Ser Arg
 65                  70                  75                  80

Phe Ser Gly Ser Gly Ser Gly Thr Asp Phe Thr Leu Thr Ile Asn Ser
                 85                  90                  95

Leu Glu Ala Glu Asp Ala Ala Ala Tyr Tyr Cys His Gln Ser Ser Arg
            100                 105                 110

Leu Pro His Thr Phe Gly Gly Gly Thr Lys Val Glu Ile Lys Arg Thr
        115                 120                 125

<210> SEQ ID NO 3
<211> LENGTH: 411
<212> TYPE: DNA
<213> ORGANISM: Homo sapiens
<220> FEATURE:
<221> NAME/KEY: CDS
<222> LOCATION: 1..411
<223> OTHER INFORMATION:
<220> FEATURE:
<221> NAME/KEY: sig_peptide
<222> LOCATION: 1..57
<223> OTHER INFORMATION:

<400> SEQUENCE: 3 atg gag ttt ggg ctg agc tgg gtt ttc ctt gtt gct ata tta aaa ggt      48
Met Glu Phe Gly Leu Ser Trp Val Phe Leu Val Ala Ile Leu Lys Gly
 1               5                  10                  15 gtc cag tgt gag gtt cag ctg gtg cag tct ggg gga ggc ttg gta cat      96
Val Gln Cys Glu Val Gln Leu Val Gln Ser Gly Gly Gly Leu Val His
             20                  25                  30 cct ggg ggg tcc ctg aga ctc tcc tgt gca gcc tct gga ttc acc ttc     144
Pro Gly Gly Ser Leu Arg Leu Ser Cys Ala Ala Ser Gly Phe Thr Phe
         35                  40                  45 agt agc ttt gct atg cac tgg gtt cgc cag gct cca gga aaa ggt ctg     192
Ser Ser Phe Ala Met His Trp Val Arg Gln Ala Pro Gly Lys Gly Leu
     50                  55                  60 gag tgg ata tca gtt att gat act cgt ggt gcc aca tac tat gca gac     240
Glu Trp Ile Ser Val Ile Asp Thr Arg Gly Ala Thr Tyr Tyr Ala Asp
 65                  70                  75                  80 tcc gtg aag ggc cga ttc acc atc tcc aga gac aat gcc aag aac tcc     288
Ser Val Lys Gly Arg Phe Thr Ile Ser Arg Asp Asn Ala Lys Asn Ser
                 85                  90                  95 ttg tat ctt caa atg aac agc ctg aga gcc gag gac atg gct gtg tat     336
Leu Tyr Leu Gln Met Asn Ser Leu Arg Ala Glu Asp Met Ala Val Tyr
            100                 105                 110 tac tgt gca aga ctg ggg aac ttc tac tac ggt atg gac gtc tgg ggc     384
Tyr Cys Ala Arg Leu Gly Asn Phe Tyr Tyr Gly Met Asp Val Trp Gly
        115                 120                 125 caa ggg acc acg gtc acc gtc tcc tca                                 411
Gln Gly Thr Thr Val Thr Val Ser Ser
    130                 135

<210> SEQ ID NO 4
<211> LENGTH: 137
<212> TYPE: PRT
<213> ORGANISM: Homo sapiens

<400> SEQUENCE: 4

Met Glu Phe Gly Leu Ser Trp Val Phe Leu Val Ala Ile Leu Lys Gly
 1               5                  10                  15
```

-continued

Val Gln Cys Glu Val Gln Leu Val Gln Ser Gly Gly Gly Leu Val His
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
    50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Met Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
    130                 135

<210> SEQ ID NO 5
<211> LENGTH: 33
<212> TYPE: DNA
<213> ORGANISM: Homo sapiens

<400> SEQUENCE: 5
cgggccagtc agagcattgg tagtagctta cac                         33

<210> SEQ ID NO 6
<211> LENGTH: 21
<212> TYPE: DNA
<213> ORGANISM: Homo sapiens

<400> SEQUENCE: 6
tatgcttccc agtccctctc a                                      21

<210> SEQ ID NO 7
<211> LENGTH: 27
<212> TYPE: DNA
<213> ORGANISM: Homo sapiens

<400> SEQUENCE: 7
catcagagta gtcgtttacc tcacact                                27

<210> SEQ ID NO 8
<211> LENGTH: 11
<212> TYPE: PRT
<213> ORGANISM: Homo sapiens

<400> SEQUENCE: 8

Arg Ala Ser Gln Ser Ile Gly Ser Ser Leu His
1               5                   10

<210> SEQ ID NO 9
<211> LENGTH: 7
<212> TYPE: PRT
<213> ORGANISM: Homo sapiens

<400> SEQUENCE: 9

Tyr Ala Ser Gln Ser Leu Ser
1               5

<210> SEQ ID NO 10

```
<211> LENGTH: 9
<212> TYPE: PRT
<213> ORGANISM: Homo sapiens

<400> SEQUENCE: 10

His Gln Ser Ser Arg Leu Pro His Thr
1               5

<210> SEQ ID NO 11
<211> LENGTH: 15
<212> TYPE: DNA
<213> ORGANISM: Homo sapiens

<400> SEQUENCE: 11
agctttgcta tgcac                                                    15

<210> SEQ ID NO 12
<211> LENGTH: 48
<212> TYPE: DNA
<213> ORGANISM: Homo sapiens

<400> SEQUENCE: 12
gttattgata ctcgtggtgc cacatactat gcagactccg tgaagggc                48

<210> SEQ ID NO 13
<211> LENGTH: 30
<212> TYPE: DNA
<213> ORGANISM: Homo sapiens

<400> SEQUENCE: 13
ctggggaact tctactacgg tatggacgtc                                    30

<210> SEQ ID NO 14
<211> LENGTH: 5
<212> TYPE: PRT
<213> ORGANISM: Homo sapiens

<400> SEQUENCE: 14

Ser Phe Ala Met His
1               5

<210> SEQ ID NO 15
<211> LENGTH: 16
<212> TYPE: PRT
<213> ORGANISM: Homo sapiens

<400> SEQUENCE: 15

Val Ile Asp Thr Arg Gly Ala Thr Tyr Tyr Ala Asp Ser Val Lys Gly
1               5                   10                  15

<210> SEQ ID NO 16
<211> LENGTH: 10
<212> TYPE: PRT
<213> ORGANISM: Homo sapiens

<400> SEQUENCE: 16

Leu Gly Asn Phe Tyr Tyr Gly Met Asp Val
1               5                   10

<210> SEQ ID NO 17
<211> LENGTH: 10
<212> TYPE: PRT
<213> ORGANISM: Homo sapiens

<400> SEQUENCE: 17
```

```
Gly Phe Thr Phe Ser Ser Phe Ala Met His
1               5                   10
```

<210> SEQ ID NO 18
<211> LENGTH: 30
<212> TYPE: DNA
<213> ORGANISM: Homo sapiens

<400> SEQUENCE: 18
ggattcacct tcagtagctt tgctatgcac                                    30

<210> SEQ ID NO 19
<211> LENGTH: 1367
<212> TYPE: PRT
<213> ORGANISM: Homo sapiens

<400> SEQUENCE: 19

```
Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
            115                 120                 125

Gly Leu Tyr Asn Leu Arg Asn Ile Thr Arg Gly Ala Ile Arg Ile Glu
130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
            195                 200                 205

Asn Arg Cys Gln Lys Met Cys Pro Ser Thr Cys Gly Lys Arg Ala Cys
210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
            275                 280                 285

Glu Ser Ser Asp Ser Glu Gly Phe Val Ile His Asp Gly Glu Cys Met
290                 295                 300
```

-continued

```
Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
            325                 330                 335

Lys Thr Lys Thr Ile Asp Ser Val Thr Ser Ala Gln Met Leu Gln Gly
                340                 345                 350

Cys Thr Ile Phe Lys Gly Asn Leu Leu Ile Asn Ile Arg Arg Gly Asn
        355                 360                 365

Asn Ile Ala Ser Glu Leu Glu Asn Phe Met Gly Leu Ile Glu Val Val
    370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
        420                 425                 430

Asp Trp Asp His Arg Asn Leu Thr Ile Lys Ala Gly Lys Met Tyr Phe
    435                 440                 445

Ala Phe Asn Pro Lys Leu Cys Val Ser Glu Ile Tyr Arg Met Glu Glu
    450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Thr Trp His Arg Tyr
        500                 505                 510

Arg Pro Pro Asp Tyr Arg Asp Leu Ile Ser Phe Thr Val Tyr Tyr Lys
    515                 520                 525

Glu Ala Pro Phe Lys Asn Val Thr Glu Tyr Asp Gly Gln Asp Ala Cys
    530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
        580                 585                 590

His Ile Arg Gly Ala Lys Ser Glu Ile Leu Tyr Ile Arg Thr Asn Ala
    595                 600                 605

Ser Val Pro Ser Ile Pro Leu Asp Val Leu Ser Ala Ser Asn Ser Ser
    610                 615                 620

Ser Gln Leu Ile Val Lys Trp Asn Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
        660                 665                 670

Tyr Ala Asp Gly Thr Ile Asp Ile Glu Glu Val Thr Glu Asn Pro Lys
    675                 680                 685

Thr Glu Val Cys Gly Gly Glu Lys Gly Pro Cys Cys Ala Cys Pro Lys
    690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
```

-continued

```
                725                 730                 735
Arg Lys Arg Arg Asp Val Met Gln Val Ala Asn Thr Thr Met Ser Ser
            740                 745                 750
Arg Ser Arg Asn Thr Thr Ala Ala Asp Thr Tyr Asn Ile Thr Asp Pro
            755                 760                 765
Glu Glu Leu Glu Thr Glu Tyr Pro Phe Phe Glu Ser Arg Val Asp Asn
            770                 775                 780
Lys Glu Arg Thr Val Ile Ser Asn Leu Arg Pro Phe Thr Leu Tyr Arg
785                 790                 795                 800
Ile Asp Ile His Ser Cys Asn His Glu Ala Glu Lys Leu Gly Cys Ser
            805                 810                 815
Ala Ser Asn Phe Val Phe Ala Arg Thr Met Pro Ala Glu Gly Ala Asp
            820                 825                 830
Asp Ile Pro Gly Pro Val Thr Trp Glu Pro Arg Pro Glu Asn Ser Ile
            835                 840                 845
Phe Leu Lys Trp Pro Glu Pro Glu Asn Pro Asn Gly Leu Ile Leu Met
            850                 855                 860
Tyr Glu Ile Lys Tyr Gly Ser Gln Val Glu Asp Gln Arg Glu Cys Val
865                 870                 875                 880
Ser Arg Gln Glu Tyr Arg Lys Tyr Gly Gly Ala Lys Leu Asn Arg Leu
            885                 890                 895
Asn Pro Gly Asn Tyr Thr Ala Arg Ile Gln Ala Thr Ser Leu Ser Gly
            900                 905                 910
Asn Gly Ser Trp Thr Asp Pro Val Phe Phe Tyr Val Gln Ala Lys Thr
            915                 920                 925
Gly Tyr Glu Asn Phe Ile His Leu Ile Ile Ala Leu Pro Val Ala Val
            930                 935                 940
Leu Leu Ile Val Gly Gly Leu Val Ile Met Leu Tyr Val Phe His Arg
945                 950                 955                 960
Lys Arg Asn Asn Ser Arg Leu Gly Asn Gly Val Leu Tyr Ala Ser Val
            965                 970                 975
Asn Pro Glu Tyr Phe Ser Ala Ala Asp Val Tyr Val Pro Asp Glu Trp
            980                 985                 990
Glu Val Ala Arg Glu Lys Ile Thr Met Ser Arg Glu Leu Gly Gln Gly
            995                1000                1005
Ser Phe Gly Met Val Tyr Glu Gly Val Ala Lys Gly Val Val Lys
            1010                1015                1020
Asp Glu Pro Glu Thr Arg Val Ala Ile Lys Thr Val Asn Glu Ala
            1025                1030                1035
Ala Ser Met Arg Glu Arg Ile Glu Phe Leu Asn Glu Ala Ser Val
            1040                1045                1050
Met Lys Glu Phe Asn Cys His His Val Val Arg Leu Leu Gly Val
            1055                1060                1065
Val Ser Gln Gly Gln Pro Thr Leu Val Ile Met Glu Leu Met Thr
            1070                1075                1080
Arg Gly Asp Leu Lys Ser Tyr Leu Arg Ser Leu Arg Pro Glu Met
            1085                1090                1095
Glu Asn Asn Pro Val Leu Ala Pro Pro Ser Leu Ser Lys Met Ile
            1100                1105                1110
Gln Met Ala Gly Glu Ile Ala Asp Gly Met Ala Tyr Leu Asn Ala
            1115                1120                1125
Asn Lys Phe Val His Arg Asp Leu Ala Ala Arg Asn Cys Met Val
            1130                1135                1140
```

```
Ala Glu Asp Phe Thr Val Lys Ile Gly Asp Phe Gly Met Thr Arg
    1145                1150                1155

Asp Ile Tyr Glu Thr Asp Tyr Tyr Arg Lys Gly Lys Gly Leu
    1160                1165                1170

Leu Pro Val Arg Trp Met Ser Pro Glu Ser Leu Lys Asp Gly Val
    1175                1180                1185

Phe Thr Thr Tyr Ser Asp Val Trp Ser Phe Gly Val Val Leu Trp
    1190                1195                1200

Glu Ile Ala Thr Leu Ala Glu Gln Pro Tyr Gln Gly Leu Ser Asn
    1205                1210                1215

Glu Gln Val Leu Arg Phe Val Met Glu Gly Gly Leu Leu Asp Lys
    1220                1225                1230

Pro Asp Asn Cys Pro Asp Met Leu Phe Glu Leu Met Arg Met Cys
    1235                1240                1245

Trp Gln Tyr Asn Pro Lys Met Arg Pro Ser Phe Leu Glu Ile Ile
    1250                1255                1260

Ser Ser Ile Lys Glu Glu Met Glu Pro Gly Phe Arg Glu Val Ser
    1265                1270                1275

Phe Tyr Tyr Ser Glu Glu Asn Lys Leu Pro Glu Pro Glu Glu Leu
    1280                1285                1290

Asp Leu Glu Pro Glu Asn Met Glu Ser Val Pro Leu Asp Pro Ser
    1295                1300                1305

Ala Ser Ser Ser Ser Leu Pro Leu Pro Asp Arg His Ser Gly His
    1310                1315                1320

Lys Ala Glu Asn Gly Pro Gly Pro Gly Val Leu Val Leu Arg Ala
    1325                1330                1335

Ser Phe Asp Glu Arg Gln Pro Tyr Ala His Met Asn Gly Gly Arg
    1340                1345                1350

Lys Asn Glu Arg Ala Leu Pro Leu Pro Gln Ser Ser Thr Cys
    1355                1360                1365

<210> SEQ ID NO 20
<211> LENGTH: 195
<212> TYPE: PRT
<213> ORGANISM: Homo sapiens

<400> SEQUENCE: 20

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser His Leu
                20                  25                  30

Phe Tyr Leu Ala Leu Cys Leu Leu Thr Phe Thr Ser Ser Ala Thr Ala
                35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
                100                 105                 110

Lys Pro Ala Lys Ser Ala Arg Ser Val Arg Ala Gln Arg His Thr Asp
                115                 120                 125

Met Pro Lys Thr Gln Lys Tyr Gln Pro Pro Ser Thr Asn Lys Asn Thr
```

-continued

```
            130                 135                 140
Lys Ser Gln Arg Arg Lys Gly Trp Pro Lys Thr His Pro Gly Gly Glu
145                 150                 155                 160

Gln Lys Glu Gly Thr Glu Ala Ser Leu Gln Ile Arg Gly Lys Lys Lys
                165                 170                 175

Glu Gln Arg Arg Glu Ile Gly Ser Arg Asn Ala Glu Cys Arg Gly Lys
            180                 185                 190

Lys Gly Lys
        195

<210> SEQ ID NO 21
<211> LENGTH: 180
<212> TYPE: PRT
<213> ORGANISM: Homo sapiens

<400> SEQUENCE: 21

Met Gly Ile Pro Met Gly Lys Ser Met Leu Val Leu Leu Thr Phe Leu
1               5                   10                  15

Ala Phe Ala Ser Cys Cys Ile Ala Ala Tyr Arg Pro Ser Glu Thr Leu
            20                  25                  30

Cys Gly Gly Glu Leu Val Asp Thr Leu Gln Phe Val Cys Gly Asp Arg
        35                  40                  45

Gly Phe Tyr Phe Ser Arg Pro Ala Ser Arg Val Ser Arg Arg Ser Arg
    50                  55                  60

Gly Ile Val Glu Glu Cys Cys Phe Arg Ser Cys Asp Leu Ala Leu Leu
65                  70                  75                  80

Glu Thr Tyr Cys Ala Thr Pro Ala Lys Ser Glu Arg Asp Val Ser Thr
                85                  90                  95

Pro Pro Thr Val Leu Pro Asp Asn Phe Pro Arg Tyr Pro Val Gly Lys
            100                 105                 110

Phe Phe Gln Tyr Asp Thr Trp Lys Gln Ser Thr Gln Arg Leu Arg Arg
        115                 120                 125

Gly Leu Pro Ala Leu Leu Arg Ala Arg Arg Gly His Val Leu Ala Lys
    130                 135                 140

Glu Leu Glu Ala Phe Arg Glu Ala Lys Arg His Arg Pro Leu Ile Ala
145                 150                 155                 160

Leu Pro Thr Gln Asp Pro Ala His Gly Gly Ala Pro Pro Glu Met Ala
                165                 170                 175

Ser Asn Arg Lys
        180

<210> SEQ ID NO 22
<211> LENGTH: 21
<212> TYPE: DNA
<213> ORGANISM: Artificial sequence
<220> FEATURE:
<223> OTHER INFORMATION: PCR primer

<400> SEQUENCE: 22
tgccaggggg aagaccgatg g                                          21

<210> SEQ ID NO 23
<211> LENGTH: 20
<212> TYPE: DNA
<213> ORGANISM: Artificial sequence
<220> FEATURE:
<223> OTHER INFORMATION: PCR primer

<400> SEQUENCE: 23
```

```
cgggaagatg aagacagatg                                                    20

<210> SEQ ID NO 24
<211> LENGTH: 390
<212> TYPE: DNA
<213> ORGANISM: Homo sapiens
<220> FEATURE:
<221> NAME/KEY: CDS
<222> LOCATION: (1)..(390)
<223> OTHER INFORMATION:
<220> FEATURE:
<221> NAME/KEY: sig_peptide
<222> LOCATION: (1)..(60)
<223> OTHER INFORMATION:

<400> SEQUENCE: 24 atg gaa gcc cca gct cag ctt ctc ttc ctc ctg cta ctc tgg ctc cca       48
Met Glu Ala Pro Ala Gln Leu Leu Phe Leu Leu Leu Leu Trp Leu Pro
 1               5                  10                  15 gat acc acc gga gaa att gtg ttg aca cag tct cca gcc acc ctg tct       96
Asp Thr Thr Gly Glu Ile Val Leu Thr Gln Ser Pro Ala Thr Leu Ser
             20                  25                  30 ttg tct cca ggg gaa aga gcc acc ctc tcc tgc agg gcc agt cag agt      144
Leu Ser Pro Gly Glu Arg Ala Thr Leu Ser Cys Arg Ala Ser Gln Ser
         35                  40                  45 gtt agc agt ttc tta gcc tgg tac caa cag aaa cct ggc cag gct ccc      192
Val Ser Ser Phe Leu Ala Trp Tyr Gln Gln Lys Pro Gly Gln Ala Pro
     50                  55                  60 agg ctc ctc atc tat gat gca tcc aac agg gcc cct ggc atc cca gcc      240
Arg Leu Leu Ile Tyr Asp Ala Ser Asn Arg Ala Pro Gly Ile Pro Ala
 65                  70                  75                  80 agg ttc agt ggc agt ggg tct ggg aca gac ttc act ctc acc atc agc      288
Arg Phe Ser Gly Ser Gly Ser Gly Thr Asp Phe Thr Leu Thr Ile Ser
                 85                  90                  95 agc cta gag cct gaa gat ttt gca gtt tat tac tgt cag cag cgt agc      336
Ser Leu Glu Pro Glu Asp Phe Ala Val Tyr Tyr Cys Gln Gln Arg Ser
            100                 105                 110 aac tgg cct cgg tgg acg ttc ggc caa ggg acc aag gtg gaa atc aaa      384
Asn Trp Pro Arg Trp Thr Phe Gly Gln Gly Thr Lys Val Glu Ile Lys
        115                 120                 125 cga act                                                              390
Arg Thr
    130

<210> SEQ ID NO 25
<211> LENGTH: 130
<212> TYPE: PRT
<213> ORGANISM: Homo sapiens

<400> SEQUENCE: 25

Met Glu Ala Pro Ala Gln Leu Leu Phe Leu Leu Leu Leu Trp Leu Pro
 1               5                  10                  15

Asp Thr Thr Gly Glu Ile Val Leu Thr Gln Ser Pro Ala Thr Leu Ser
             20                  25                  30

Leu Ser Pro Gly Glu Arg Ala Thr Leu Ser Cys Arg Ala Ser Gln Ser
         35                  40                  45

Val Ser Ser Phe Leu Ala Trp Tyr Gln Gln Lys Pro Gly Gln Ala Pro
     50                  55                  60

Arg Leu Leu Ile Tyr Asp Ala Ser Asn Arg Ala Pro Gly Ile Pro Ala
 65                  70                  75                  80

Arg Phe Ser Gly Ser Gly Ser Gly Thr Asp Phe Thr Leu Thr Ile Ser
```

```
                    85                  90                  95
Ser Leu Glu Pro Glu Asp Phe Ala Val Tyr Tyr Cys Gln Gln Arg Ser
                100                 105                 110
Asn Trp Pro Arg Trp Thr Phe Gly Gln Gly Thr Lys Val Glu Ile Lys
        115                 120                 125
Arg Thr
    130

<210> SEQ ID NO 26
<211> LENGTH: 420
<212> TYPE: DNA
<213> ORGANISM: Homo sapiens
<220> FEATURE:
<221> NAME/KEY: CDS
<222> LOCATION: (1)..(420)
<223> OTHER INFORMATION:
<220> FEATURE:
<221> NAME/KEY: sig_peptide
<222> LOCATION: (1)..(57)
<223> OTHER INFORMATION:

<400> SEQUENCE: 26 atg gag ttt ggg ctg agc tgg gtt ttc ctt gtg gct ata tta aaa ggt    48
Met Glu Phe Gly Leu Ser Trp Val Phe Leu Val Ala Ile Leu Lys Gly
1               5                   10                  15 gtc cag tgt gag gtt cag ctg gtg cag tct ggg gga ggc ttg gta ctt    96
Val Gln Cys Glu Val Gln Leu Val Gln Ser Gly Gly Gly Leu Val Leu
            20                  25                  30 cct ggg ggg tcc ctg aga ctc tcc tgt gca ggc tct gga ttc acc ttc   144
Pro Gly Gly Ser Leu Arg Leu Ser Cys Ala Gly Ser Gly Phe Thr Phe
        35                  40                  45 agt aac tat gct atg cac tgg att cgc cag gct cca gga aaa ggt ctg   192
Ser Asn Tyr Ala Met His Trp Ile Arg Gln Ala Pro Gly Lys Gly Leu
    50                  55                  60 gag tgg gtg tca gct att ggt gct ggt ggt gac acg tac tat gca gac   240
Glu Trp Val Ser Ala Ile Gly Ala Gly Gly Asp Thr Tyr Tyr Ala Asp
65                  70                  75                  80 tcc gtg aag ggc cga ttc acc atc tcc aga gac aac gcc aag gac tcc   288
Ser Val Lys Gly Arg Phe Thr Ile Ser Arg Asp Asn Ala Lys Asp Ser
                85                  90                  95 ttg tat ctt caa atg aac agc ctg aga gcc gag gac atg gct gtt tat   336
Leu Tyr Leu Gln Met Asn Ser Leu Arg Ala Glu Asp Met Ala Val Tyr
            100                 105                 110 tac tgt gca aga ggc cgg cat agg aac tgg tac tac tac aat aag gac   384
Tyr Cys Ala Arg Gly Arg His Arg Asn Trp Tyr Tyr Tyr Asn Lys Asp
        115                 120                 125 tac tgg ggc cag gga acc ctg gtc acc gtc tcc tca                   420
Tyr Trp Gly Gln Gly Thr Leu Val Thr Val Ser Ser
    130                 135                 140

<210> SEQ ID NO 27
<211> LENGTH: 140
<212> TYPE: PRT
<213> ORGANISM: Homo sapiens

<400> SEQUENCE: 27

Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val Leu
            20                  25                  30

Pro Gly Gly Ser Leu Arg Leu Ser Cys Ala Gly Ser Gly Phe Thr Phe
        35                  40                  45
```

```
Ser Asn Tyr Ala Met His Trp Ile Arg Gln Ala Pro Gly Lys Gly Leu
         50                  55                  60

Glu Trp Val Ser Ala Ile Gly Ala Gly Gly Asp Thr Tyr Tyr Ala Asp
 65                  70                  75                  80

Ser Val Lys Gly Arg Phe Thr Ile Ser Arg Asp Asn Ala Lys Asp Ser
                 85                  90                  95

Leu Tyr Leu Gln Met Asn Ser Leu Arg Ala Glu Asp Met Ala Val Tyr
                100                 105                 110

Tyr Cys Ala Arg Gly Arg His Arg Asn Trp Tyr Tyr Asn Lys Asp
            115                 120                 125

Tyr Trp Gly Gln Gly Thr Leu Val Thr Val Ser Ser
    130                 135                 140
```

<210> SEQ ID NO 28
<211> LENGTH: 33
<212> TYPE: DNA
<213> ORGANISM: Homo sapiens

<400> SEQUENCE: 28
agggccagtc agagtgttag cagtttctta gcc                        33

<210> SEQ ID NO 29
<211> LENGTH: 21
<212> TYPE: DNA
<213> ORGANISM: Homo sapiens

<400> SEQUENCE: 29
gatgcatcca acagggcccc t                                     21

<210> SEQ ID NO 30
<211> LENGTH: 30
<212> TYPE: DNA
<213> ORGANISM: Homo sapiens

<400> SEQUENCE: 30
cagcagcgta gcaactggcc tcggtggacg                            30

<210> SEQ ID NO 31
<211> LENGTH: 11
<212> TYPE: PRT
<213> ORGANISM: Homo sapiens

<400> SEQUENCE: 31

Arg Ala Ser Gln Ser Val Ser Ser Phe Leu Ala
 1               5                  10

<210> SEQ ID NO 32
<211> LENGTH: 7
<212> TYPE: PRT
<213> ORGANISM: Homo sapiens

<400> SEQUENCE: 32

Asp Ala Ser Asn Arg Ala Pro
 1               5

<210> SEQ ID NO 33
<211> LENGTH: 10
<212> TYPE: PRT
<213> ORGANISM: Homo sapiens

<400> SEQUENCE: 33

```
Gln Gln Arg Ser Asn Trp Pro Arg Trp Thr
1               5                   10
```

<210> SEQ ID NO 34
<211> LENGTH: 30
<212> TYPE: DNA
<213> ORGANISM: Homo sapiens

<400> SEQUENCE: 34
ggattcacct tcagtaacta tgctatgcac                                          30

<210> SEQ ID NO 35
<211> LENGTH: 48
<212> TYPE: DNA
<213> ORGANISM: Homo sapiens

<400> SEQUENCE: 35
gctattggtg ctggtggtga cacgtactat gcagactccg tgaagggc                      48

<210> SEQ ID NO 36
<211> LENGTH: 39
<212> TYPE: DNA
<213> ORGANISM: Homo sapiens

<400> SEQUENCE: 36
ggccggcata ggaactggta ctactacaat aaggactac                                39

<210> SEQ ID NO 37
<211> LENGTH: 10
<212> TYPE: PRT
<213> ORGANISM: Homo sapiens

<400> SEQUENCE: 37

```
Gly Phe Thr Phe Ser Asn Tyr Ala Met His
1               5                   10
```

<210> SEQ ID NO 38
<211> LENGTH: 16
<212> TYPE: PRT
<213> ORGANISM: Homo sapiens

<400> SEQUENCE: 38

```
Ala Ile Gly Ala Gly Gly Asp Thr Tyr Tyr Ala Asp Ser Val Lys Gly
1               5                   10                  15
```

<210> SEQ ID NO 39
<211> LENGTH: 13
<212> TYPE: PRT
<213> ORGANISM: Homo sapiens

<400> SEQUENCE: 39

```
Gly Arg His Arg Asn Trp Tyr Tyr Tyr Asn Lys Asp Tyr
1               5                   10
```

<210> SEQ ID NO 40
<211> LENGTH: 384
<212> TYPE: DNA
<213> ORGANISM: Homo sapiens
<220> FEATURE:
<221> NAME/KEY: CDS
<222> LOCATION: (1)..(384)
<223> OTHER INFORMATION:

<400> SEQUENCE: 40 atg tcg cca tca caa ctc att ggg ttt ctg ctg ctc tgg gtt cca gcc           48

```
              Met Ser Pro Ser Gln Leu Ile Gly Phe Leu Leu Leu Trp Val Pro Ala
              1               5                   10                  15 tcc agg ggt gaa att gtg ctg act cag agc cca gac tct ctg tct gtg        96
Ser Arg Gly Glu Ile Val Leu Thr Gln Ser Pro Asp Ser Leu Ser Val
            20                  25                  30 act cca ggc gag aga gtc acc atc acc tgc cgg gcc agt cag agc att       144
Thr Pro Gly Glu Arg Val Thr Ile Thr Cys Arg Ala Ser Gln Ser Ile
        35                  40                  45 ggt agc agc tta cac tgg tac cag cag aaa cca ggt cag tct cca aag       192
Gly Ser Ser Leu His Trp Tyr Gln Gln Lys Pro Gly Gln Ser Pro Lys
    50                  55                  60 ctt ctc atc tac tat gct tcc cag tcc ctc tca ggg gtc ccc tcg agg       240
Leu Leu Ile Tyr Tyr Ala Ser Gln Ser Leu Ser Gly Val Pro Ser Arg
65                  70                  75                  80 ttc agt ggc agt gga tct ggg aca gat ttc acc ctc acc atc agt agc       288
Phe Ser Gly Ser Gly Ser Gly Thr Asp Phe Thr Leu Thr Ile Ser Ser
                85                  90                  95 ctc gag gct gaa gat ttc gca gtg tat tac tgt cat cag agt agt cgt       336
Leu Glu Ala Glu Asp Phe Ala Val Tyr Tyr Cys His Gln Ser Ser Arg
            100                 105                 110 tta cct cac act ttc ggc caa ggg acc aag gtg gag atc aaa cgt acg       384
Leu Pro His Thr Phe Gly Gln Gly Thr Lys Val Glu Ile Lys Arg Thr
        115                 120                 125

<210> SEQ ID NO 41
<211> LENGTH: 128
<212> TYPE: PRT
<213> ORGANISM: Homo sapiens

<400> SEQUENCE: 41

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Asp Ser Leu Ser Val
            20                  25                  30

Thr Pro Gly Glu Arg Val Thr Ile Thr Cys Arg Ala Ser Gln Ser Ile
        35                  40                  45

Gly Ser Ser Leu His Trp Tyr Gln Gln Lys Pro Gly Gln Ser Pro Lys
    50                  55                  60

Leu Leu Ile Tyr Tyr Ala Ser Gln Ser Leu Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Glu Ala Glu Asp Phe Ala Val Tyr Tyr Cys His Gln Ser Ser Arg
            100                 105                 110

Leu Pro His Thr Phe Gly Gln Gly Thr Lys Val Glu Ile Lys Arg Thr
        115                 120                 125

<210> SEQ ID NO 42
<211> LENGTH: 384
<212> TYPE: DNA
<213> ORGANISM: Homo sapiens
<220> FEATURE:
<221> NAME/KEY: CDS
<222> LOCATION: (1)..(384)
<223> OTHER INFORMATION:

<400> SEQUENCE: 42 atg tcg cca tca caa ctc att ggg ttt ctg ctg ctc tgg gtt cca gcc        48
Met Ser Pro Ser Gln Leu Ile Gly Phe Leu Leu Leu Trp Val Pro Ala
1               5                   10                  15
```

```
tcc agg ggt gaa att gtg ctg act cag agc cca ggt acc ctg tct gtg        96
Ser Arg Gly Glu Ile Val Leu Thr Gln Ser Pro Gly Thr Leu Ser Val
        20                  25                  30 tct cca ggc gag aga gcc acc ctc tcc tgc cgg gcc agt cag agc att       144
Ser Pro Gly Glu Arg Ala Thr Leu Ser Cys Arg Ala Ser Gln Ser Ile
    35                  40                  45 ggt agt agc tta cac tgg tac cag cag aaa cca ggt cag gct cca agg       192
Gly Ser Ser Leu His Trp Tyr Gln Gln Lys Pro Gly Gln Ala Pro Arg
50                  55                  60 ctt ctc atc tac tat gct tcc cag tcc ctc tca ggg atc ccc gat agg       240
Leu Leu Ile Tyr Tyr Ala Ser Gln Ser Leu Ser Gly Ile Pro Asp Arg
65                  70                  75                  80 ttc agt ggc agt gga tct ggg aca gat ttc acc ctc acc atc agt aga       288
Phe Ser Gly Ser Gly Ser Gly Thr Asp Phe Thr Leu Thr Ile Ser Arg
                85                  90                  95 ctg gag cct gaa gat ttc gca gtg tat tac tgt cat cag agt agt cgt       336
Leu Glu Pro Glu Asp Phe Ala Val Tyr Tyr Cys His Gln Ser Ser Arg
            100                 105                 110 tta cct cac act ttc ggc caa ggg acc aag gtg gag atc aaa cgt aca       384
Leu Pro His Thr Phe Gly Gln Gly Thr Lys Val Glu Ile Lys Arg Thr
        115                 120                 125

<210> SEQ ID NO 43
<211> LENGTH: 128
<212> TYPE: PRT
<213> ORGANISM: Homo sapiens

<400> SEQUENCE: 43

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Gly Thr Leu Ser Val
            20                  25                  30

Ser Pro Gly Glu Arg Ala Thr Leu Ser Cys Arg Ala Ser Gln Ser Ile
        35                  40                  45

Gly Ser Ser Leu His Trp Tyr Gln Gln Lys Pro Gly Gln Ala Pro Arg
    50                  55                  60

Leu Leu Ile Tyr Tyr Ala Ser Gln Ser Leu Ser Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys His Gln Ser Ser Arg
            100                 105                 110

Leu Pro His Thr Phe Gly Gln Gly Thr Lys Val Glu Ile Lys Arg Thr
        115                 120                 125

<210> SEQ ID NO 44
<211> LENGTH: 411
<212> TYPE: DNA
<213> ORGANISM: Homo sapiens
<220> FEATURE:
<221> NAME/KEY: CDS
<222> LOCATION: (1)..(411)
<223> OTHER INFORMATION:

<400> SEQUENCE: 44 atg gag ttt ggg ctg agc tgg gtt ttc ctt gtt gct ata tta aaa ggt        48
Met Glu Phe Gly Leu Ser Trp Val Phe Leu Val Ala Ile Leu Lys Gly
1               5                   10                  15 gtc cag tgt gag gtt cag ctg gtg cag tct ggg gga ggc ttg gta aag        96
Val Gln Cys Glu Val Gln Leu Val Gln Ser Gly Gly Gly Leu Val Lys
            20                  25                  30
```

```
cct ggg gga tcc ctg aga ctc tcc tgt gca gcc tct gga ttc acc ttc      144
Pro Gly Gly Ser Leu Arg Leu Ser Cys Ala Ala Ser Gly Phe Thr Phe
            35                  40                  45 agt agc ttt gct atg cac tgg gtt cgc cag gct cca gga aaa ggt ctg      192
Ser Ser Phe Ala Met His Trp Val Arg Gln Ala Pro Gly Lys Gly Leu
 50                  55                  60 gag tgg ata tca gtt att gat act cgt ggt gcc aca tac tat gca gac      240
Glu Trp Ile Ser Val Ile Asp Thr Arg Gly Ala Thr Tyr Tyr Ala Asp
 65                  70                  75                  80 tcc gtg aag ggc cga ttc acc atc tcc aga gac aat gcc aag aac tcc      288
Ser Val Lys Gly Arg Phe Thr Ile Ser Arg Asp Asn Ala Lys Asn Ser
                 85                  90                  95 ttg tat ctt caa atg aac agc ctg aga gcc gag gac act gct gtg tat      336
Leu Tyr Leu Gln Met Asn Ser Leu Arg Ala Glu Asp Thr Ala Val Tyr
            100                 105                 110 tac tgt gca aga ctg ggg aac ttc tac tac ggt atg gac gtc tgg ggc      384
Tyr Cys Ala Arg Leu Gly Asn Phe Tyr Tyr Gly Met Asp Val Trp Gly
            115                 120                 125 caa ggg acc acg gtc acc gtc tcc tca                                  411
Gln Gly Thr Thr Val Thr Val Ser Ser
130                 135
```

<210> SEQ ID NO 45
<211> LENGTH: 137
<212> TYPE: PRT
<213> ORGANISM: Homo sapiens

<400> SEQUENCE: 45

```
Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
 50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
    130                 135
```

<210> SEQ ID NO 46
<211> LENGTH: 69
<212> TYPE: DNA
<213> ORGANISM: Homo sapiens
<220> FEATURE:
<221> NAME/KEY: CDS
<222> LOCATION: (1)..(69)
<223> OTHER INFORMATION:

<400> SEQUENCE: 46

```
gaa att gtg ctg act cag agc cca gac tct ctg tct gtg act cca ggc      48
Glu Ile Val Leu Thr Gln Ser Pro Asp Ser Leu Ser Val Thr Pro Gly
1               5                   10                  15
```

```
gag aga gtc acc atc acc tgc                              69
Glu Arg Val Thr Ile Thr Cys
         20

<210> SEQ ID NO 47
<211> LENGTH: 23
<212> TYPE: PRT
<213> ORGANISM: Homo sapiens

<400> SEQUENCE: 47

Glu Ile Val Leu Thr Gln Ser Pro Asp Ser Leu Ser Val Thr Pro Gly
1               5                   10                  15

Glu Arg Val Thr Ile Thr Cys
         20

<210> SEQ ID NO 48
<211> LENGTH: 45
<212> TYPE: DNA
<213> ORGANISM: Homo sapiens
<220> FEATURE:
<221> NAME/KEY: CDS
<222> LOCATION: (1)..(45)
<223> OTHER INFORMATION:

<400> SEQUENCE: 48 tgg tac cag cag aaa cca ggt cag tct cca aag ctt ctc atc tac       45
Trp Tyr Gln Gln Lys Pro Gly Gln Ser Pro Lys Leu Leu Ile Tyr
1               5                   10                  15

<210> SEQ ID NO 49
<211> LENGTH: 15
<212> TYPE: PRT
<213> ORGANISM: Homo sapiens

<400> SEQUENCE: 49

Trp Tyr Gln Gln Lys Pro Gly Gln Ser Pro Lys Leu Leu Ile Tyr
1               5                   10                  15

<210> SEQ ID NO 50
<211> LENGTH: 96
<212> TYPE: DNA
<213> ORGANISM: Homo sapiens
<220> FEATURE:
<221> NAME/KEY: CDS
<222> LOCATION: (1)..(96)
<223> OTHER INFORMATION:

<400> SEQUENCE: 50 ggg gtc ccc tcg agg ttc agt ggc agt gga tct ggg aca gat ttc acc   48
Gly Val Pro Ser Arg Phe Ser Gly Ser Gly Ser Gly Thr Asp Phe Thr
1               5                   10                  15 ctc acc atc agt agc ctc gag gct gaa gat ttc gca gtg tat tac tgt   96
Leu Thr Ile Ser Ser Leu Glu Ala Glu Asp Phe Ala Val Tyr Tyr Cys
         20                  25                  30

<210> SEQ ID NO 51
<211> LENGTH: 32
<212> TYPE: PRT
<213> ORGANISM: Homo sapiens

<400> SEQUENCE: 51

Gly Val Pro Ser Arg Phe Ser Gly Ser Gly Ser Gly Thr Asp Phe Thr
1               5                   10                  15

Leu Thr Ile Ser Ser Leu Glu Ala Glu Asp Phe Ala Val Tyr Tyr Cys
         20                  25                  30
```

<210> SEQ ID NO 52
<211> LENGTH: 36
<212> TYPE: DNA
<213> ORGANISM: Homo sapiens
<220> FEATURE:
<221> NAME/KEY: CDS
<222> LOCATION: (1)..(36)
<223> OTHER INFORMATION:

<400> SEQUENCE: 52 ttc ggc caa ggg acc aag gtg gag atc aaa cgt acg      36
Phe Gly Gln Gly Thr Lys Val Glu Ile Lys Arg Thr
1               5                   10

<210> SEQ ID NO 53
<211> LENGTH: 12
<212> TYPE: PRT
<213> ORGANISM: Homo sapiens

<400> SEQUENCE: 53

Phe Gly Gln Gly Thr Lys Val Glu Ile Lys Arg Thr
1               5                   10

<210> SEQ ID NO 54
<211> LENGTH: 69
<212> TYPE: DNA
<213> ORGANISM: Homo sapiens
<220> FEATURE:
<221> NAME/KEY: CDS
<222> LOCATION: (1)..(69)
<223> OTHER INFORMATION:

<400> SEQUENCE: 54 gaa att gtg ctg act cag agc cca ggt acc ctg tct gtg tct cca ggc      48
Glu Ile Val Leu Thr Gln Ser Pro Gly Thr Leu Ser Val Ser Pro Gly
1               5                   10                  15 gag aga gcc acc ctc tcc tgc                                          69
Glu Arg Ala Thr Leu Ser Cys
            20

<210> SEQ ID NO 55
<211> LENGTH: 23
<212> TYPE: PRT
<213> ORGANISM: Homo sapiens

<400> SEQUENCE: 55

Glu Ile Val Leu Thr Gln Ser Pro Gly Thr Leu Ser Val Ser Pro Gly
1               5                   10                  15

Glu Arg Ala Thr Leu Ser Cys
            20

<210> SEQ ID NO 56
<211> LENGTH: 45
<212> TYPE: DNA
<213> ORGANISM: Homo sapiens
<220> FEATURE:
<221> NAME/KEY: CDS
<222> LOCATION: (1)..(45)
<223> OTHER INFORMATION:

<400> SEQUENCE: 56 tgg tac cag cag aaa cca ggt cag gct cca agg ctt ctc atc tac      45
Trp Tyr Gln Gln Lys Pro Gly Gln Ala Pro Arg Leu Leu Ile Tyr
1               5                   10                  15

<210> SEQ ID NO 57
<211> LENGTH: 15
<212> TYPE: PRT
<213> ORGANISM: Homo sapiens

<400> SEQUENCE: 57

Trp Tyr Gln Gln Lys Pro Gly Gln Ala Pro Arg Leu Leu Ile Tyr
1               5                   10                  15

<210> SEQ ID NO 58
<211> LENGTH: 96
<212> TYPE: DNA
<213> ORGANISM: Homo sapiens
<220> FEATURE:
<221> NAME/KEY: CDS
<222> LOCATION: (1)..(96)
<223> OTHER INFORMATION:

<400> SEQUENCE: 58 ggg atc ccc gat agg ttc agt ggc agt gga tct ggg aca gat ttc acc      48
Gly Ile Pro Asp Arg Phe Ser Gly Ser Gly Ser Gly Thr Asp Phe Thr
1               5                   10                  15 ctc acc atc agt aga ctg gag cct gaa gat ttc gca gtg tat tac tgt      96
Leu Thr Ile Ser Arg Leu Glu Pro Glu Asp Phe Ala Val Tyr Tyr Cys
            20                  25                  30

<210> SEQ ID NO 59
<211> LENGTH: 32
<212> TYPE: PRT
<213> ORGANISM: Homo sapiens

<400> SEQUENCE: 59

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 60
<211> LENGTH: 36
<212> TYPE: DNA
<213> ORGANISM: Homo sapiens
<220> FEATURE:
<221> NAME/KEY: CDS
<222> LOCATION: (1)..(36)
<223> OTHER INFORMATION:

<400> SEQUENCE: 60 ttc ggc caa ggg acc aag gtg gag atc aaa cgt aca                      36
Phe Gly Gln Gly Thr Lys Val Glu Ile Lys Arg Thr
1               5                   10

<210> SEQ ID NO 61
<211> LENGTH: 12
<212> TYPE: PRT
<213> ORGANISM: Homo sapiens

<400> SEQUENCE: 61

Phe Gly Gln Gly Thr Lys Val Glu Ile Lys Arg Thr
1               5                   10

<210> SEQ ID NO 62
<211> LENGTH: 90
<212> TYPE: DNA
<213> ORGANISM: Homo sapiens
<220> FEATURE:
<221> NAME/KEY: CDS
<222> LOCATION: (1)..(90)

<223> OTHER INFORMATION:

<400> SEQUENCE: 62

```
gag gtt cag ctg gtg cag tct ggg gga ggc ttg gta aag cct ggg ggg      48
Glu Val Gln Leu Val Gln Ser Gly Gly Gly Leu Val Lys Pro Gly Gly
1               5                   10                  15 tcc ctg aga ctc tcc tgt gca gcc tct gga ttc acc ttc agt              90
Ser Leu Arg Leu Ser Cys Ala Ala Ser Gly Phe Thr Phe Ser
            20                  25                  30
```

<210> SEQ ID NO 63
<211> LENGTH: 30
<212> TYPE: PRT
<213> ORGANISM: Homo sapiens

<400> SEQUENCE: 63

```
Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30
```

<210> SEQ ID NO 64
<211> LENGTH: 42
<212> TYPE: DNA
<213> ORGANISM: Homo sapiens
<220> FEATURE:
<221> NAME/KEY: CDS
<222> LOCATION: (1)..(42)
<223> OTHER INFORMATION:

<400> SEQUENCE: 64

```
tgg gtt cgc cag gct cca gga aaa ggt ctg gag tgg ata tca              42
Trp Val Arg Gln Ala Pro Gly Lys Gly Leu Glu Trp Ile Ser
1               5                   10
```

<210> SEQ ID NO 65
<211> LENGTH: 14
<212> TYPE: PRT
<213> ORGANISM: Homo sapiens

<400> SEQUENCE: 65

```
Trp Val Arg Gln Ala Pro Gly Lys Gly Leu Glu Trp Ile Ser
1               5                   10
```

<210> SEQ ID NO 66
<211> LENGTH: 96
<212> TYPE: DNA
<213> ORGANISM: Homo sapiens
<220> FEATURE:
<221> NAME/KEY: CDS
<222> LOCATION: (1)..(96)
<223> OTHER INFORMATION:

<400> SEQUENCE: 66

```
cga ttc acc atc tcc aga gac aat gcc aag aac tcc ttg tat ctt caa      48
Arg Phe Thr Ile Ser Arg Asp Asn Ala Lys Asn Ser Leu Tyr Leu Gln
1               5                   10                  15 atg aac agc ctg aga gcc gag gac act gct gtg tat tac tgt gca aga      96
Met Asn Ser Leu Arg Ala Glu Asp Thr Ala Val Tyr Tyr Cys Ala Arg
            20                  25                  30
```

<210> SEQ ID NO 67
<211> LENGTH: 32
<212> TYPE: PRT
<213> ORGANISM: Homo sapiens

<400> SEQUENCE: 67

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 68
<211> LENGTH: 33
<212> TYPE: DNA
<213> ORGANISM: Homo sapiens
<220> FEATURE:
<221> NAME/KEY: CDS
<222> LOCATION: (1)..(33)
<223> OTHER INFORMATION:

<400> SEQUENCE: 68 tgg ggc caa ggg acc acg gtc acc gtc tcc tca                      33
Trp Gly Gln Gly Thr Thr Val Thr Val Ser Ser
1               5                   10

<210> SEQ ID NO 69
<211> LENGTH: 11
<212> TYPE: PRT
<213> ORGANISM: Homo sapiens

<400> SEQUENCE: 69

Trp Gly Gln Gly Thr Thr Val Thr Val Ser Ser
1               5                   10

<210> SEQ ID NO 70
<211> LENGTH: 5
<212> TYPE: PRT
<213> ORGANISM: Homo sapiens

<400> SEQUENCE: 70

Asn Tyr Ala Met His
1               5

<210> SEQ ID NO 71
<211> LENGTH: 384
<212> TYPE: DNA
<213> ORGANISM: Homo sapiens
<220> FEATURE:
<221> NAME/KEY: CDS
<222> LOCATION: (1)..(384)
<223> OTHER INFORMATION:

<400> SEQUENCE: 71 atg tcg cca tca caa ctc att ggg ttt ctg ctg ctc tgg gtt cca gcc   48
Met Ser Pro Ser Gln Leu Ile Gly Phe Leu Leu Leu Trp Val Pro Ala
1               5                   10                  15 tcc agg ggt gaa att gtg ctg act cag agc cca gac tct ctg tct gtg   96
Ser Arg Gly Glu Ile Val Leu Thr Gln Ser Pro Asp Ser Leu Ser Val
            20                  25                  30 act cca ggc gag aga gtc acc atc acc tgc cgg gcc agt cag agc att  144
Thr Pro Gly Glu Arg Val Thr Ile Thr Cys Arg Ala Ser Gln Ser Ile
        35                  40                  45 ggt agt agc tta cac tgg tac cag cag aaa cca ggt cag tct cca aag  192
Gly Ser Ser Leu His Trp Tyr Gln Gln Lys Pro Gly Gln Ser Pro Lys
    50                  55                  60 ctt ctc atc aag tat gca tcc cag tcc ctc tca ggg gtc ccc tcg agg  240
Leu Leu Ile Lys Tyr Ala Ser Gln Ser Leu Ser Gly Val Pro Ser Arg
65                  70                  75                  80 ttc agt ggc agt gga tct ggg aca gat ttc acc ctc acc atc agt agc  288

```
Phe Ser Gly Ser Gly Ser Gly Thr Asp Phe Thr Leu Thr Ile Ser Ser
            85                  90                  95 ctc gag gct gaa gat gct gca gcg tat tac tgt cat cag agt agt cgt      336
Leu Glu Ala Glu Asp Ala Ala Ala Tyr Tyr Cys His Gln Ser Ser Arg
        100                 105                 110 tta cct cac act ttc ggc caa ggg acc aag gtg gag atc aaa cgt acg      384
Leu Pro His Thr Phe Gly Gln Gly Thr Lys Val Glu Ile Lys Arg Thr
        115                 120                 125
```

```
<210> SEQ ID NO 72
<211> LENGTH: 128
<212> TYPE: PRT
<213> ORGANISM: Homo sapiens

<400> SEQUENCE: 72

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Asp Ser Leu Ser Val
            20                  25                  30

Thr Pro Gly Glu Arg Val Thr Ile Thr Cys Arg Ala Ser Gln Ser Ile
        35                  40                  45

Gly Ser Ser Leu His Trp Tyr Gln Gln Lys Pro Gly Gln Ser Pro Lys
    50                  55                  60

Leu Leu Ile Lys Tyr Ala Ser Gln Ser Leu Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Glu Ala Glu Asp Ala Ala Ala Tyr Tyr Cys His Gln Ser Ser Arg
            100                 105                 110

Leu Pro His Thr Phe Gly Gln Gly Thr Lys Val Glu Ile Lys Arg Thr
        115                 120                 125
```

```
<210> SEQ ID NO 73
<211> LENGTH: 384
<212> TYPE: DNA
<213> ORGANISM: Homo sapiens
<220> FEATURE:
<221> NAME/KEY: CDS
<222> LOCATION: (1)..(384)
<223> OTHER INFORMATION:

<400> SEQUENCE: 73 atg tcg cca tca caa ctc att ggg ttt ctg ctg ctc tgg gtt cca gcc      48
Met Ser Pro Ser Gln Leu Ile Gly Phe Leu Leu Leu Trp Val Pro Ala
1               5                   10                  15 tcc agg ggt gaa att gtg ctg act cag agc cca gac tct ctg tct gtg      96
Ser Arg Gly Glu Ile Val Leu Thr Gln Ser Pro Asp Ser Leu Ser Val
            20                  25                  30 act cca ggc gag aga gtc acc atc acc tgc cgg gcc agt cag agc att      144
Thr Pro Gly Glu Arg Val Thr Ile Thr Cys Arg Ala Ser Gln Ser Ile
        35                  40                  45 ggt agt agc tta cac tgg tac cag cag aaa cca ggt cag tct cca aag      192
Gly Ser Ser Leu His Trp Tyr Gln Gln Lys Pro Gly Gln Ser Pro Lys
    50                  55                  60 ctt ctc atc aag tat gca tcc cag tcc ctc tca ggg gtc ccc tcg agg      240
Leu Leu Ile Lys Tyr Ala Ser Gln Ser Leu Ser Gly Val Pro Ser Arg
65                  70                  75                  80 ttc agt ggc agt gga tct ggg aca gat ttc acc ctc acc atc agt agc      288
Phe Ser Gly Ser Gly Ser Gly Thr Asp Phe Thr Leu Thr Ile Ser Ser
                85                  90                  95
```

```
ctc gag gct gaa gat ttc gca gtg tat tac tgt cat cag agt agt cgt    336
Leu Glu Ala Glu Asp Phe Ala Val Tyr Tyr Cys His Gln Ser Ser Arg
            100                 105                 110 tta cct cac act ttc ggc caa ggg acc aag gtg gag atc aaa cgt acg    384
Leu Pro His Thr Phe Gly Gln Gly Thr Lys Val Glu Ile Lys Arg Thr
        115                 120                 125
```

<210> SEQ ID NO 74
<211> LENGTH: 128
<212> TYPE: PRT
<213> ORGANISM: Homo sapiens

<400> SEQUENCE: 74

```
Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Asp Ser Leu Ser Val
            20                  25                  30

Thr Pro Gly Glu Arg Val Thr Ile Thr Cys Arg Ala Ser Gln Ser Ile
        35                  40                  45

Gly Ser Ser Leu His Trp Tyr Gln Gln Lys Pro Gly Gln Ser Pro Lys
    50                  55                  60

Leu Leu Ile Lys Tyr Ala Ser Gln Ser Leu Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Glu Ala Glu Asp Phe Ala Val Tyr Tyr Cys His Gln Ser Ser Arg
            100                 105                 110

Leu Pro His Thr Phe Gly Gln Gly Thr Lys Val Glu Ile Lys Arg Thr
        115                 120                 125
```

<210> SEQ ID NO 75
<211> LENGTH: 384
<212> TYPE: DNA
<213> ORGANISM: Homo sapiens
<220> FEATURE:
<221> NAME/KEY: CDS
<222> LOCATION: (1)..(384)
<223> OTHER INFORMATION:

<400> SEQUENCE: 75

```
atg tcg cca tca caa ctc att ggg ttt ctg ctg ctc tgg gtt cca gcc    48
Met Ser Pro Ser Gln Leu Ile Gly Phe Leu Leu Leu Trp Val Pro Ala
1               5                   10                  15 tcc agg ggt gaa att gtg ctg act cag agc cca ggt acc ctg tct gtg    96
Ser Arg Gly Glu Ile Val Leu Thr Gln Ser Pro Gly Thr Leu Ser Val
            20                  25                  30 tct cca ggc gag aga gcc acc ctc tcc tgc cgg gcc agt cag agc att    144
Ser Pro Gly Glu Arg Ala Thr Leu Ser Cys Arg Ala Ser Gln Ser Ile
        35                  40                  45 ggt agt agc tta cac tgg tac cag cag aaa cca ggt cag gct cca agg    192
Gly Ser Ser Leu His Trp Tyr Gln Gln Lys Pro Gly Gln Ala Pro Arg
    50                  55                  60 ctt ctc atc aag tat gca tcc cag tcc ctc tca ggg atc ccc gat agg    240
Leu Leu Ile Lys Tyr Ala Ser Gln Ser Leu Ser Gly Ile Pro Asp Arg
65                  70                  75                  80 ttc agt ggc agt gga tct ggg aca gat ttc acc ctc acc atc agt aga    288
Phe Ser Gly Ser Gly Ser Gly Thr Asp Phe Thr Leu Thr Ile Ser Arg
                85                  90                  95 ctg gag cct gaa gat gct gca gcg tat tac tgt cat cag agt agt cgt    336
Leu Glu Pro Glu Asp Ala Ala Ala Tyr Tyr Cys His Gln Ser Ser Arg
            100                 105                 110
```

```
tta cct cac act ttc ggc caa ggg acc aag gtg gag atc aaa cgt aca        384
Leu Pro His Thr Phe Gly Gln Gly Thr Lys Val Glu Ile Lys Arg Thr
        115                 120                 125

<210> SEQ ID NO 76
<211> LENGTH: 128
<212> TYPE: PRT
<213> ORGANISM: Homo sapiens

<400> SEQUENCE: 76

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Gly Thr Leu Ser Val
            20                  25                  30

Ser Pro Gly Glu Arg Ala Thr Leu Ser Cys Arg Ala Ser Gln Ser Ile
        35                  40                  45

Gly Ser Ser Leu His Trp Tyr Gln Gln Lys Pro Gly Gln Ala Pro Arg
    50                  55                  60

Leu Leu Ile Lys Tyr Ala Ser Gln Ser Leu Ser Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Ala Ala Tyr Tyr Cys His Gln Ser Ser Arg
            100                 105                 110

Leu Pro His Thr Phe Gly Gln Gly Thr Lys Val Glu Ile Lys Arg Thr
        115                 120                 125

<210> SEQ ID NO 77
<211> LENGTH: 384
<212> TYPE: DNA
<213> ORGANISM: Homo sapiens
<220> FEATURE:
<221> NAME/KEY: CDS
<222> LOCATION: (1)..(384)
<223> OTHER INFORMATION:

<400> SEQUENCE: 77 atg tcg cca tca caa ctc att ggg ttt ctg ctg ctc tgg gtt cca gcc        48
Met Ser Pro Ser Gln Leu Ile Gly Phe Leu Leu Leu Trp Val Pro Ala
1               5                   10                  15 tcc agg ggt gaa att gtg ctg act cag agc cca ggt acc ctg tct gtg        96
Ser Arg Gly Glu Ile Val Leu Thr Gln Ser Pro Gly Thr Leu Ser Val
            20                  25                  30 tct cca ggc gag aga gcc acc ctc tcc tgc cgg gcc agt cag agc att       144
Ser Pro Gly Glu Arg Ala Thr Leu Ser Cys Arg Ala Ser Gln Ser Ile
        35                  40                  45 ggt agt agc tta cac tgg tac cag cag aaa cca ggt cag gct cca agg       192
Gly Ser Ser Leu His Trp Tyr Gln Gln Lys Pro Gly Gln Ala Pro Arg
    50                  55                  60 ctt ctc atc aag tat gca tcc cag tcc ctc tca ggg atc ccc gat agg       240
Leu Leu Ile Lys Tyr Ala Ser Gln Ser Leu Ser Gly Ile Pro Asp Arg
65                  70                  75                  80 ttc agt ggc agt gga tct ggg aca gat ttc acc ctc acc atc agt aga       288
Phe Ser Gly Ser Gly Ser Gly Thr Asp Phe Thr Leu Thr Ile Ser Arg
                85                  90                  95 ctg gag cct gaa gat ttc gca gtg tat tac tgt cat cag agt agt cgt       336
Leu Glu Pro Glu Asp Phe Ala Val Tyr Tyr Cys His Gln Ser Ser Arg
            100                 105                 110 tta cct cac act ttc ggc caa ggg acc aag gtg gag atc aaa cgt aca       384
Leu Pro His Thr Phe Gly Gln Gly Thr Lys Val Glu Ile Lys Arg Thr
```

<210> SEQ ID NO 78
<211> LENGTH: 128
<212> TYPE: PRT
<213> ORGANISM: Homo sapiens

<400> SEQUENCE: 78

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Gly Thr Leu Ser Val
            20                  25                  30

Ser Pro Gly Glu Arg Ala Thr Leu Ser Cys Arg Ala Ser Gln Ser Ile
        35                  40                  45

Gly Ser Ser Leu His Trp Tyr Gln Gln Lys Pro Gly Gln Ala Pro Arg
    50                  55                  60

Leu Leu Ile Lys Tyr Ala Ser Gln Ser Leu Ser Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys His Gln Ser Ser Arg
            100                 105                 110

Leu Pro His Thr Phe Gly Gln Gly Thr Lys Val Glu Ile Lys Arg Thr
        115                 120                 125

<210> SEQ ID NO 79
<211> LENGTH: 69
<212> TYPE: DNA
<213> ORGANISM: Homo sapiens
<220> FEATURE:
<221> NAME/KEY: CDS
<222> LOCATION: (1)..(69)
<223> OTHER INFORMATION:

<400> SEQUENCE: 79 gaa att gtg ctg act cag agc cca gac tct ctg tct gtg act cca ggc    48
Glu Ile Val Leu Thr Gln Ser Pro Asp Ser Leu Ser Val Thr Pro Gly
1               5                   10                  15 gag aga gtc acc atc acc tgc                                        69
Glu Arg Val Thr Ile Thr Cys
            20

<210> SEQ ID NO 80
<211> LENGTH: 23
<212> TYPE: PRT
<213> ORGANISM: Homo sapiens

<400> SEQUENCE: 80

Glu Ile Val Leu Thr Gln Ser Pro Asp Ser Leu Ser Val Thr Pro Gly
1               5                   10                  15

Glu Arg Val Thr Ile Thr Cys
            20

<210> SEQ ID NO 81
<211> LENGTH: 45
<212> TYPE: DNA
<213> ORGANISM: Homo sapiens
<220> FEATURE:
<221> NAME/KEY: CDS
<222> LOCATION: (1)..(45)
<223> OTHER INFORMATION:

<400> SEQUENCE: 81

```
tgg tac cag cag aaa cca ggt cag tct cca aag ctt ctc atc aag      45
Trp Tyr Gln Gln Lys Pro Gly Gln Ser Pro Lys Leu Leu Ile Lys
1               5                   10                  15
```

<210> SEQ ID NO 82
<211> LENGTH: 15
<212> TYPE: PRT
<213> ORGANISM: Homo sapiens

<400> SEQUENCE: 82

```
Trp Tyr Gln Gln Lys Pro Gly Gln Ser Pro Lys Leu Leu Ile Lys
1               5                   10                  15
```

<210> SEQ ID NO 83
<211> LENGTH: 96
<212> TYPE: DNA
<213> ORGANISM: Homo sapiens
<220> FEATURE:
<221> NAME/KEY: CDS
<222> LOCATION: (1)..(96)
<223> OTHER INFORMATION:

<400> SEQUENCE: 83

```
ggg gtc ccc tcg agg ttc agt ggc agt gga tct ggg aca gat ttc acc      48
Gly Val Pro Ser Arg Phe Ser Gly Ser Gly Ser Gly Thr Asp Phe Thr
1               5                   10                  15 ctc acc atc agt agc ctc gag gct gaa gat gct gca gcg tat tac tgt      96
Leu Thr Ile Ser Ser Leu Glu Ala Glu Asp Ala Ala Ala Tyr Tyr Cys
            20                  25                  30
```

<210> SEQ ID NO 84
<211> LENGTH: 32
<212> TYPE: PRT
<213> ORGANISM: Homo sapiens

<400> SEQUENCE: 84

```
Gly Val Pro Ser Arg Phe Ser Gly Ser Gly Ser Gly Thr Asp Phe Thr
1               5                   10                  15

Leu Thr Ile Ser Ser Leu Glu Ala Glu Asp Ala Ala Ala Tyr Tyr Cys
            20                  25                  30
```

<210> SEQ ID NO 85
<211> LENGTH: 36
<212> TYPE: DNA
<213> ORGANISM: Homo sapiens
<220> FEATURE:
<221> NAME/KEY: CDS
<222> LOCATION: (1)..(36)
<223> OTHER INFORMATION:

<400> SEQUENCE: 85

```
ttc ggc caa ggg acc aag gtg gag atc aaa cgt acg                      36
Phe Gly Gln Gly Thr Lys Val Glu Ile Lys Arg Thr
1               5                   10
```

<210> SEQ ID NO 86
<211> LENGTH: 12
<212> TYPE: PRT
<213> ORGANISM: Homo sapiens

<400> SEQUENCE: 86

```
Phe Gly Gln Gly Thr Lys Val Glu Ile Lys Arg Thr
1               5                   10
```

<210> SEQ ID NO 87

```
<211> LENGTH: 69
<212> TYPE: DNA
<213> ORGANISM: Homo sapiens
<220> FEATURE:
<221> NAME/KEY: CDS
<222> LOCATION: (1)..(69)
<223> OTHER INFORMATION:

<400> SEQUENCE: 87 gaa att gtg ctg act cag agc cca gac tct ctg tct gtg act cca ggc      48
Glu Ile Val Leu Thr Gln Ser Pro Asp Ser Leu Ser Val Thr Pro Gly
1               5                   10                  15 gag aga gtc acc atc acc tgc                                          69
Glu Arg Val Thr Ile Thr Cys
            20

<210> SEQ ID NO 88
<211> LENGTH: 23
<212> TYPE: PRT
<213> ORGANISM: Homo sapiens

<400> SEQUENCE: 88

Glu Ile Val Leu Thr Gln Ser Pro Asp Ser Leu Ser Val Thr Pro Gly
1               5                   10                  15

Glu Arg Val Thr Ile Thr Cys
            20

<210> SEQ ID NO 89
<211> LENGTH: 45
<212> TYPE: DNA
<213> ORGANISM: Homo sapiens
<220> FEATURE:
<221> NAME/KEY: CDS
<222> LOCATION: (1)..(45)
<223> OTHER INFORMATION:

<400> SEQUENCE: 89 tgg tac cag cag aaa cca ggt cag tct cca aag ctt ctc atc aag          45
Trp Tyr Gln Gln Lys Pro Gly Gln Ser Pro Lys Leu Leu Ile Lys
1               5                   10                  15

<210> SEQ ID NO 90
<211> LENGTH: 15
<212> TYPE: PRT
<213> ORGANISM: Homo sapiens

<400> SEQUENCE: 90

Trp Tyr Gln Gln Lys Pro Gly Gln Ser Pro Lys Leu Leu Ile Lys
1               5                   10                  15

<210> SEQ ID NO 91
<211> LENGTH: 96
<212> TYPE: DNA
<213> ORGANISM: Homo sapiens
<220> FEATURE:
<221> NAME/KEY: CDS
<222> LOCATION: (1)..(96)
<223> OTHER INFORMATION:

<400> SEQUENCE: 91 ggg gtc ccc tcg agg ttc agt ggc agt gga tct ggg aca gat ttc acc      48
Gly Val Pro Ser Arg Phe Ser Gly Ser Gly Ser Gly Thr Asp Phe Thr
1               5                   10                  15 ctc acc atc agt agc ctc gag gct gaa gat ttc gca gtg tat tac tgt      96
Leu Thr Ile Ser Ser Leu Glu Ala Glu Asp Phe Ala Val Tyr Tyr Cys
            20                  25                  30
```

```
<210> SEQ ID NO 92
<211> LENGTH: 32
<212> TYPE: PRT
<213> ORGANISM: Homo sapiens

<400> SEQUENCE: 92

Gly Val Pro Ser Arg Phe Ser Gly Ser Gly Ser Gly Thr Asp Phe Thr
1               5                   10                  15

Leu Thr Ile Ser Ser Leu Glu Ala Glu Asp Phe Ala Val Tyr Tyr Cys
            20                  25                  30

<210> SEQ ID NO 93
<211> LENGTH: 36
<212> TYPE: DNA
<213> ORGANISM: Homo sapiens
<220> FEATURE:
<221> NAME/KEY: CDS
<222> LOCATION: (1)..(36)
<223> OTHER INFORMATION:

<400> SEQUENCE: 93 ttc ggc caa ggg acc aag gtg gag atc aaa cgt acg            36
Phe Gly Gln Gly Thr Lys Val Glu Ile Lys Arg Thr
1               5                   10

<210> SEQ ID NO 94
<211> LENGTH: 12
<212> TYPE: PRT
<213> ORGANISM: Homo sapiens

<400> SEQUENCE: 94

Phe Gly Gln Gly Thr Lys Val Glu Ile Lys Arg Thr
1               5                   10

<210> SEQ ID NO 95
<211> LENGTH: 69
<212> TYPE: DNA
<213> ORGANISM: Homo sapiens
<220> FEATURE:
<221> NAME/KEY: CDS
<222> LOCATION: (1)..(69)
<223> OTHER INFORMATION:

<400> SEQUENCE: 95 gaa att gtg ctg act cag agc cca ggt acc ctg tct gtg tct cca ggc     48
Glu Ile Val Leu Thr Gln Ser Pro Gly Thr Leu Ser Val Ser Pro Gly
1               5                   10                  15 gag aga gcc acc ctc tcc tgc                                         69
Glu Arg Ala Thr Leu Ser Cys
            20

<210> SEQ ID NO 96
<211> LENGTH: 23
<212> TYPE: PRT
<213> ORGANISM: Homo sapiens

<400> SEQUENCE: 96

Glu Ile Val Leu Thr Gln Ser Pro Gly Thr Leu Ser Val Ser Pro Gly
1               5                   10                  15

Glu Arg Ala Thr Leu Ser Cys
            20

<210> SEQ ID NO 97
<211> LENGTH: 45
<212> TYPE: DNA
```

```
<213> ORGANISM: Homo sapiens
<220> FEATURE:
<221> NAME/KEY: CDS
<222> LOCATION: (1)..(45)
<223> OTHER INFORMATION:

<400> SEQUENCE: 97 tgg tac cag cag aaa cca ggt cag gct cca agg ctt ctc atc aag        45
Trp Tyr Gln Gln Lys Pro Gly Gln Ala Pro Arg Leu Leu Ile Lys
1               5                  10                  15

<210> SEQ ID NO 98
<211> LENGTH: 15
<212> TYPE: PRT
<213> ORGANISM: Homo sapiens

<400> SEQUENCE: 98

Trp Tyr Gln Gln Lys Pro Gly Gln Ala Pro Arg Leu Leu Ile Lys
1               5                  10                  15

<210> SEQ ID NO 99
<211> LENGTH: 96
<212> TYPE: DNA
<213> ORGANISM: Homo sapiens
<220> FEATURE:
<221> NAME/KEY: CDS
<222> LOCATION: (1)..(96)
<223> OTHER INFORMATION:

<400> SEQUENCE: 99 ggg atc ccc gat agg ttc agt ggc agt gga tct ggg aca gat ttc acc    48
Gly Ile Pro Asp Arg Phe Ser Gly Ser Gly Ser Gly Thr Asp Phe Thr
1               5                  10                  15 ctc acc atc agt aga ctg gag cct gaa gat gct gca gcg tat tac tgt    96
Leu Thr Ile Ser Arg Leu Glu Pro Glu Asp Ala Ala Ala Tyr Tyr Cys
            20                  25                  30

<210> SEQ ID NO 100
<211> LENGTH: 32
<212> TYPE: PRT
<213> ORGANISM: Homo sapiens

<400> SEQUENCE: 100

Gly Ile Pro Asp Arg Phe Ser Gly Ser Gly Ser Gly Thr Asp Phe Thr
1               5                  10                  15

Leu Thr Ile Ser Arg Leu Glu Pro Glu Asp Ala Ala Ala Tyr Tyr Cys
            20                  25                  30

<210> SEQ ID NO 101
<211> LENGTH: 36
<212> TYPE: DNA
<213> ORGANISM: Homo sapiens
<220> FEATURE:
<221> NAME/KEY: CDS
<222> LOCATION: (1)..(36)
<223> OTHER INFORMATION:

<400> SEQUENCE: 101 ttc ggc caa ggg acc aag gtg gag atc aaa cgt aca                    36
Phe Gly Gln Gly Thr Lys Val Glu Ile Lys Arg Thr
1               5                  10

<210> SEQ ID NO 102
<211> LENGTH: 12
<212> TYPE: PRT
<213> ORGANISM: Homo sapiens
```

```
<400> SEQUENCE: 102

Phe Gly Gln Gly Thr Lys Val Glu Ile Lys Arg Thr
1               5                   10

<210> SEQ ID NO 103
<211> LENGTH: 69
<212> TYPE: DNA
<213> ORGANISM: Homo sapiens
<220> FEATURE:
<221> NAME/KEY: CDS
<222> LOCATION: (1)..(69)
<223> OTHER INFORMATION:

<400> SEQUENCE: 103 gaa att gtg ctg act cag agc cca ggt acc ctg tct gtg tct cca ggc      48
Glu Ile Val Leu Thr Gln Ser Pro Gly Thr Leu Ser Val Ser Pro Gly
1               5                   10                  15 gag aga gcc acc ctc tcc tgc                                          69
Glu Arg Ala Thr Leu Ser Cys
            20

<210> SEQ ID NO 104
<211> LENGTH: 23
<212> TYPE: PRT
<213> ORGANISM: Homo sapiens

<400> SEQUENCE: 104

Glu Ile Val Leu Thr Gln Ser Pro Gly Thr Leu Ser Val Ser Pro Gly
1               5                   10                  15

Glu Arg Ala Thr Leu Ser Cys
            20

<210> SEQ ID NO 105
<211> LENGTH: 45
<212> TYPE: DNA
<213> ORGANISM: Homo sapiens
<220> FEATURE:
<221> NAME/KEY: CDS
<222> LOCATION: (1)..(45)
<223> OTHER INFORMATION:

<400> SEQUENCE: 105 tgg tac cag cag aaa cca ggt cag gct cca agg ctt ctc atc aag          45
Trp Tyr Gln Gln Lys Pro Gly Gln Ala Pro Arg Leu Leu Ile Lys
1               5                   10                  15

<210> SEQ ID NO 106
<211> LENGTH: 15
<212> TYPE: PRT
<213> ORGANISM: Homo sapiens

<400> SEQUENCE: 106

Trp Tyr Gln Gln Lys Pro Gly Gln Ala Pro Arg Leu Leu Ile Lys
1               5                   10                  15

<210> SEQ ID NO 107
<211> LENGTH: 96
<212> TYPE: DNA
<213> ORGANISM: Homo sapiens
<220> FEATURE:
<221> NAME/KEY: CDS
<222> LOCATION: (1)..(96)
<223> OTHER INFORMATION:

<400> SEQUENCE: 107 ggg atc ccc gat agg ttc agt ggc agt gga tct ggg aca gat ttc acc      48
```

```
Gly Ile Pro Asp Arg Phe Ser Gly Ser Gly Ser Gly Thr Asp Phe Thr
1               5                   10                  15 ctc acc atc agt aga ctg gag cct gaa gat ttc gca gtg tat tac tgt        96
Leu Thr Ile Ser Arg Leu Glu Pro Glu Asp Phe Ala Val Tyr Tyr Cys
            20                  25                  30
```

<210> SEQ ID NO 108
<211> LENGTH: 32
<212> TYPE: PRT
<213> ORGANISM: Homo sapiens

<400> SEQUENCE: 108

```
Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30
```

<210> SEQ ID NO 109
<211> LENGTH: 36
<212> TYPE: DNA
<213> ORGANISM: Homo sapiens
<220> FEATURE:
<221> NAME/KEY: CDS
<222> LOCATION: (1)..(36)
<223> OTHER INFORMATION:

<400> SEQUENCE: 109

```
ttc ggc caa ggg acc aag gtg gag atc aaa cgt aca                        36
Phe Gly Gln Gly Thr Lys Val Glu Ile Lys Arg Thr
1               5                   10
```

<210> SEQ ID NO 110
<211> LENGTH: 12
<212> TYPE: PRT
<213> ORGANISM: Homo sapiens

<400> SEQUENCE: 110

```
Phe Gly Gln Gly Thr Lys Val Glu Ile Lys Arg Thr
1               5                   10
```

<210> SEQ ID NO 111
<211> LENGTH: 411
<212> TYPE: DNA
<213> ORGANISM: Homo sapiens
<220> FEATURE:
<221> NAME/KEY: CDS
<222> LOCATION: (1)..(411)
<223> OTHER INFORMATION:

<400> SEQUENCE: 111

```
atg gag ttt ggg ctg agc tgg gtt ttc ctt gtt gct ata tta aaa ggt        48
Met Glu Phe Gly Leu Ser Trp Val Phe Leu Val Ala Ile Leu Lys Gly
1               5                   10                  15 gtc cag tgt gag gtt cag ctg gtg cag tct ggg gga ggc ttg gta cag        96
Val Gln Cys Glu Val Gln Leu Val Gln Ser Gly Gly Gly Leu Val Gln
            20                  25                  30 ccc ggg ggg tcc ctg aga ctc tcc tgt gca gcc tct gga ttc acc ttc        144
Pro Gly Gly Ser Leu Arg Leu Ser Cys Ala Ala Ser Gly Phe Thr Phe
        35                  40                  45 agt agc ttt gct atg cac tgg gtt cgc cag gct cca gga aaa ggt ctg        192
Ser Ser Phe Ala Met His Trp Val Arg Gln Ala Pro Gly Lys Gly Leu
    50                  55                  60 gag tgg ata tca gtt att gat act cgt ggt gcc aca tac tat gca gac        240
Glu Trp Ile Ser Val Ile Asp Thr Arg Gly Ala Thr Tyr Tyr Ala Asp
65                  70                  75                  80
```

```
tcc gtg aag ggc cga ttc acc atc tcc aga gac aat gcc aag aac tcc     288
Ser Val Lys Gly Arg Phe Thr Ile Ser Arg Asp Asn Ala Lys Asn Ser
                85                  90                  95 ttg tat ctt caa atg aac agc ctg aga gcc gag gac act gct gtg tat     336
Leu Tyr Leu Gln Met Asn Ser Leu Arg Ala Glu Asp Thr Ala Val Tyr
            100                 105                 110 tac tgt gca aga ctg ggg aac ttc tac tac ggt atg gac gtc tgg ggc     384
Tyr Cys Ala Arg Leu Gly Asn Phe Tyr Tyr Gly Met Asp Val Trp Gly
        115                 120                 125 caa ggg acc acg gtc acc gtc tcc tca                                 411
Gln Gly Thr Thr Val Thr Val Ser Ser
    130                 135
```

<210> SEQ ID NO 112
<211> LENGTH: 137
<212> TYPE: PRT
<213> ORGANISM: Homo sapiens

<400> SEQUENCE: 112

```
Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
    50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
    130                 135
```

<210> SEQ ID NO 113
<211> LENGTH: 75
<212> TYPE: DNA
<213> ORGANISM: Homo sapiens
<220> FEATURE:
<221> NAME/KEY: CDS
<222> LOCATION: (1)..(75)
<223> OTHER INFORMATION:

<400> SEQUENCE: 113

```
gag gtt cag ctg gtg cag tct ggg gga ggc ttg gta cag cct ggg ggg     48
Glu Val Gln Leu Val Gln Ser Gly Gly Gly Leu Val Gln Pro Gly Gly
1               5                   10                  15 tcc ctg aga ctc tcc tgt gca gcc tct                                 75
Ser Leu Arg Leu Ser Cys Ala Ala Ser
            20                  25
```

<210> SEQ ID NO 114
<211> LENGTH: 25
<212> TYPE: PRT
<213> ORGANISM: Homo sapiens

<400> SEQUENCE: 114

```
Glu Val Gln Leu Val Gln Ser Gly Gly Gly Leu Val Gln Pro Gly Gly
1               5                   10                  15

Ser Leu Arg Leu Ser Cys Ala Ala Ser
            20                  25
```

<210> SEQ ID NO 115
<211> LENGTH: 42
<212> TYPE: DNA
<213> ORGANISM: Homo sapiens
<220> FEATURE:
<221> NAME/KEY: CDS
<222> LOCATION: (1)..(42)
<223> OTHER INFORMATION:

<400> SEQUENCE: 115

```
tgg gtt cgc cag gct cca gga aaa ggt ctg gag tgg ata tca        42
Trp Val Arg Gln Ala Pro Gly Lys Gly Leu Glu Trp Ile Ser
1               5                   10
```

<210> SEQ ID NO 116
<211> LENGTH: 14
<212> TYPE: PRT
<213> ORGANISM: Homo sapiens

<400> SEQUENCE: 116

```
Trp Val Arg Gln Ala Pro Gly Lys Gly Leu Glu Trp Ile Ser
1               5                   10
```

<210> SEQ ID NO 117
<211> LENGTH: 96
<212> TYPE: DNA
<213> ORGANISM: Homo sapiens
<220> FEATURE:
<221> NAME/KEY: CDS
<222> LOCATION: (1)..(96)
<223> OTHER INFORMATION:

<400> SEQUENCE: 117

```
cga ttc acc atc tcc aga gac aat gcc aag aac tcc ttg tat ctt caa    48
Arg Phe Thr Ile Ser Arg Asp Asn Ala Lys Asn Ser Leu Tyr Leu Gln
1               5                   10                  15 atg aac agc ctg aga gcc gag gac act gct gtg tat tac tgt gca aga    96
Met Asn Ser Leu Arg Ala Glu Asp Thr Ala Val Tyr Tyr Cys Ala Arg
            20                  25                  30
```

<210> SEQ ID NO 118
<211> LENGTH: 32
<212> TYPE: PRT
<213> ORGANISM: Homo sapiens

<400> SEQUENCE: 118

```
Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30
```

<210> SEQ ID NO 119
<211> LENGTH: 33
<212> TYPE: DNA
<213> ORGANISM: Homo sapiens
<220> FEATURE:
<221> NAME/KEY: CDS
<222> LOCATION: (1)..(33)
<223> OTHER INFORMATION:

<400> SEQUENCE: 119

```
tgg ggc caa ggg acc acg gtc acc gtc tcc tca                33
Trp Gly Gln Gly Thr Thr Val Thr Val Ser Ser
1               5                   10

<210> SEQ ID NO 120
<211> LENGTH: 11
<212> TYPE: PRT
<213> ORGANISM: Homo sapiens

<400> SEQUENCE: 120

Trp Gly Gln Gly Thr Thr Val Thr Val Ser Ser
1               5                   10
```

NEUTRALIZING HUMAN ANTI-IGFR ANTIBODY

This application is a divisional of U.S. patent application Ser. No. 10/443,466, filed May 22, 2003, now U.S. Pat. No. 7,217,796, which claims the benefit of U.S. Provisional Patent Application No. 60/383,459, filed May 24, 2002; U.S. Provisional Patent Application No. 60/393,214, filed Jul. 2, 2002 and U.S. Provisional Patent Application No. 60/436, 254, filed Dec. 23, 2002 each of which is herein incorporated by reference in its entirety.

FIELD OF THE INVENTION

The present invention relates to fully human, monoclonal anti-Insulin-like Growth Factor Receptor-I (IGFR1) antibodies as well as methods of using the antibodies and methods of producing the antibodies.

BACKGROUND OF THE INVENTION

The insulin-like growth factors, also known as somatomedins, include insulin-like growth factor-I (IGF-I) and insulin-like growth factor-II (IGF-II) (Klapper, et al., (1983) Endocrinol. 112:2215 and Rinderknecht, et al., (1978) Febs. Lett. 89:283). These growth factors exert mitogenic activity on various cell types, including tumor cells (Macaulay, (1992) Br. J. Cancer 65:311), by binding to a common receptor named the insulin-like growth factor receptor-1 (IGFR1) (Sepp-Lorenzino, (1998) Breast Cancer Research and Treatment 47:235). Interaction of IGFs with IGFR1 activates the receptor by triggering autophosphorylation of the receptor on tyrosine residues (Butler, et al., (1998) Comparative Biochemistry and Physiology 121:19). Once activated, IGFR1, in turn, phosphorylates intracellular targets to activate cellular signaling pathways. This receptor activation is critical for stimulation of tumor cell growth and survival. Therefore, inhibition of IGFR1 activity represents a valuable potential method to treat or prevent growth of human cancers and other proliferative diseases.

Several lines of evidence indicate that IGF-I, IGF-II and their receptor IGFR1 are important mediators of the malignant phenotype. Plasma levels of IGF-I have been found to be the strongest predictor of prostate cancer risk (Chan, et al., (1998) Science 279:563) and similar epidemiological studies strongly link plasma IGF-I levels with breast, colon and lung cancer risk.

Overexpression of Insulin-like Growth Factor Receptor-I has also been demonstrated in several cancer cell lines and tumor tissues. IGFR1 is overexpressed in 40% of all breast cancer cell lines (Pandini, et al., (1999) Cancer Res. 5:1935) and in 15% of lung cancer cell lines. In breast cancer tumor tissue, IGFR1 is overexpressed 6-14 fold and IGFR1 exhibits 2-4 fold higher kinase activity as compared to normal tissue (Webster, et al., (1996) Cancer Res. 56:2781 and Pekonen, et al., (1998) Cancer Res. 48:1343). Ninety percent of colorectal cancer tissue biopsies exhibit elevated IGFR1 levels wherein the extent of IGFR1 expression is correlated with the severity of the disease. Analysis of primary cervical cancer cell cultures and cervical cancer cell lines revealed 3- and 5-fold overexpression of IGFR1, respectively, as compared to normal ectocervical cells (Steller, et al., (1996) Cancer Res. 56:1762). Expression of IGFR1 in synovial sarcoma cells also correlated with an aggressive phenotype (i.e., metastasis and high rate of proliferation; Xie, et al., (1999) Cancer Res. 59:3588).

Acromegaly, a slowly developing disease, is caused by hypersecretion of growth hormone and IGF-I (Ben-Schlomo, et al., (2001) Endocrin. Metab. Clin. North. Am. 30:565-583). Antagonism of IGFR1 function may be helpful in treating the disease.

There are several antibodies, which are known in the art, which inhibit the activity of IGFR1. However, these are of relatively low therapeutic value. For example, α-IR3 (Kull, et al., (1983) J. Biol. Chem. 258:6561), 1H7 (Li et al., (1993) Biochem. Biophys. Res. Comm. 196.92-98 and Xiong et al., (1992) Proc. Natl. Acad. Sci., U.S.A. 89:5356-5360; Santa Cruz biotechnology, Inc.; Santa Cruz, Calif.) and MAB391 (R&D Systems; Minneapolis, Minn.) are mouse monoclonal antibodies which interact with IGFR1 and inhibit its activity. Since these are mouse antibodies, their therapeutic utility in humans is limited. When immunocompetent human subjects are administered a dose of mouse antibodies, the subjects produce antibodies against the mouse immunoglobulin sequences. These human anti-mouse antibodies (HAMA) neutralize the therapeutic antibodies and may induce acute toxicity (i.e., a HAMA response).

One method by which to avert a HAMA response is through the use of fully-human antibodies which lack any foreign (e.g., mouse) amino acid sequences. Although the use of fully-human antibodies is an effective method by which to reduce or prevent human host immune rejection of the therapeutic antibody, rejection of the fully-human antibody can occur. Human rejection of human antibodies may be referred to as a human anti-human antibody response (HAHA response). HAHA response can be mediated by factors such as the presence of rare, low occurrence amino acid sequences in the fully-human antibodies. For this reason, therapeutic antibodies may also be optimized by the inclusion of non-immunogenic or only weakly immunogenic human antibody framework sequences. Preferably, the sequences occur frequently in other human antibodies.

SUMMARY OF THE INVENTION

The present invention provides fully human anti-human IGFR1 monoclonal antibodies which, preferably, will not induce a HAMA response or will not induce a HAHA response when administered to human subjects and which are useful for treating or preventing diseases which are mediated by IGFR1 (e.g., malignancy).

The present invention provides a binding composition (e.g., an antibody or antigen-binding fragment thereof) comprising a light chain, wherein the chain comprises the amino acid sequence of the light chain CDR-L1 defined by SEQ ID NO: 8 or 31, the amino acid sequence of the light chain CDR-L2 defined by SEQ ID NO: 9 or 32 and the amino acid sequence of the light chain CDR-L3 defined by SEQ ID NO: 10 or 33. Also provided is a binding composition (e.g., an antibody or antigen-binding fragment thereof) including a heavy chain, wherein the chain includes the amino acid sequence of the heavy chain CDR-H1 defined by SEQ ID NO: 14 or 37, the amino acid sequence of the heavy chain CDR-H2 defined by SEQ ID NO: 15 or 38 and the amino acid sequence of the heavy chain CDR-H3 defined by SEQ ID NO: 16 or 39.

Preferably, the binding composition (e.g., an antibody or antigen-binding fragment thereof) of the invention comprises a light chain variable region, preferably a mature light chain variable region, which includes amino acids 20-128 of SEQ ID NO: 2, amino acids 21-130 of SEQ ID NO: 25, amino acids 20-128 of SEQ ID NO: 41 or 43 or amino acids 20-128 of SEQ ID NO: 41, 43, 72, 74, 76 or 78 and/or a heavy chain variable region, preferably a mature heavy chain variable region, which includes amino acids 20-137 of SEQ ID NO: 4, amino acids 20-140 of SEQ ID NO: 27, amino acids 20-137 of SEQ ID NO: 45 or amino acids 20-137 of SEQ ID NO: 112.

Pharmaceutical compositions comprising a binding composition of the present invention and a pharmaceutically acceptable carrier are also provided by the present invention. The binding composition of the invention may also be conjugated to a substance such as polyethylene glycol.

The present invention also includes a binding composition (e.g., a human antibody or antigen binding fragment thereof) which specifically binds to human IGFR1 comprising a property selected from the group consisting of:
(a) binds to IGFR1 (e.g., human IGFR1) with a $K_d$ of about $86 \times 10^{-11}$ or less;
(b) Has an off rate ($K_{off}$) for IGFR1 (e.g., human IGFR1) of about $6.50 \times 10^{-5}$ or smaller;
(c) Has an on rate ($K_{on}$) for IGFR1 (e.g., human IGFR1) of about $0.7 \times 10^5$ or greater;
(d) Competes with IGF1 for binding to IGFR1 (e.g., human IGFR1);
(e) Inhibits autophosphorylation (e.g., with an $IC_{50}$ of 0.10 nM) of IGFR1 (e.g., human IGFR1); and
(f) Inhibits anchorage-independent growth of a cell expressing IGFR1 (e.g., human IGFR1).

Preferably, the binding composition comprises all of said properties (a-f). More preferably, the binding composition (e.g., a human antibody or antigen binding fragment thereof) comprises a member selected from:
(a) a light chain amino acid sequence which comprises CDR-L1 defined by SEQ ID NO: 8, CDR-L2 defined by SEQ ID NO: 9 and CDR-L3 defined by SEQ ID NO: 10;
(b) a light chain amino acid sequence which comprises CDR-L1 defined by SEQ ID NO: 31, CDR-L2 defined by SEQ ID NO: 32 and CDR-L3 defined by SEQ ID NO: 33;
(c) a heavy chain amino acid sequence which comprises CDR-H1 defined by SEQ ID NO: 14 or SEQ ID NO: 17, CDR-H2 defined by SEQ ID NO: 15 and CDR-H3 defined by SEQ ID NO: 16; and
(d) a heavy chain amino acid sequence which comprises CDR-H1 defined by SEQ ID NO: 37 or SEQ ID NO: 70, CDR-H2 defined by SEQ ID NO: 38 and CDR-H3 defined by SEQ ID NO: 39.

The present invention also includes an isolated nucleic acid encoding a peptide selected from:
(a) amino acids 20-128 of SEQ ID NO: 2;
(b) amino acids 21-130 of SEQ ID NO: 25;
(c) amino acids 20-128 of SEQ ID NO: 72;
(d) amino acids 20-128 of SEQ ID NO: 74;
(a) amino acids 20-137 of SEQ ID NO: 4;
(b) amino acids 20-140 of SEQ ID NO: 27;
(c) amino acids 20-137 of SEQ ID NO: 45;
(d) amino acids 20-137 of SEQ ID NO: 112;
(e) amino acids 20-128 of SEQ ID NO: 76; and
(f) amino acids 20-128 of SEQ ID NO: 78.

Preferably, the nucleic acid is selected from:
(a) nucleotides 58-384 of SEQ ID NO: 1;
(b) nucleotides 61-390 of SEQ ID NO: 24;
(c) nucleotides 58-384 of SEQ ID NO: 71;
(d) nucleotides 58-384 of SEQ ID NO: 73.
(e) nucleotides 58-411 of SEQ ID NO: 3;
(f) nucleotides 58-420 of SEQ ID NO: 26;
(g) nucleotides 58-411 of SEQ ID NO: 44;
(h) nucleotides 58-411 of SEQ ID NO: 111;
(i) nucleotides 58-384 of SEQ ID NO: 75; and
(j) nucleotides 58-384 of SEQ ID NO: 77.

The present invention also provides a recombinant vector comprising any of the foregoing polynucleotides along with a host cell comprising the vector.

The present invention also comprises a polypeptide selected from:
(a) amino acids 20-128 of SEQ ID NO: 2;
(b) amino acids 21-130 of SEQ ID NO: 25;
(c) amino acids 20-128 of SEQ ID NO: 72;
(d) amino acids 20-128 of SEQ ID NO: 74;
(e) amino acids 20-137 of SEQ ID NO: 4;
(f) amino acids 20-140 of SEQ ID NO: 27;
(g) amino acids 20-137 of SEQ ID NO: 45;
(h) amino acids 20-137 of SEQ ID NO: 112;
(i) amino acids 20-128 of SEQ ID NO: 76; and
(j) amino acids 20-128 of SEQ ID NO: 78.

Preferably, the binding composition of the present invention is a human antibody comprising at least one (e.g., 1 or 2) light chain/heavy chain combination selected from:
a) a light chain variable region comprising amino acids 20-128 of SEQ ID NO: 2 and a heavy chain variable region comprising amino acids 20-137 of SEQ ID NO: 4; [15H12/19D12 mature LC-15H12/19D12 mature HC]
b) a light chain variable region comprising amino acids 21-130 of SEQ ID NO: 25 and a heavy chain variable region comprising amino acids 20-140 of SEQ ID NO: 27; [1H3 mature LC-1H3 mature HC]
c) a light variable region comprising amino acids 20-128 of SEQ ID NO: 72 and a heavy chain variable region comprising amino acids 20-137 of SEQ ID NO: 45; [mature LCC-mature HCA]
d) a light variable region comprising amino acids 20-128 of SEQ ID NO: 74 and a heavy chain variable region comprising amino acids 20-137 of SEQ ID NO: 45; [mature LCD-mature HCA]
e) a light variable region comprising amino acids 20-128 of SEQ ID NO: 76 and a heavy chain variable region comprising amino acids 20-137 of SEQ ID NO: 45; [mature LCE-mature HCA]
f) a light variable region comprising amino acids 20-128 of SEQ ID NO: 78 and a heavy chain variable region comprising amino acids 20-137 of SEQ ID NO: 45; [mature LCF-mature HCA]
g) a light variable region comprising amino acids 20-128 of SEQ ID NO: 72 and a heavy chain variable region comprising amino acids 20-137 of SEQ ID NO: 112; [mature LCC-mature HCB]
h) a light variable region comprising amino acids 20-128 of SEQ ID NO: 74 and a heavy chain variable region comprising amino acids 20-137 of SEQ ID NO: 112; [mature LCD-mature HCB]
i) a light variable region comprising amino acids 20-128 of SEQ ID NO: 76 and a heavy chain variable region comprising amino acids 20-137 of SEQ ID NO: 112; [mature LCE-mature HCB] and
j) a light variable region comprising amino acids 20-128 of SEQ ID NO: 78 and a heavy chain variable region comprising amino acids 20-137 of SEQ ID NO: 112. [mature LCF-mature HCB].

More preferably, the human antibody is a tetramer comprising two of the foregoing light/heavy chain pairs. Preferably, the human antibody includes mature LCF paired with mature HCA or mature HCB.

Also provided is a method for making a polypeptide comprising amino acids 20-128 of SEQ ID NO: 2, amino acids 20-137 of SEQ ID NO: 4, amino acids 21-130 of SEQ ID NO: 25, amino acids 20-140 of SEQ ID NO: 27, amino acids 20-128 of SEQ ID NO: 41, 43, 72, 74, 76 or 78, amino acids 20-137 of SEQ ID NO: 45 or amino acids 20-137 of SEQ ID NO: 112 comprising culturing the host cell under conditions in which the polypeptide is produced. Preferably, the polypeptide is also isolated from the host cell.

The invention also provides a method for treating or preventing a medical condition in a subject which is mediated by elevated expression or activity of Insulin-like Growth Factor Receptor-I or by elevated expression of one or more of its ligands (e.g., IGF-I or IGF-II) comprising administering a binding composition of the invention (e.g., antibody or antigen-binding fragment of the invention) to the subject. Preferably, the binding composition comprises a member selected from:
(a) a light chain amino acid sequence which comprises CDR-L1 defined by SEQ ID NO: 8, CDR-L2 defined by SEQ ID NO: 9 and CDR-L3 defined by SEQ ID NO: 10;
(b) a light chain amino acid sequence which comprises CDR-L1 defined by SEQ ID NO: 31, CDR-L2 defined by SEQ ID NO: 32 and CDR-L3 defined by SEQ ID NO: 33;
(c) a heavy chain amino acid sequence which comprises CDR-H1 defined by SEQ ID NO: 14 or SEQ ID NO: 17, CDR-H2 defined by SEQ ID NO: 15 and CDR-H3 defined by SEQ ID NO: 16; and
(d) a heavy chain amino acid sequence which comprises CDR-H1 defined by SEQ ID NO: 37 or SEQ ID NO: 70, CDR-H2 defined by SEQ ID NO: 38 and CDR-H3 defined by SEQ ID NO: 39.

The present invention includes any plasmid selected from the group consisting of:
(i) CMV promoter-15H12/19D12 HCA (γ4)—
    Deposit name: "15H12/19D12 HCA (γ4)";
    ATCC accession No.: PTA-5214;
(ii) CMV promoter-15H12/19D12 HCB (γ4)—
    Deposit name: "15H12/19D12 HCB (γ4)";
    ATCC accession No.: PTA-5215;
(iii) CMV promoter-15H12/19D12 HCA (γ1)—
    Deposit name: "15H12/19D12 HCA (γ1)";
    ATCC accession No.: PTA-5216;
(iv) CMV promoter-15H12/19D12 LCC (κ)—
    Deposit name: "15H12/19D12 LCC (κ)";
    ATCC accession No.: PTA-5217;
(v) CMV promoter-15H12/19D12 LCD (κ)—
    Deposit name: "15H12/19D12 LCD (κ)";
    ATCC accession No.: PTA-5218;
(vi) CMV promoter-15H12/19D12 LCE (κ)—
    Deposit name: "15H12/19D12 LCE (κ)";
    ATCC accession No.: PTA-5219; and
(vii) CMV promoter-15H12/19D12 LCF (κ)—
    Deposit name: "15H12/19D12 LCF (κ)";
    ATCC accession No.: PTA-5220;

as well as the nucleic acid inserts of any of the foregoing plasmids. Also included are the nucleic acid portions of the inserts encoding the immunoglobulin variable regions included in the plasmid inserts optionally including the immunoglobulin constant region (i.e., excluding the signal sequence). Also included are any polypeptides encoded by the nucleic acids of any of the foregoing plasmid inserts as well as polypeptides encoding the immunoglobulin variable regions included in any insert optionally including the immunoglobulin constant region (i.e., excluding the signal sequence).

The above-identified plasmids were deposited, under the Budapest Treaty, on May 21, 1003 with the American Type Culture Collection (ATCC); 10801 University Boulevard; Manassas, Va. 20110-2209. All restrictions on access to the plasmids deposited at the ATCC have been irrevocably removed.

Preferably, the binding composition is combined with a pharmaceutically acceptable carrier in a pharmaceutical composition. Such medical conditions, as contemplated by the present invention, include acromegaly, ovarian cancer, pancreatic cancer, benign prostatic hyperplasia, breast cancer, prostate cancer, bone cancer, lung cancer, colorectal cancer, cervical cancer, synovial sarcoma, diarrhea associated with metastatic carcinoid, vasoactive intestinal peptide secreting tumors, gigantism, psoriasis, atherosclerosis, smooth muscle restenosis of blood vessels and inappropriate microvascular proliferation.

The binding compositions may be administered to a subject, for example, by a parenteral route. Combination therapies comprising administration of a binding composition of the present invention in association with an anti-cancer therapy agent or in association with an anti-cancer therapeutic procedure are also provided.

A method for producing a fully-human anti-IGFR1 antibody which comprises the steps of immunizing a transgenic non-human animal having a genome comprising a human heavy chain transgene and a human light chain transgene with IGFR1 antigenic polypeptide, preferably amino acids 30-902 of SEQ ID NO: 19 and/or a cell (e.g., HEK293) which expresses IGFR1 on its surface, such that antibodies are produced by B cells of the animal; isolating B cells of the animal; fusing the B cells with myeloma cells to form immortal, hybridoma cells that secrete human monoclonal antibodies specific for IGFR1; and isolating the human monoclonal antibodies specific for IGFR1 is also provided.

DETAILED DESCRIPTION

Preferred embodiments of the present invention include a fully human, monoclonal antibody or antigen-binding fragment thereof which specifically recognizes and binds to Insulin-like Growth Factor Receptor-I, preferably amino acids 30-902 of SEQ ID NO: 19. Preferably, the antibody or antigen-binding fragment thereof is 1H3, 15H12, 19D12, 15H12/19D12 LCA, 15H12/19D12 LCB, 15H12/19D12 LCC, 15H12/19D12 LCD, 15H12/19D12 LCE, 15H12/19D12 LCF, 15H12/19D12 HCA or 15H12/19D12 HCB.

A binding composition or agent refers to a molecule that binds with specificity to IGFR1, e.g., in a ligand-receptor type fashion or an antibody-antigen interaction, e.g., proteins which specifically associate with IGFR1, e.g., in a natural physiologically relevant protein-protein interaction, either covalent or non-covalent. The term "binding composition" is preferably a polypeptide, such as a full antibody or antigen-binding fragment thereof of the present invention (e.g., 15H12/19D12 LCA, 15H12/19D12 LCB, 15H12/19D12 LCC, 15H12/19D12 LCD, 15H12/19D12 LCE, 15H12/19D12 LCF, 15H12/19D12 HCA OR 15H12/19D12 HCB or any peptide set forth, below, in Table 1).

The antibodies and antigen-binding fragments of the invention may be used to inhibit growth of cells, preferably malignant cells, both in vitro and in vivo. Without being bound by a single theory, the antibodies and antigen-binding fragments of the invention may inhibit cellular growth by inhibiting the interaction between IGFR1 and a ligand for the receptor, such as Insulin-like Growth Factor-I (IGF-I) or Insulin-like Growth Factor-II (IGF-II). The antibodies and antigen-binding fragments may also inhibit IGFR1 autophosphorylation, inhibit anchorage-independent growth of cells (e.g., cancer cells) expressing IGFR1 and inhibit activation of AKT kinase by inducing degradation of IGFR1. Preferably, the antibodies and antigen-binding fragments neutralize the activity of IGFR1 and/or down-regulate IGFR1. The antibodies and antigen-binding fragments may be used to treat or prevent diseases which are mediated by IGFR1. The present invention also provides methods for making the antibodies and antigen-binding fragments of the invention.

The term "antibody molecule" refers to whole antibodies (e.g., IgG, preferably, IgG1 or IgG4) and fragments, preferably antigen-binding fragments, thereof. Antibody fragments include Fab antibody fragments, F(ab)$_2$ antibody fragments, Fv antibody fragments, single chain Fv antibody fragments and dsFv antibody fragments.

The terms "IGFR1" "Insulin-like Growth Factor Receptor-I" and "Insulin-like Growth Factor Receptor, type I" are well known in the art. Although IGFR1 may be from any organism, it is preferably from an animal, more preferably from a mammal (e.g., mouse, rat, rabbit, sheep or dog) and most preferably from a human. The nucleotide and amino acid sequence of a typical human IGFR1 precursor has the Genbank Accession No. X04434 or NM_000875 (SEQ ID NO: 19). Cleavage of the precursor (e.g., between amino acids 710 and 711) produces an α-subunit and a β-subunit which associate to form a mature receptor. In preferred embodiments of the invention, amino acids 30-902, from the full length IGFR1 polypeptide are used as an antigen for generation of anti-IGFR1 antibodies.

The terms "IGF-I" "Insulin-like Growth Factor-I" and "Insulin-like Growth Factor, type I" are also well known in the art. The terms "IGF-II" "Insulin-like Growth Factor-II" and "Insulin-like Growth Factor, type II" are also well known in the art. Although IGF-I or IGF-II may be from any organism, they are preferably from an animal, more preferably from a mammal (e.g., mouse, rat, rabbit, sheep or dog) and most preferably from a human. The nucleic acid and amino acid sequence of typical, human IGF-I and IGF-II have the Genbank Accession No. XM_052648 (SEQ ID NO: 20) and NM_000612 (SEQ ID NO: 21), respectively. The term "sIGFR1" or "soluble IGFR1" includes any soluble fragment of IGFR1 (e.g., human IGFR1), preferably a fragment from which the receptor trans-membrane region has been deleted, more preferably amino acids 30-902 of SEQ ID NO: 19.

The amino acid sequence of the variable region of preferred, fully human, monoclonal anti-IGFR1 antibody molecules of the invention (e.g., 1H3, 15H12 and 19D12) along with the nucleotide sequences of nucleic acids which encode the regions are summarized in Table 1. The present invention includes any nucleic acid or polypeptide (e.g., antibody) which comprises one or more (e.g., 1, 2, 3, 4, 5, 6, 7 or 8) of any of the nucleic acids or polypeptides (including mature fragments thereof) set forth, below, in Table 1. Table 1 also includes a summary of the amino acid and nucleotide sequences which correspond to the CDR regions of the antibodies. The amino acid and nucleotide sequences corresponding to the variable region of 15H12 and 19D12 are identical; for this reason, only a single sequence for each variable region or CDR is shown.

TABLE 1

| Summary of amino acid and nucleotide sequences of the invention. | |
|---|---|
| SEQUENCE | SEQUENCE IDENTIFIER |
| Nucleotide sequence encoding the 15H12 and 19D12 light chain variable region-including signal peptide (15H12/19D12 LC) | SEQ ID NO: 1 |

TABLE 1-continued

| Summary of amino acid and nucleotide sequences of the invention. | |
|---|---|
| SEQUENCE | SEQUENCE IDENTIFIER |
| Amino acid sequence of the 15H12 and 19D12 light chain variable region-including signal peptide | SEQ ID NO: 2 |
| Nucleotide sequence encoding the 15H12 and 19D12 heavy chain variable region including signal peptide (15H12/19D12 HC) | SEQ ID NO: 3 |
| Amino acid sequence of the 15H12 and 19D12 heavy chain variable region including signal peptide | SEQ ID NO: 4 |
| Nucleotide sequence encoding the 15H12 and 19D12 CDR-L1 | SEQ ID NO: 5 |
| Nucleotide sequence encoding the 15H12 and 19D12 CDR-L2 | SEQ ID NO: 6 |
| Nucleotide sequence encoding the 15H12 and 19D12 CDR-L3 | SEQ ID NO: 7 |
| Amino acid sequence of the 15H12 and 19D12 CDR-L1 | SEQ ID NO: 8 |
| Amino acid sequence of the 15H12 and 19D12 CDR-L2 | SEQ ID NO: 9 |
| Amino acid sequence of the 15H12 and 19D12 CDR-L3 | SEQ ID NO: 10 |
| Nucleotide sequence encoding the 15H12 and 19D12 CDR-H1 | SEQ ID NO: 11 |
| Nucleotide sequence encoding the 15H12 and 19D12 CDR-H2 | SEQ ID NO: 12 |
| Nucleotide sequence encoding the 15H12 and 19D12 CDR-H3 | SEQ ID NO: 13 |
| Amino acid sequence of the 15H12 and 19D12 CDR-H1 | SEQ ID NO: 14 |
| Amino acid sequence of the 15H12 and 19D12 CDR-H2 | SEQ ID NO: 15 |
| Amino acid sequence of the 15H12 and 19D12 CDR-H3 | SEQ ID NO: 16 |
| Amino acid sequence of an alternative 15H12 and 19D12 CDR-H1 | SEQ ID NO: 17 |
| Nucleotide sequence encoding an alternative 15H12 and 19D12 CDR-H1 | SEQ ID NO: 18 |
| Amino acid sequence of Insulin-like Growth Factor Receptor-I (IGFR1) | SEQ ID NO: 19 |
| Amino acid sequence of Insulin-like Growth Factor-I (IGF1) | SEQ ID NO: 20 |
| Amino acid sequence of Insulin-like Growth Factor-II (IGF2) | SEQ ID NO: 21 |
| Nucleotide sequence of PCR primer | SEQ ID NO: 22 |
| Nucleotide sequence of PCR primer | SEQ ID NO: 23 |
| Nucleotide sequence encoding the 1H3 light chain variable region-including signal peptide (1H3 LC) | SEQ ID NO: 24 |
| Amino acid sequence of the 1H3 light chain variable region-including signal peptide | SEQ ID NO: 25 |
| Nucleotide sequence encoding the 1H3 heavy chain variable region including signal peptide (1H3 HC) | SEQ ID NO: 26 |
| Amino acid sequence of the 1H3 heavy chain variable region including signal peptide | SEQ ID NO: 27 |
| Nucleotide sequence encoding the 1H3 CDR-L1 | SEQ ID NO: 28 |
| Nucleotide sequence encoding the 1H3 CDR-L2 | SEQ ID NO: 29 |
| Nucleotide sequence encoding the 1H3 CDR-L3 | SEQ ID NO: 30 |

TABLE 1-continued

Summary of amino acid and nucleotide sequences of the invention.

| SEQUENCE | SEQUENCE IDENTIFIER |
|---|---|
| Amino acid sequence of the 1H3 CDR-L1 | SEQ ID NO: 31 |
| Amino acid sequence of the 1H3 CDR-L2 | SEQ ID NO: 32 |
| Amino acid sequence of the 1H3 CDR-L3 | SEQ ID NO: 33 |
| Nucleotide sequence encoding the 1H3 CDR-H1 | SEQ ID NO: 34 |
| Nucleotide sequence encoding the 1H3 CDR-H2 | SEQ ID NO: 35 |
| Nucleotide sequence encoding the 1H3 CDR-H3 | SEQ ID NO: 36 |
| Amino acid sequence of the 1H3 CDR-H1 | SEQ ID NO: 37 |
| Amino acid sequence of the 1H3 CDR-H2 | SEQ ID NO: 38 |
| Amino acid sequence of the 1H3 CDR-H3 | SEQ ID NO: 39 |
| Nucleotide sequence encoding the 15H12/19D12 light chain A (LCA) | SEQ ID NO: 40 |
| Amino acid sequence of the 15H12/19D12 light chain A | SEQ ID NO: 41 |
| Nucleotide sequence encoding the 15H12/19D12 light chain B (LCB) | SEQ ID NO: 42 |
| Amino acid sequence of the 15H12/19D12 light chain B | SEQ ID NO: 43 |
| Nucleotide sequence encoding the 15H12/19D12 heavy chain A (HCA) | SEQ ID NO: 44 |
| Amino acid sequence of the 15H12/19D12 heavy chain A | SEQ ID NO: 45 |
| Nucleotide sequence encoding the 15H12/19D12 light chain A framework region 1 | SEQ ID NO: 46 |
| Amino acid sequence of the 15H12/19D12 light chain A framework region 1 | SEQ ID NO: 47 |
| Nucleotide sequence encoding the 15H12/19D12 light chain A framework region 2 | SEQ ID NO: 48 |
| Amino acid sequence of the 15H12/19D12 light chain A framework region 2 | SEQ ID NO: 49 |
| Nucleotide sequence encoding the 15H12/19D12 light chain A framework region 3 | SEQ ID NO: 50 |
| Amino acid sequence of the 15H12/19D12 light chain A framework region 3 | SEQ ID NO: 51 |
| Nucleotide sequence encoding the 15H12/19D12 light chain A framework region 4 | SEQ ID NO: 52 |
| Amino acid sequence of the 15H12/19D12 light chain A framework region 4 | SEQ ID NO: 53 |
| Nucleotide sequence encoding the 15H12/19D12 light chain B framework region 1 | SEQ ID NO: 54 |
| Amino acid sequence of the 15H12/19D12 light chain B framework region 1 | SEQ ID NO: 55 |
| Nucleotide sequence encoding the 15H12/19D12 light chain B framework region 2 | SEQ ID NO: 56 |
| Amino acid sequence of the 15H12/19D12 light chain B framework region 2 | SEQ ID NO: 57 |
| Nucleotide sequence encoding the 15H12/19D12 light chain B framework region 3 | SEQ ID NO: 58 |
| Amino acid sequence of the 15H12/19D12 light chain B framework region 3 | SEQ ID NO: 59 |
| Nucleotide sequence encoding the 15H12/19D12 light chain B framework region 4 | SEQ ID NO: 60 |
| Amino acid sequence of the 15H12/19D12 light chain B framework region 4 | SEQ ID NO: 61 |
| Nucleotide sequence encoding the 15H12/19D12 heavy chain A framework region 1 | SEQ ID NO: 62 |
| Amino acid sequence of the 15H12/19D12 heavy chain A framework region 1 | SEQ ID NO: 63 |
| Nucleotide sequence encoding the 15H12/19D12 heavy chain A framework region 2 | SEQ ID NO: 64 |
| Amino acid sequence of the 15H12/19D12 heavy chain A framework region 2 | SEQ ID NO: 65 |
| Nucleotide sequence encoding the 15H12/19D12 heavy chain A framework region 3 | SEQ ID NO: 66 |
| Amino acid sequence of the 15H12/19D12 heavy chain A framework region 3 | SEQ ID NO: 67 |
| Nucleotide sequence encoding the 15H12/19D12 heavy chain A framework region 4 | SEQ ID NO: 68 |
| Amino acid sequence of the 15H12/19D12 heavy chain A framework region 4 | SEQ ID NO: 69 |
| Amino acid sequence of the alternative 1H3 CDR-H1 | SEQ ID NO: 70 |
| Nucleotide sequence encoding the 15H12/19D12 light chain C (LCC) | SEQ ID NO: 71 |
| Amino acid sequence of the 15H12/19D12 light chain C | SEQ ID NO: 72 |
| Nucleotide sequence encoding the 15H12/19D12 light chain D (LCD) | SEQ ID NO: 73 |
| Amino acid sequence of the 15H12/19D12 light chain D | SEQ ID NO: 74 |
| Nucleotide sequence encoding the 15H12/19D12 light chain E (LCE) | SEQ ID NO: 75 |
| Amino acid sequence of the 15H12/19D12 light chain E | SEQ ID NO: 76 |
| Nucleotide sequence encoding the 15H12/19D12 light chain F (LCF) | SEQ ID NO: 77 |
| Amino acid sequence of the 15H12/19D12 light chain F | SEQ ID NO: 78 |
| Nucleotide sequence encoding the 15H12/19D12 light chain C framework region 1 | SEQ ID NO: 79 |
| Amino acid sequence of the 15H12/19D12 light chain C framework region 1 | SEQ ID NO: 80 |
| Nucleotide sequence encoding the 15H12/19D12 light chain C framework region 2 | SEQ ID NO: 81 |
| Amino acid sequence of the 15H12/19D12 light chain C framework region 2 | SEQ ID NO: 82 |
| Nucleotide sequence encoding the 15H12/19D12 light chain C framework region 3 | SEQ ID NO: 83 |
| Amino acid sequence of the 15H12/19D12 light chain C framework region 3 | SEQ ID NO: 84 |
| Nucleotide sequence encoding the 15H12/19D12 light chain C framework region 4 | SEQ ID NO: 85 |

TABLE 1-continued

Summary of amino acid and nucleotide sequences of the invention.

| SEQUENCE | SEQUENCE IDENTIFIER |
|---|---|
| Amino acid sequence of the 15H12/19D12 light chain C framework region 4 | SEQ ID NO: 86 |
| Nucleotide sequence encoding the 15H12/19D12 light chain D framework region 1 | SEQ ID NO: 87 |
| Amino acid sequence of the 15H12/19D12 light chain D framework region 1 | SEQ ID NO: 88 |
| Nucleotide sequence encoding the 15H12/19D12 light chain D framework region 2 | SEQ ID NO: 89 |
| Amino acid sequence of the 15H12/19D12 light chain D framework region 2 | SEQ ID NO: 90 |
| Nucleotide sequence encoding the 15H12/19D12 light chain D framework region 3 | SEQ ID NO: 91 |
| Amino acid sequence of the 15H12/19D12 light chain D framework region 3 | SEQ ID NO: 92 |
| Nucleotide sequence encoding the 15H12/19D12 light chain D framework region 4 | SEQ ID NO: 93 |
| Amino acid sequence of the 15H12/19D12 light chain D framework region 4 | SEQ ID NO: 94 |
| Nucleotide sequence encoding the 15H12/19D12 light chain E framework region 1 | SEQ ID NO: 95 |
| Amino acid sequence of the 15H12/19D12 light chain E framework region 1 | SEQ ID NO: 96 |
| Nucleotide sequence encoding the 15H12/19D12 light chain E framework region 2 | SEQ ID NO: 97 |
| Amino acid sequence of the 15H12/19D12 light chain E framework region 2 | SEQ ID NO: 98 |
| Nucleotide sequence encoding the 15H12/19D12 light chain E framework region 3 | SEQ ID NO: 99 |
| Amino acid sequence of the 15H12/19D12 light chain E framework region 3 | SEQ ID NO: 100 |
| Nucleotide sequence encoding the 15H12/19D12 light chain E framework region 4 | SEQ ID NO: 101 |
| Amino acid sequence of the 15H12/19D12 light chain E framework region 4 | SEQ ID NO: 102 |
| Nucleotide sequence encoding the 15H12/19D12 light chain F framework region 1 | SEQ ID NO: 103 |
| Amino acid sequence of the 15H12/19D12 light chain F framework region 1 | SEQ ID NO: 104 |
| Nucleotide sequence encoding the 15H12/19D12 light chain F framework region 2 | SEQ ID NO: 105 |
| Amino acid sequence of the 15H12/19D12 light chain F framework region 2 | SEQ ID NO: 106 |
| Nucleotide sequence encoding the 15H12/19D12 light chain F framework region 3 | SEQ ID NO: 107 |
| Amino acid sequence of the 15H12/19D12 light chain F framework region 3 | SEQ ID NO: 108 |
| Nucleotide sequence encoding the 15H12/19D12 light chain F framework region 4 | SEQ ID NO: 109 |
| Amino acid sequence of the 15H12/19D12 light chain F framework region 4 | SEQ ID NO: 110 |
| Nucleotide sequence encoding the 15H12/19D12 heavy chain B (HCB) | SEQ ID NO: 111 |
| Amino acid sequence of the 15H12/19D12 heavy chain B | SEQ ID NO: 112 |
| Nucleotide sequence encoding the 15H12/19D12 heavy chain B framework region 1 | SEQ ID NO: 113 |
| Amino acid sequence of the 15H12/19D12 heavy chain B framework region 1 | SEQ ID NO: 114 |
| Nucleotide sequence encoding the 15H12/19D12 heavy chain B F framework region 2 | SEQ ID NO: 115 |
| Amino acid sequence of the 15H12/19D12 heavy chain B framework region 2 | SEQ ID NO: 116 |
| Nucleotide sequence encoding the 15H12/19D12 heavy chain B framework region 3 | SEQ ID NO: 117 |
| Amino acid sequence of the 15H12/19D12 heavy chain B framework region 3 | SEQ ID NO: 118 |
| Nucleotide sequence encoding the 15H12/19D12 heavy chain B framework region 4 | SEQ ID NO: 119 |
| Amino acid sequence of the 15H12/19D12 heavy chain B framework region 4 | SEQ ID NO: 120 |

CDR-L1 is the first complementarity determining region (CDR) which occurs in the light chain, CDR-L2 is the second CDR which occurs on the light chain and CDR-L3 is the third CDR which occurs on the light chain.

Similarly, CDR-H1 is the first CDR which occurs on the heavy chain, CDR-H2 is the second CDR which occurs on the heavy chain and CDR-H3 is the third CDR which occurs on the heavy chain.

FR-L1 is the first framework region of the light chain, FR-L2 is the second framework region of the light chain, FR-L3 is the third framework region of the light chain, FR-L4 is the fourth framework region on the light chain, FR-H1 is the first framework region of the heavy chain, FR-H2 is the second framework region of the heavy chain, FR-H3 is the third framework region of the heavy chain and FR-H4 is the fourth framework region of the heavy chain. These terms and the arrangement of CDRs and FRs on an immunoglobulin chain are well known in the art.

A mature light chain variable region of the invention, which lacks the signal peptide (i.e., first 19 or 20 residues), is amino acids 20-128 of SEQ ID NO: 2, 41, 43, 72, 74, 76 or 78 which is encoded by nucleotides 58-384 of SEQ ID NO: 1, 40, 42, 71, 73, 75, or 77 or amino acids 21-130 of SEQ ID NO: 25 which is encoded by nucleotides 61-390 of SEQ ID NO: 24.

A mature heavy chain variable region, which lacks the signal peptide (i.e., first 19 residues), is amino acids 20-137 of SEQ ID NO: 4, 45 or 112 which is encoded by nucleotides 58-411 of SEQ ID NO: 3, 44 or 111 or amino acids 20-140 of SEQ ID NO: 27 which is encoded by nucleotides 58420 of SEQ ID NO: 26.

In some embodiments the 15H12 and 19D12 CDR-H1 is GFTFSSFAMH (SEQ ID NO: 17) which is encoded by the nucleotide sequence of SEQ ID NO: 18. In some embodiments the 1H3 CDR-H1 is NYAMH (SEQ ID NO: 70).

The present invention also includes antibodies and antigen-binding fragments which include the framework regions of the antibodies and antigen-binding fragments of the invention. Preferably, FR-L1 is amino acids 20-42 of SEQ ID NO: 2 or amino acids 21-43 of SEQ ID NO: 25; FR-L2 is amino acids 54-68 of SEQ ID NO: 2 or amino acids 55-69 of SEQ ID NO: 25; FR-L3 is amino acids 76-107 of SEQ ID NO: 2 or amino acids 77-108 of SEQ ID NO: 25; FR-L4 is amino acids 117-128 of SEQ ID NO: 2 or amino acids 128-130 of SEQ ID NO: 25; FR-H1 is amino acids 20-44 or 20-49 of SEQ ID NO: 4 or amino acids 2044 or 20-49 of SEQ ID NO: 27; FR-H2 is amino acids 55-68 of SEQ ID NO: 4 or amino acids 55-68 of SEQ ID NO: 27; FR-H3 is amino acids 85-116 of SEQ ID NO: 4 or amino acids 85-116 of SEQ ID NO: 27 and FR-H4 is amino acids 127-137 of SEQ ID NO: 4 or amino acids 130-140 of SEQ ID NO: 27.

In preferred embodiments, the antibody molecules of the present invention include FR-L1 defined by amino acids 20-42 of SEQ ID NO: 41 or 43; FR-L2 defined by amino acids 54-68 of SEQ ID NO: 41 or 43; FR-L3 defined by amino acids 76-107 of SEQ ID NO: 41 or 43; and FR-L4 defined by amino acids 117-128 of SEQ ID NO: 41 or 43. Furthermore, preferred embodiments include antibody molecules including FR-H1 defined by amino acids 20-44 of SEQ ID NO: 45; FR-H2 defined by amino acids 55-68 of SEQ ID NO: 45; FR-H3 defined by amino acids 85-116 of SEQ ID NO: 45; and FR-H4 defined by amino acids 127-137 of SEQ ID NO: 45.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

A "polynucleotide", "nucleic acid" or "nucleic acid molecule" may refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in single stranded form, double-stranded form or otherwise.

A "polynucleotide sequence", "nucleic acid sequence" or "nucleotide sequence" is a series of nucleotide bases (also called "nucleotides") in a nucleic acid, such as DNA or RNA, and means any chain of two or more nucleotides.

A "coding sequence" or a sequence "encoding" an expression product, such as a RNA, polypeptide, protein, or enzyme, is a nucleotide sequence that, when expressed, results in production of the product.

The term "gene" means a DNA sequence that codes for or corresponds to a particular sequence of ribonucleotides or amino acids which comprise all or part of one or more RNA molecules, proteins or enzymes, and may or may not include regulatory DNA sequences, such as promoter sequences, which determine, for example, the conditions under which the gene is expressed. Genes may be transcribed from DNA to RNA which may or may not be translated into an amino acid sequence.

"Amplification" of DNA as used herein may denote the use of polymerase chain reaction (PCR) to increase the concentration of a particular DNA sequence within a mixture of DNA sequences. For a description of PCR see Saiki, et al., Science (1988) 239: 487. In a specific embodiment, the present invention includes a nucleic acid, which encodes an anti-IGFR1 antibody, an anti-IGFR1 antibody heavy or light chain, an anti-IGFR1 antibody heavy or light chain variable region, an anti-IGFR1 antibody heavy or light chain constant region or anti-IGFR1 antibody CDR (e.g., CDR-L1, CDR-L2, CDR-L3, CDR-H1, CDR-H2 or CDR-H3) which can be amplified by PCR.

As used herein, the term "oligonucleotide" refers to a nucleic acid, generally of at least 10 (e.g., 10, 11, 12, 13 or 14), preferably at least 15 (e.g., 15, 16, 17, 18 or 19), and more preferably at least 20 nucleotides (e.g., 20, 21, 22, 23, 24, 25, 26, 27, 28, 29 or 30), preferably no more than 100 nucleotides (e.g., 40, 50, 60, 70, 80 or 90), that may be hybridizable to a genomic DNA molecule, a cDNA molecule, or an mRNA molecule encoding a gene, mRNA, cDNA, or other nucleic acid of interest. Oligonucleotides can be labeled, e.g., by incorporation of $^{32}$P-nucleotides, $^{3}$H-nucleotides, $^{14}$C-nucleotides, $^{35}$S-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids. Generally, oligonucleotides are prepared synthetically, preferably on a nucleic acid synthesizer.

The sequence of any nucleic acid (e.g., a nucleic acid encoding an IGFR1 gene or a nucleic acid encoding an anti-IGFR1 antibody or a fragment or portion thereof) may be sequenced by any method known in the art (e.g., chemical sequencing or enzymatic sequencing). "Chemical sequencing" of DNA may denote methods such as that of Maxam and Gilbert (1977) (Proc. Natl. Acad. Sci. USA 74:560), in which DNA is randomly cleaved using individual base-specific reactions. "Enzymatic sequencing" of DNA may denote methods such as that of Sanger (Sanger, et al., (1977) Proc. Natl. Acad. Sci. USA 74:5463).

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

A "promoter" or "promoter sequence" is a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a nucleic acid of the invention (e.g., SEQ ID NO: 1, 3, 5-7, 11-13, 18, 22-24, 26, 28-30 or 34-36). Promoters which may be used to control gene expression include, but are not limited to, cytomegalovirus (CMV) promoter (U.S. Pat. Nos. 5,385,839 and 5,168,062), the SV40 early promoter region (Benoist, et al., (1981) Nature 290:304-310), the promoter contained in the 3' long terminal repeat of Rous sarcoma virus (Yamamoto, et al., (1980) Cell 22:787-797), the herpes thymidine kinase promoter (Wagner, et al., (1981) Proc. Natl. Acad. Sci. USA 78:1441-1445), the regulatory sequences of the metallothionein gene (Brinster, et al., (1982) Nature 296:39-42); prokaryotic expression vectors such as the β-lactamase promoter (Villa-Komaroff, et al., (1978) Proc. Natl. Acad. Sci. USA 75:3727-3731), or the tac promoter (DeBoer, et al., (1983) Proc. Natl. Acad. Sci. USA 80:21-25); see also "Useful proteins from recombinant bacteria" in Scientific American (1980) 242:74-94; and promoter elements from yeast or other fungi such as the Gal 4 promoter, the ADC (alcohol dehydrogenase) promoter, PGK (phosphoglycerol kinase) promoter or the alkaline phosphatase promoter.

A coding sequence is "under the control of", "functionally associated with" or "operably associated with" transcriptional and translational control sequences in a cell when the sequences direct RNA polymerase mediated transcription of the coding sequence into RNA, preferably mRNA, which then may be trans-RNA spliced (if it contains introns) and, optionally, translated into a protein encoded by the coding sequence.

The terms "express" and "expression" mean allowing or causing the information in a gene, RNA or DNA sequence to become manifest; for example, producing a protein by activating the cellular functions involved in transcription and translation of a corresponding gene. A DNA sequence is expressed in or by a cell to form an "expression product" such as an RNA (e.g., mRNA) or a protein (e.g., antibody 1H3, 15H12 or 19D12 or a fragment thereof). The expression product itself may also be said to be "expressed" by the cell.

The terms "vector", "cloning vector" and "expression vector" mean the vehicle (e.g., a plasmid) by which a DNA or RNA sequence can be introduced into a host cell, so as to transform the host and, optionally, promote expression and/or replication of the introduced sequence.

The term "transfection" or "transformation" means the introduction of a nucleic acid into a cell. These terms may refer to the introduction of a nucleic acid encoding an anti-IGFR1 antibody or fragment thereof into a cell. The introduced gene or sequence may be called a "clone". A host cell that receives the introduced DNA or RNA has been "transformed" and is a "transformant" or a "clone". The DNA or RNA introduced to a host cell can come from any source, including cells of the same genus or species as the host cell, or cells of a different genus or species.

The term "host cell" means any cell of any organism that is selected, modified, transfected, transformed, grown, or used or manipulated in any way, for the production of a substance by the cell, for example the expression or replication, by the cell, of a gene, a DNA or RNA sequence, a protein or an enzyme.

The term "expression system" means a host cell and compatible vector which, under suitable conditions, can express a protein or nucleic acid which is carried by the vector and introduced to the host cell. Common expression systems include E. coli host cells and plasmid vectors, insect host cells and Baculovirus vectors, and mammalian host cells and vectors. In a specific embodiment, IGFR1 or an antibody and antigen-binding fragment of the invention may be expressed in human embryonic kidney cells (HEK293). Other suitable cells include CHO (chinese hamster ovary) cells, HeLa cells and NIH 3T3 cells and NSO cells (non-Ig-producing murine myeloma cell line). Nucleic acids encoding an antibody or antigen-binding fragment of the invention, sIGFR1 or IGFR1 may be expressed at high levels in an E. coli/T7 expression system as disclosed in U.S. Pat. Nos. 4,952,496, 5,693,489 and 5,869,320 and in Davanloo, P., et al., (1984) Proc. Natl. Acad. Sci. USA 81, 2035-2039; Studier, F. W., et al., (1986) J. Mol. Biol. 189: 113-130; Rosenberg, A. H., et al., (1987) Gene 56: 125-135; and Dunn, J. J., et al., (1988) Gene 68: 259 which are herein incorporated by reference.

The present invention contemplates any superficial or slight modification to the amino acid or nucleotide sequences which correspond to the antibodies or antigen-binding fragments of the invention. In particular, the present invention contemplates sequence conservative variants of the nucleic acids which encode the antibodies or antigen-binding fragments of the invention. "Sequence-conservative variants" of a polynucleotide sequence are those in which a change of one or more nucleotides in a given codon results in no alteration in the amino acid encoded at that position. Function-conservative variants of the antibodies of the invention are also contemplated by the present invention. "Function-conservative variants" are those in which one or more amino acid residues in a protein or enzyme have been changed without altering the overall conformation and function of the polypeptide, including, but, by no means, limited to, replacement of an amino acid with one having similar properties. Amino acids with similar properties are well known in the art. For example, polar/hydrophilic amino acids which may be interchangeable include asparagine, glutamine, serine, cysteine, threonine, lysine, arginine, histidine, aspartic acid and glutamic acid; nonpolar/hydrophobic amino acids which may be interchangeable include glycine, alanine, valine, leucine, isoleucine, proline, tyrosine, phenylalanine, tryptophan and methionine; acidic amino acids which may be interchangeable include aspartic acid and glutamic acid and basic amino acids which may be interchangeable include histidine, lysine and arginine.

The present invention includes anti-IGFR1 antibodies and fragments thereof which are encoded by nucleic acids as described in Table 1 as well as nucleic acids which hybridize thereto. Preferably, the nucleic acids hybridize under low stringency conditions, more preferably under moderate stringency conditions and most preferably under high stringency conditions and, preferably, exhibit IGFR1 binding activity. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook, et al., supra). The conditions of temperature and ionic strength determine the "stringency" of the hybridization. Typical low stringency hybridization conditions may be 55° C., 5×SSC, 0.1% SDS, 0.25% milk, and no formamide; or 30% formamide, 5×SSC, 0.5% SDS. Typical, moderate stringency hybridization conditions are similar to the low stringency conditions except the hybridization is carried out in 40% formamide, with 5× or 6×SSC. High stringency hybridization conditions are similar to low stringency conditions except the hybridization conditions are carried out in 50% formamide, 5× or 6×SSC and, optionally, at a higher temperature (e.g., 57° C., 59° C., 60° C., 62° C., 63° C., 65° C. or 68° C.). In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter nucleic acids, i.e., oligonucleotides, the position of mismatches becomes more important, and the length of the oligonucleotide determines its specificity (see Sambrook, et al., supra, 11.7-11.8).

Also included in the present invention are nucleic acids comprising nucleotide sequences and polypeptides comprising amino acid sequences which are at least about 70% identical, preferably at least about 80% identical, more preferably at least about 90% identical and most preferably at least about 95% identical (e.g., 95%, 96%, 97%, 98%, 99%, 100%) to the reference nucleotide and amino acid sequences of Table 1 when the comparison is performed by a BLAST algorithm wherein the parameters of the algorithm are selected to give the largest match between the respective sequences over the entire length of the respective reference sequences. Polypeptides comprising amino acid sequences which are at least about 70% similar, preferably at least about 80% similar, more preferably at least about 90% similar and most preferably at least about 95% similar (e.g., 95%, 96%, 97%, 98%, 99%, 100%) to the reference amino acid sequences of Table 1 (e.g., SEQ ID NOs. 2 (e.g., amino acids 20-128), 4 (e.g., amino acids 20-137), 8-10, 14-16, 17, 25 (e.g., amino acids 21-130), 27 (e.g., amino acids 20-140), 31-33 or 37-39) when the comparison is performed with a BLAST algorithm wherein the parameters of the algorithm are selected to give the largest match between the respective sequences over the entire length of the respective reference sequences, are also included in the present invention.

Sequence identity refers to exact matches between the nucleotides or amino acids of two sequences which are being compared. Sequence similarity refers to both exact matches between the amino acids of two polypeptides which are being compared in addition to matches between nonidentical, biochemically related amino acids. Biochemically related amino acids which share similar properties and may be interchangeable are discussed above.

The following references regarding the BLAST algorithm are herein incorporated by reference: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in *Atlas of Protein Sequence and Structure*, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in *Atlas of Protein Sequence and Structure*, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in *Theoretical and Computational Methods in Genome Research* (S. Suhai, ed.), (1997) pp. 1-14, Plenum, N.Y.

Antibody Structure

In general, the basic antibody structural unit is known to comprise a tetramer. Each tetramer includes two identical pairs of polypeptide chains, each pair having one "light" (about 25 kDa) and one "heavy" chain (about 50-70 kDa). The amino-terminal portion of each chain may include a variable region of about 100 to 110 or more amino acids primarily responsible for antigen recognition. The carboxy-terminal portion of each chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes).

The variable regions of each light/heavy chain pair may form the antibody binding site. Thus, in general, an intact IgG antibody has two binding sites. Except in bifunctional or bispecific antibodies, the two binding sites are, in general, the same.

Normally, the chains all exhibit the same general structure of relatively conserved framework regions (FR) joined by three hypervariable regions, also called complementarity determining regions or CDRs. The CDRs from the two chains of each pair are usually aligned by the framework regions, enabling binding to a specific epitope. In general, from N-terminal to C-terminal, both light and heavy chains comprise the domains FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat (1978) Adv. Prot. Chem. 32:1-75; Kabat, et al., (1977) J. Biol. Chem. 252:6609-6616; Chothia, et al., (1987) J Mol. Biol. 196:901-917 or Chothia, et al., (1989) Nature 342:878-883. The present invention provides antibodies or antigen-binding fragments of the invention comprising CDRs and FRs from the light and heavy chains of 1H3, 15H12 and 19D12 (e.g., 15H12/19D12 LCA, 15H12/19D12 LCB, 15H12/19D12 HCA, SEQ ID NOs: 2, 4, 25, 27, 41, 43 and 45) as defined by Kabat and Chothia (see above references).

Antibody Molecules

The term "antibody molecule" includes, but is not limited to, antibodies and fragments, preferably antigen-binding fragments, thereof. The term includes monoclonal antibodies, polyclonal antibodies, bispecific antibodies, Fab antibody fragments, F(ab)$_2$ antibody fragments, Fv antibody fragments (e.g., $V_H$ or $V_L$), single chain Fv antibody fragments and dsFv antibody fragments. Furthermore, the antibody molecules of the invention may be fully human antibodies or chimeric antibodies. Preferably, the antibody molecules are monoclonal, fully human antibodies; more preferably, the antibody molecules are 1H3, 15H12 or 19D12. Preferably, the antibody molecules include one or more of the variable regions and CDRs whose amino acid and nucleotide sequences are set forth in Table 1.

The present invention includes any antibody molecule comprising a CDR selected from:

```
RASQSIGSSLH;         (SEQ ID NO:8)

YASQSLS;             (SEQ ID NO:9)

HQSSRLPHT;           (SEQ ID NO:10)

SFAMH                (SEQ ID NO:14)

GFTFSSFAMH;          (SEQ ID NO:17)

VIDTRGATYYADSVKG;    (SEQ ID NO:15)

LGNFYYGMDV;          (SEQ ID NO:16)

RASQSVSSFLA;         (SEQ ID NO:31)

DASNRAP;             (SEQ ID NO:32)

QQRSNWPRWT;          (SEQ ID NO:33)

GFTFSNYAMH;          (SEQ ID NO:37)

AIGAGGDTYYADSVKG;    (SEQ ID NO:38)
and

GRHRNWYYYNKDY;       (SEQ ID NO:39)

NYAMH                (SEQ ID NO:70)
```

The scope of the present invention includes antibody variable regions of the present invention (e.g., any variable region, mature or unprocessed, indicated in Table 1) linked to any immunoglobulin constant region. If a light chain variable region is linked to a constant region, preferably it is a κ chain. If a heavy chain variable region is linked to a constant region, preferably it is a γ1, γ2, γ3 or γ4 constant region, more preferably, γ1, γ2 or γ4 and even more preferably γ1 or γ4.

The anti-IGFR1 antibody molecules of the invention preferably recognize human IGFR1, preferably sIGFR1; however, the present invention includes antibody molecules which recognize IGFR1 from different species, preferably mammals (e.g., mouse, rat, rabbit, sheep or dog). The present invention also includes anti-IGFR1 antibodies or fragments thereof which are complexed with IGFR1 or any fragment thereof (e.g., amino acids 30-902 of SEQ ID NO: 19) or with any cell which is expressing IGFR1 or any portion or fragment thereof on the cell surface (e.g., HEK293 cells stably transformed with human IGFR1 or MCF7 (e.g., ATCC Cell Line No. HTB-22)). Such complexes may be made by contacting the antibody or antibody fragment with IGFR1 or the IGFR1 fragment.

In a preferred embodiment, fully-human monoclonal antibodies directed against IGFR1 are generated using transgenic mice carrying parts of the human immune system rather than the mouse system. These transgenic mice, which may be referred to, herein, as "HuMAb" mice, contain a human immunoglobulin gene miniloci that encodes unrearranged human heavy (μ and γ) and κ light chain immunoglobulin sequences, together with targeted mutations that inactivate the endogenous μ and κ chain loci (Lonberg, N., et al., (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N., et al., (1994), supra; reviewed in Lonberg, N. (1994) Handbook of Experimental Pharmacology 113:49-101; Lonberg, N., et al., (1995) Intern. Rev. Immunol. 13:65-93, and Harding, F., et al., (1995) Ann. N.Y Acad. Sci 764: 536-546). The preparation of HuMab mice is commonly known in the art and is described, for example, in Taylor, L., et al., (1992) Nucleic Acids Research 20:6287-6295; Chen, J., et al., (1993) International Immunology 5: 647-656; Tuaillon, et al., (1993) Proc. Natl. Acad. Sci USA 90:3720-3724; Choi, et al., (1993) Nature Genetics 4:117-123; Chen, J., et al., (1993) EMBO J. 12: 821-830; Tuaillon, et al., (1994) J Immunol. 152:2912-2920; Lonberg, et al., (1994) Nature 368(6474): 856-859; Lonberg, N. (1994) Handbook of Experimental Pharmacology 113:49-101; Taylor, L., et al., (1994) International Immunology 6: 579-591; Lonberg, N., et al., (1995) Intern. Rev. Immunol. Vol. 13: 65-93; Harding, F., et al., (1995) Ann. N.Y Acad. Sci 764:536-546; Fishwild, D., et al., (1996) Nature Biotechnology 14: 845-851 and Harding, et al., (1995) Annals NY Acad. Sci. 764:536-546; the contents of all of which are hereby incorporated by reference in their entirety. See further, U.S. Pat. Nos. 5,545,806; 5,569,825; 5,625,126; 5,633,425; 5,789,650; 5,877,397; 5,661,016; 5,814,318; 5,874, 299; 5,770,429 and 5,545,807; and International Patent Application Publication Nos. WO 98/24884; WO 94/25585; WO 93/12227; WO 92/22645 and WO 92/03918 the disclosures of all of which are hereby incorporated by reference in their entity.

To generate fully human, monoclonal antibodies to IGFR1, HuMab mice can be immunized with an antigenic IGFR1 polypeptide, preferably amino acids 30-902 of SEQ ID NO: 19, as described by Lonberg, N., et al., (1994) Nature 368 (6474): 856-859; Fishwild, D., et al., (1996) Nature Biotechnology 14: 845-851 and WO 98/24884. Preferably, the mice will be 6-16 weeks of age upon the first immunization. For example, a purified preparation of IGFR1 or sIGFR1 can be used to immunize the HuMab mice intraperitoneally. The mice can also be immunized with whole HEK293 cells which are stably transformed or transfected with an IGFR1 gene. An "antigenic IGFR1 polypeptide" may refer to an IGFR1 polypeptide of any fragment thereof, preferably amino acids 30-902 of SEQ ID NO: 19, which elicits an anti-IGFR1 immune response, preferably in HuMab mice.

In general, HuMAb transgenic mice respond well when initially immunized intraperitoneally (IP) with antigen in complete Freund's adjuvant, followed by every other week IP immunizations (usually, up to a total of 6) with antigen in incomplete Freund's adjuvant. Mice can be immunized, first, with cells expressing IGFR1 (e.g., stably transformed HEK293 cells), then with a soluble fragment of IGFR1 (e.g., amino acids 30-902 of SEQ ID NO: 19) and continually receive alternating immunizations with the two antigens. The immune response can be monitored over the course of the immunization protocol with plasma samples being obtained by retroorbital bleeds. The plasma can be screened for the presence of anti-IGFR1 antibodies, for example by ELISA, and mice with sufficient titers of immunoglobulin can be used for fusions. Mice can be boosted intravenously with antigen 3 days before sacrifice and removal of the spleen. It is expected that 2-3 fusions for each antigen may need to be performed. Several mice can be immunized for each antigen. For example, a total of twelve HuMab mice of the HC07 and HC012 strains can be immunized.

Hybridoma cells which produce the monoclonal, fully human anti-IGFR1 antibodies may be produced by methods which are commonly known in the art. These methods include, but are not limited to, the hybridoma technique originally developed by Kohler, et al., (1975) (Nature 256:495497), as well as the trioma technique (Hering, et al., (1988) Biomed. Biochim. Acta. 47:211-216 and Hagiwara, et al., (1993) Hum. Antibod. Hybridomas 4:15), the human B-cell hybridoma technique (Kozbor, et al., (1983) Immunology Today 4:72 and Cote, et al., (1983) Proc. Natl. Acad. Sci. U.S.A 80:2026-2030), and the EBV-hybridoma technique (Cole, et al., in *Monoclonal Antibodies and Cancer Therapy*, Alan R. Liss, Inc., pp. 77-96, 1985). Preferably, mouse splenocytes are isolated and fused with PEG to a mouse myeloma cell line based upon standard protocols. The resulting hybridomas may then be screened for the production of antigen-specific antibodies. For example, single cell suspensions of splenic lymphocytes from immunized mice may by fused to one-sixth the number of P3X63-Ag8.653 nonsecreting mouse myeloma cells (ATCC, CRL 1580) with 50% PEG. Cells may be plated at approximately $2 \times 10^5$ cells/mL in a flat bottom microtiter plate, followed by a two week incubation in selective medium containing 20% fetal Clone Serum, 18% "653" conditioned media, 5% origen (IGEN), 4 mM L-glutamine, 1 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After two weeks, cells may be cultured in medium in which the HAT is replaced with HT. Individual wells may then be screened by ELISA for human anti-IGFR1 monoclonal IgG antibodies. Once extensive hybridoma growth occurs, medium can be observed usually after 10-14 days. The antibody secreting hybridomas may be replated, screened again, and if still positive for human IgG, anti-IGFR1 monoclonal antibodies, can be subcloned at least twice by limiting dilution. The stable subclones may then be cultured in vitro to generate small amounts of antibody in tissue culture medium for characterization.

The anti-IGFR antibody molecules of the present invention may also be produced recombinantly (e.g., in an *E. coli*/T7 expression system as discussed above). In this embodiment, nucleic acids encoding the antibody molecules of the invention (e.g., $V_H$ or $V_L$) may be inserted into a pET-based plasmid and expressed in the *E. coli*/T7 system. There are several methods by which to produce recombinant antibodies which are known in the art. One example of a method for recombinant production of antibodies is disclosed in U.S. Pat. No. 4,816,567 which is herein incorporated by reference. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740,461 and 4,959,455.

Mammalian cell lines available as hosts for expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the heavy chain or antigen-binding portion thereof, the light chain and/or antigen-binding portion thereof are introduced into mammalian host cells, the antibodies are produced by culturing the host cells for a period of time sufficient to allow for expression of the antibody in the host cells or, more preferably, 5 secretion of the antibody into the culture medium in which the host cells are grown.

Antibodies can be recovered from the culture medium using standard protein purification methods. Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

It is likely that antibodies expressed by different cell lines or in transgenic animals will have different glycosylation from each other. However, all antibodies encoded by the nucleic acid molecules provided herein, or comprising the amino acid sequences provided herein are part of the instant invention, regardless of the glycosylation of the antibodies.

"$K_{off}$" refers to the off-rate constant for dissociation of the antibody from an antibody/antigen complex.

"$K_{on}$" refers to the rate at which the antibody associates with the antigen.

"$K_d$" refers to the dissociation constant of a particular antibody/antigen interaction. $K_d = K_{off}/K_{on}$.

The term "monoclonal antibody," as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Monoclonal antibodies are advantageous in that they may be synthesized by a hybridoma culture, essentially uncontaminated by other immunoglobulins. The modifier "monoclonal" indicates the character of the antibody as being amongst a substantially homogeneous population of antibodies, and is not to be construed as requiring production of the antibody by any particular method. As mentioned above, the monoclonal antibodies to be used in accordance with the present invention may be made by the hybridoma method first described by Kohler, et al., (1975) Nature 256: 495.

A polyclonal antibody is an antibody which was produced among or in the presence of one or more other, non-identical antibodies. In general, polyclonal antibodies are produced from a B-lymphocyte in the presence of several other B-lymphocytes which produced non-identical antibodies. Usually, polyclonal antibodies are obtained directly from an immunized animal.

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai, et al., (1990) Clin. Exp. Immunol. 79: 315-321, Kostelny, et al., (1992) J Immunol. 148:1547-1553. In addition, bispecific antibodies may be formed as "diabodies" (Holliger, et al., (1993) PNAS USA 90:6444-6448) or as "Janusins" (Traunecker, et al., (1991) EMBO J. 10:3655-3659 and Traunecker, et al., (1992) Int. J. Cancer Suppl. 7:51-52).

The term "fully human antibody" refers to an antibody which comprises human immunoglobulin protein sequences only. A fully human antibody may contain murine carbohydrate chains if produced in a mouse, in a mouse cell or in a hybridoma derived from a mouse cell. Similarly, "mouse antibody" refers to an antibody which comprises mouse immunoglobulin sequences only.

The present invention includes "chimeric antibodies"—an antibody which comprises a variable region of the present invention fused or chimerized with an antibody region (e.g., constant region) from another, non-human species (e.g., mouse, horse, rabbit, dog, cow, chicken). These antibodies may be used to modulate the expression or activity of IGFR1 in the non-human species.

"Single-chain Fv" or "sFv" antibody fragments have the $V_H$ and $V_L$ domains of an antibody, wherein these domains are present in a single polypeptide chain. Generally, the sFv polypeptide further comprises a polypeptide linker between the $V_H$ and $V_L$ domains which enables the sFv to form the desired structure for antigen binding. Techniques described for the production of single chain antibodies (U.S. Pat. Nos. 5,476,786; 5,132,405 and 4,946,778) can be adapted to produce anti-IGFR1-specific single chain antibodies. For a review of sFv see Pluckthun in *The Pharmacology of Monoclonal Antibodies*, vol. 113, Rosenburg and Moore eds. Springer-Verlag, N.Y., pp. 269-315 (1994).

"Disulfide stabilized Fv fragments" and "dsFv" refer to antibody molecules comprising a variable heavy chain ($V_H$) and a variable light chain ($V_L$) which are linked by a disulfide bridge.

Antibody fragments within the scope of the present invention also include $F(ab)_2$ fragments which may be produced by enzymatic cleavage of an IgG by, for example, pepsin. Fab fragments may be produced by, for example, reduction of $F(ab)_2$ with dithiothreitol or mercaptoethylamine. A Fab fragment is a $V_L$-$C_L$ chain appended to a $V_H$-$C_{H1}$ chain by a disulfide bridge. A $F(ab)_2$ fragment is two Fab fragments which, in turn, are appended by two disulfide bridges. The Fab portion of an $F(ab)_2$ molecule includes a portion of the $F_c$ region between which disulfide bridges are located.

An $F_v$ fragment is a $V_L$ or $V_H$ region.

Depending on the amino acid sequences of the constant domain of their heavy chains, immunoglobulins can be assigned to different classes. There are at least five major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2.

The anti-IGFR1 antibody molecules of the invention may also be conjugated to a chemical moiety. The chemical moiety may be, inter alia, a polymer, a radionuclide or a cytotoxic factor. Preferably the chemical moiety is a polymer which increases the half-life of the antibody molecule in the body of a subject. Suitable polymers include, but are not limited to, polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (Bioconj. Chem. 10:973-981) discloses PEG conjugated single-chain antibodies. Wen, et al., (2001) (Bioconj. Chem. 12:545-553) disclose conjugating antibodies with PEG which is attached to a radiometal chelator (diethylenetriaminpentaacetic acid (DTPA)).

The antibodies and antibody fragments of the invention may also be conjugated with labels such as $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fe, $^{57}$Se, $^{152}$Eu, $^{67}$CU, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr and $^{56}$Fe.

The antibodies and antibody fragments of the invention may also be conjugated with fluorescent or chemilluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The antibody molecules may also be conjugated to a cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *momordica charantia* inhibitor, curcin, crotin, *saponaria officinalis* inhibitor, mitogellin, restrictocin, phenomycin, and enomycin.

Any method known in the art for conjugating the antibody molecules of the invention to the various moieties may be employed, including those methods described by Hunter, et al., (1962) Nature 144:945; David, et al., (1974) Biochemistry 13:1014; Pain, et al., (1981) J. Immunol. Meth. 40:219; and Nygren, J., (1982) Histochem. and Cytochem. 30:407. Methods for conjugating antibodies are conventional and very well known in the art.

Modified Antibody Molecules

The present invention includes antibodies and antigen-binding fragments (e.g., fully-human antibodies, SFv, dsFv, Fv, chimeric antibodies) comprising a light chain of SEQ ID NOs: 41, 43, 72, 74, 76 or 78 (15H12/19D12 LCA, LCB, LCC, LCD, LCE or LCF); preferably amino acids 20-128 of SEQ ID NOs: 41, 43, 72, 74, 76 or 78 (mature 15H12/19D12 LCA, LCB, LCC, LCD, LCE or LCF). The present invention also includes antibody molecules including the heavy chain of SEQ ID NO: 45 or 112 (15H12/19D12 HCA, HCB); preferably amino acids 20-137 of SEQ ID NO: 45 or 112 (mature 15H12/19D12 HCA, HCB).

The 15H12/19D12 LCA, LCB, LCC, LCD, LCE and LCF may be dimerized with any other immunoglobulin heavy chain, preferably an immunoglobulin heavy chain of the present invention. Likewise, 15H12/19D12 HCA or HCB may be dimerized with any light chain, preferably a light chain of the present invention. For example, 15H12/19D12 HCA or HCB may be dimerized with 15H12/19D12 LCC, LCD, LCE or LCF.

Antibodies and antigen-binding fragments comprising 15H12/19D12 LCA, 15H12/19D12 LCB, 15H12/19D12 LCC, 15H12/19D12 LCD, 15H12/19D12 LCE, 15H12/19D12 LCF, 15H12/19D12 HCA or 15H12/19D12 HCB or any fragment thereof exhibit minimal immunogenicity in a human subject; thereby, leading to a low incidence of HAHA response when administered to a human subject.

Preferred antibody chains are shown below. Dotted underscored type encodes the signal peptide. Solid underscored type encodes the CDRs. Plain type encodes the framework regions. Most preferably, the antibody chains are mature fragments which lack the signal peptide.

Modified 19D12/15H12 Light Chain-C (SEQ ID NO:71)
ATG TCG CCA TCA CAA CTC ATT GGG TTT CTG CTG CTC -continued

```
TGG GTT CCA GCC TCC AGG GGT GAA ATT GTG CTG ACT
----------------------------
CAG AGC CCA GAC TCT CTG TCT GTG ACT CCA GGC GAG
AGA GTC ACC ATC ACC TGC CGG GCC AGT CAG AGC ATT
GGT AGT AGC TTA CAC TGG TAC CAG CAG AAA CCA GGT
CAG TCT CCA AAG CTT CTC ATC AAG TAT GCA TCC CAG
TCC CTC TCA GGG GTC CCC TCG AGG TTC AGT GGC AGT
GGA TCT GGG ACA GAT TTC ACC CTC ACC ATC AGT AGC
CTC GAG GCT GAA GAT GCT GCA GCG TAT TAC TGT CAT
CAG AGT AGT CGT TTA CCT CAC ACT TTC GGC CAA GGG
ACC AAG GTG GAG ATC AAA CGT ACG
```

(SEQ ID NO:72)
```
M   S   P   S   Q   L   I   G   F   L   L   L   W
---------------------------------------------------
V   P   A   S   R   G   E   I   V   L   T   Q   S
---------------------
P   D   S   L   S   V   T   P   G   E   R   V   T
I   T   C   R   A   S   Q   S   I   G   S   S   L
H   W   Y   Q   Q   K   P   G   Q   S   P   K   L
L   I   K   Y   A   S   Q   S   L   S   G   V   P
S   R   F   S   G   S   G   S   G   T   D   F   T
L   T   I   S   S   L   E   A   E   D   A   A   A
Y   Y   C   H   Q   S   S   R   L   P   H   T   F
G   Q   G   T   K   V   E   I   K   R   T
```

Modified 19D12/15H12 Light Chain-D (SEQ ID NO:73)
```
ATG TCG CCA TCA CAA CTC ATT GGG TTT CTG CTG CTC
----------------------------------------------
TGG GTT CCA GCC TCC AGG GGT GAA ATT GTG CTG ACT
----------------------------
CAG AGC CCA GAC TCT CTG TCT GTG ACT CCA GGC GAG
AGA GTC ACC ATC ACC TGC CGG GCC AGT CAG AGC ATT
GGT AGT AGC TTA CAC TGG TAC CAG CAG AAA CCA GGT
CAG TCT CCA AAG CTT CTC ATC AAG TAT GCA TCC CAG
TCC CTC TCA GGG GTC CCC TCG AGG TTC AGT GGC AGT
GGA TCT GGG ACA GAT TTC ACC CTC ACC ATC AGT AGC
CTC GAG GCT GAA GAT GCT GCA GTG TAT TAC TGT CAT
CAG AGT AGT CGT TTA CCT CAC ACT TTC GGC CAA GGG
ACC AAG GTG GAG ATC AAA CGT ACG
```

(SEQ ID NO:74)
```
M   S   P   S   Q   L   I   G   F   L   L   L   W
---------------------------------------------------
V   P   A   S   R   G   E   I   V   L   T   Q   S
---------------------
P   D   S   L   S   V   T   P   G   E   R   V   T
I   T   C   R   A   S   Q   S   I   G   S   S   L
H   W   Y   Q   Q   K   P   G   Q   S   P   K   L
L   I   K   Y   A   S   Q   S   L   S   G   V   P
S   R   F   S   G   S   G   S   G   T   D   F   T
L   T   I   S   S   L   E   A   E   D   F   A   V
Y   Y   C   H   Q   S   S   R   L   P   H   T   F
G   Q   G   T   K   V   E   I   K   R   T
```

Modified 19D12/15H12 Light Chain-E (SEQ ID NO:75)
```
ATG TCG CCA TCA CAA CTC ATT GGG TTT CTG CTG CTC
----------------------------------------------
TGG GTT CCA GCC TCC AGG GGT GAA ATT GTG CTG ACT
----------------------------
CAG AGC CCA GGT ACC CTG TCT GTG TCT CCA GGC GAG
AGA GCC ACC CTC TCC TGC CGG GCC AGT CAG AGC ATT
GGT AGT AGC TTA CAC TGG TAC CAG CAG AAA CCA GGT
CAG GCT CCA AGG CTT CTC ATC AAG TAT GCA TCC CAG
TCC CTC TCA GGG ATC CCC GAT AGG TTC AGT GGC AGT
GGA TCT GGG ACA GAT TTC ACC CTC ACC ATC AGT AGA
CTG GAG CCT GAA GAT GCT GCA GCG TAT TAC TGT CAT
CAG AGT AGT CGT TTA CCT CAC ACT TTC GGC CAA GGG
ACC AAG GTG GAG ATC AAA CGT ACA
```

(SEQ ID NO:76)
```
M   S   P   S   Q   L   I   G   F   L   L   L   W
---------------------------------------------------
V   P   A   S   R   G   E   I   V   L   T   Q   S
---------------------
P   G   T   L   S   V   S   P   G   E   R   A   T
L   S   C   R   A   S   Q   S   I   G   S   S   L
H   W   Y   Q   Q   K   P   G   Q   A   P   R   L
L   I   K   Y   A   S   Q   S   L   S   G   I   P
D   R   F   S   G   S   G   S   G   T   D   F   T
L   T   I   S   R   L   E   P   E   D   A   A   A
Y   Y   C   H   Q   S   S   R   L   P   H   T   F
G   Q   G   T   K   V   E   I   K   R   T
```

Modified 19D12/15H12 Light Chain-F (SEQ ID NO:77)
```
ATG TCG CCA TCA CAA CTC ATT GGG TTT CTG CTG CTC
----------------------------------------------
TGG GTT CCA GCC TCC AGG GGT GAA ATT GTG CTG ACT
----------------------------
CAG AGC CCA GGT ACC CTG TCT GTG TCT CCA GGC GAG
AGA GCC ACC CTC TCC TGC CGG GCC AGT CAG AGC ATT
GGT AGT AGC TTA CAC TGG TAC CAG CAG AAA CCA GGT
CAG GCT CCA AGG CTT CTC ATC AAG TAT GCA TCC CAG
```

```
                                             -continued
TCC CTC TCA GGG ATC CCC GAT AGG TTC AGT GGC AGT

GGA TCT GGG ACA GAT TTC ACC CTC ACC ATC AGT AGA

CTG GAG CCT GAA GAT TTC GCA GTG TAT TAC TGT CAT

CAG AGT AGT CGT TTA CCT CAC ACT TTC GGC CAA GGG

ACC AAG GTG GAG ATC AAA CGT ACA (SEQ ID NO:78)
M   S   P   S   Q   L   I   G   F   L   L   L   W
----------------------------------------------------
V   P   A   S   R   G   E   I   V   L   T   Q   S
----------------------

P   G   T   L   S   V   S   P   G   E   R   A   T

L   S   C   R   A   S   Q   S   I   G   S   S   L

H   W   Y   Q   Q   K   P   G   Q   A   P   R   L

L   I   K   Y   A   S   Q   S   L   S   G   I   P

D   R   F   S   G   S   G   S   G   T   D   F   T

L   T   I   S   R   L   E   P   E   D   F   A   V

Y   Y   C   H   Q   S   S   R   L   P   H   T   F

G   Q   G   T   K   V   E   I   K   R   T

Modified 19D12/15H12 heavy chain-A
                                            (SEQ ID NO:44)
ATG GAG TTT GGG CTG AGC TGG GTT TTC CTT GTT GCT
-------------------------------------------------

ATA TTA AAA GGT GTC CAG TGT GAG GTT CAG CTG GTG
--------------------------

CAG TCT GGG GGA GGC TTG GTA AAG CCT GGG GGG TCC

CTG AGA CTC TCC TGT GCA GCC TCT GGA TTC ACC TTC

AGT AGC TTT GCT ATG CAC TGG GTT CGC CAG GCT CCA

GGA AAA GGT CTG GAG TGG ATA TCA GTT ATT GAT ACT

CGT GGT GCC ACA TAC TAT GCA GAC TCC GTG AAG GGC

CGA TTC ACC ATC TCC AGA GAC AAT GCC AAG AAC TCC

TTG TAT CTT CAA ATG AAC AGC CTG AGA GCC GAG GAC

ACT GCT GTG TAT TAC TGT GCA AGA CTG GGG AAC TTC

TAC TAC GGT ATG GAC GTC TGG GGC CAA GGG ACC ACG

GTC ACC GTC TCC TCA
                                            (SEQ ID NO:45)
Met Glu Phe Gly Leu Ser Trp Val Phe Leu Val Ala
-------------------------------------------------

Ile Leu Lys Gly Val Gln Cys Glu Val Gln Leu Val
--------------------------

Gln Ser Gly Gly Gly Leu Val Lys Pro Gly Gly Ser

Leu Arg Leu Ser Cys Ala Ala Ser Gly Phe Thr Phe

Ser Ser Phe Ala Met His Trp Val Arg Gln Ala Pro

Gly Lys Gly Leu Glu Trp Ile Ser Val Ile Asp Thr

Arg Gly Ala Thr Tyr Tyr Ala Asp Ser Val Lys Gly

Arg Phe Thr Ile Ser Arg Asp Asn Ala Lys Asn Ser

-continued
Leu Tyr Leu Gln Met Asn Ser Leu Arg Ala Glu Asp

Thr Ala Val Tyr Tyr Cys Ala Arg Leu Gly Asn Phe

Tyr Tyr Gly Met Asp Val Trp Gly Gln Gly Thr Thr

Val Thr Val Ser Ser

Modified 19D12/15H12 heavy chain-B
                                           (SEQ ID NO:111)
ATG GAG TTT GGG CTG AGC TGG GTT TTC CTT GTT GCT
-------------------------------------------------

ATA TTA AAA GGT GTC CAG TGT GAG GTT CAG CTG GTG
--------------------------

CAG TCT GGG GGA GGC TTG GTA CAG CCC GGG GGG TCC

CTG AGA CTC TCC TGT GCA GCC TCT GGA TTC ACC TTC

AGT AGC TTT GCT ATG CAC TGG GTT CGC CAG GCT CCA

GGA AAA GGT CTG GAG TGG ATA TCA GTT ATT GAT ACT

CGT GGT GCC ACA TAC TAT GCA GAC TCC GTG AAG GGC

CGA TTC ACC ATC TCC AGA GAC AAT GCC AAG AAC TCC

TTG TAT CTT CAA ATG AAC AGC CTG AGA GCC GAG GAC

ACT GCT GTG TAT TAC TGT GCA AGA CTG GGG AAC TTC

TAC TAC GGT ATG GAC GTC TGG GGC CAA GGG ACC ACG

GTC ACC GTC TCC TCA
                                           (SEQ ID NO:112)
Met Glu Phe Gly Leu Ser Trp Val Phe Leu Val Ala
-------------------------------------------------

Ile Leu Lys Gly Val Gln Cys Glu Val Gln Leu Val
--------------------------

Gln Ser Gly Gly Gly Leu Val Gln Pro Gly Gly Ser

Leu Arg Leu Ser Cys Ala Ala Ser Gly Phe Thr Phe

Ser Ser Phe Ala Met His Trp Val Arg Gln Ala Pro

Gly Lys Gly Leu Glu Trp Ile Ser Val Ile Asp Thr

Arg Gly Ala Thr Tyr Tyr Ala Asp Ser Val Lys Gly

Arg Phe Thr Ile Ser Arg Asp Asn Ala Lys Asn Ser

Leu Tyr Leu Gln Met Asn Ser Leu Arg Ala Glu Asp

Thr Ala Val Tyr Tyr Cys Ala Arg Leu Gly Asn Phe

Tyr Tyr Gly Met Asp Val Trp Gly Gln Gly Thr Thr

Val Thr Val Ser Ser
```

Gene Therapy

The anti-IGFR1 antibodies of the invention may also be administered to a subject in a gene therapy approach. In a gene therapy approach, the cells of a subject are transformed with nucleic acids which encode the antibodies of the invention. Subjects comprising the nucleic acids will then produce the antibody molecules endogenously. Previously, Alvarez, et al., (2000) (Clinical Cancer Research 6:3081-3087) introduced single-chain anti-ErbB2 antibodies to subjects using a gene therapy approach. The methods disclosed by Alvarez, et al., may be easily adapted for the introduction of nucleic acids encoding an anti-IGFR1 antibody molecule of the invention to a subject.

Although nucleic acids encoding any polypeptide or antibody molecule of the invention may be introduced to a subject, in preferred embodiments, the antibody molecule is a fully human, single-chain antibody.

The nucleic acids may be introduced to the cells of a subject by any means known in the art. In preferred embodiments, the nucleic acids are introduced as part of a viral vector. Examples of preferred viruses from which the vectors may be derived include lentiviruses, herpes viruses, adenoviruses, adeno-associated viruses, vaccinia virus, baculovirus, alphavirus, influenza virus, and other recombinant viruses with desirable cellular tropism.

Various companies produce viral vectors commercially, including, but by no means limited to, Avigen, Inc. (Alameda, Calif.; MV vectors), Cell Genesys (Foster City, Calif.; retroviral, adenoviral, MV vectors, and lentiviral vectors), Clontech (retroviral and baculoviral vectors), Genovo, Inc. (Sharon Hill, Pa.; adenoviral and MV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Methods for constructing and using viral vectors are known in the art (see, e.g., Miller, et al., (1992) BioTechniques 7:980-990). Preferably, the viral vectors are replication defective, that is, they are unable to replicate autonomously, and thus are not infectious, in the target cell. Preferably, the replication defective virus is a minimal virus, i.e., it retains only the sequences of its genome which are necessary for encapsidating the genome to produce viral particles. Defective viruses, which entirely or almost entirely lack viral genes, are preferred. Use of defective viral vectors allows for administration to cells in a specific, localized area, without concern that the vector can infect other cells. Thus, a specific tissue can be specifically targeted.

Examples of vectors comprising attenuated or defective DNA virus sequences include, but are not limited to, a defective herpes virus vector (Kanno, et al., (1999) Cancer Gen. Ther. 6:147-154; Kaplitt, et al., (1997) J. Neurosci. Meth. 71:125-132 and Kaplitt, et al., (1994) J. Neuro Onc. 19:137-147).

Adenoviruses are eukaryotic DNA viruses that can be modified to efficiently deliver a nucleic acid of the invention to a variety of cell types. Attenuated adenovirus vectors, such as the vector described by Strafford-Perricaudet, et al., (1992) (J. Clin. Invest. 90:626-630) are desirable in some instances. Various replication defective adenovirus and minimum adenovirus vectors have been described (PCT Publication Nos. WO94/26914, WO94/28938, WO94/28152, WO94/12649, WO95/02697 and WO96/22378). The replication defective recombinant adenoviruses according to the invention can be prepared by any technique known to a person skilled in the art (Levrero, et al., (1991) Gene 101:195; EP 185573; Graham, (1984) EMBO J. 3:2917; Graham, et al., (1977) J. Gen. Virol. 36:59).

The adeno-associated viruses (MV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The use of vectors derived from the AAVs for transferring genes in vitro and in vivo has been described (see Daly, et al., (2001) Gene Ther. 8:1343-1346, 1245-1315; Larson, et al., (2001) Adv. Exp. Med. Bio. 489:45-57; PCT Publication Nos. WO91/18088 and WO93/09239; U.S. Pat. Nos. 4,797,368 and 5,139,941 and EP 488528B1).

In another embodiment, the gene can be introduced in a retroviral vector, e.g., as described in U.S. Pat. Nos. 5,399,346, 4,650,764, 4,980,289, and 5,124,263; Mann, et al., (1983) Cell 33:153; Markowitz, et al., (1988) J. Virol., 62:1120; EP 453242 and EP178220. The retroviruses are integrating viruses which infect dividing cells.

Lentiviral vectors can be used as agents for the direct delivery and sustained expression of nucleic acids encoding an antibody molecule of the invention in several tissue types, including brain, retina, muscle, liver and blood. The vectors can efficiently transduce dividing and nondividing cells in these tissues, and maintain long-term expression of the antibody molecule. For a review, see Zufferey, et al., (1998) J. Virol. 72:9873-80 and Kafri, et al., (2001) Curr. Opin. Mol. Ther. 3:316-326. Lentiviral packaging cell lines are available and known generally in the art. They facilitate the production of high-titer lentivirus vectors for gene therapy. An example is a tetracycline-inducible VSV-G pseudotyped lentivirus packaging cell line which can generate virus particles at titers greater than 106 IU/ml for at least 3 to 4 days; see Kafri, et al., (1999) (J. Virol. 73: 576-584). The vector produced by the inducible cell line can be concentrated as needed for efficiently transducing nondividing cells in vitro and in vivo.

Sindbis virus is a member of the alphavirus genus and has been studied extensively since its discovery in various parts of the world beginning in 1953. Gene transduction based on alphavirus, particularly Sindbis virus, has been well-studied in vitro (see Straus, et al., (1994) Microbiol. Rev., 58:491-562; Bredenbeek, et al., (1993) J. Virol., 67; 6439-6446 Iijima, et al., (1999) Int. J. Cancer 80:110-118 and Sawai, et al., (1998) Biochim. Biophyr. Res. Comm. 248:315-323). Many properties of alphavirus vectors make them a desirable alternative to other virus-derived vector systems being developed, including rapid engineering of expression constructs, production of high-titered stocks of infectious particles, infection of nondividing cells, and high levels of expression (Strauss, et al., (1994) Microbiol. Rev. 58:491-562). Use of Sindbis virus for gene therapy has been described. (Wahlfors, et al., (2000) Gene. Ther. 7:472-480 and Lundstrom (1999) J. Recep. Sig. Transduct. Res. 19(1-4):673-686).

In another embodiment, a vector can be introduced to cells by lipofection or with other transfection facilitating agents (peptides, polymers, etc.). Synthetic cationic lipids can be used to prepare liposomes for in vivo and in vitro transfection of a gene encoding a marker (Felgner, et al., (1987) Proc. Natl. Acad. Sci. USA 84:7413-7417 and Wang, et al., (1987) Proc. Natl. Acad. Sci. USA 84:7851-7855). Useful lipid compounds and compositions for transfer of nucleic acids are described in PCT Publication Nos. WO 95/18863 and WO96/17823, and in U.S. Pat. No. 5,459,127.

It is also possible to introduce the vector in vivo as a naked DNA plasmid. Naked DNA vectors for gene therapy can be introduced into the desired host cells by methods known in the art, e.g., electroporation, microinjection, cell fusion, DEAE dextran, calcium phosphate precipitation, use of a gene gun, or use of a DNA vector transporter (see, e.g., Wilson, et al., (1992) J. Biol. Chem. 267:963-967; Williams, et al., (1991) Proc. Natl. Acad. Sci. USA 88:2726-2730). Receptor-mediated DNA delivery approaches can also be used (Wu, et al., (1988) J. Biol. Chem. 263:14621-14624). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Vilquin, et al., (2001) Gene Ther. 8:1097; Payen, et al., (2001) Exp. Hematol. 29:295-300; Mir (2001) Bioelectrochemistry 53:1-10; PCT Publication Nos. WO99/01157, WO99/01158 and WO99/01175).

Pharmaceutical Compositions

An antibody or antigen-binding fragment of the invention can be incorporated into a pharmaceutical composition, along with a pharmaceutically acceptable carrier, suitable for administration to a subject in vivo. Although the scope of the present invention includes pharmaceutical compositions which may be administered to a subject by any route (e.g., oral, ocular, topical or pulmonary (inhalation)), administration by a parenteral route such as intratumoral injection, intravenous injection, subcutaneous injection or intramuscular injection is preferred. In a preferred embodiment, the pharmaceutical compositions of the invention comprise 1H3, 15H12, 19D12, 15H12/19D12 LCA, 15H12/19D12 LCB, 15H12/19D12 LCC, 15H12/19D12 LCD, 15H12/19D12 LCE, 15H12/19D12 LCF, 15H12/19D12 HCA or 15H12/19D12 HCB and a pharmaceutically acceptable carrier.

For general information concerning formulations, see, e.g., Gilman, et al., (eds.) (1990), *The Pharmacological Bases of Therapeutics,* 8th Ed., Pergamon Press; A. Gennaro (ed.), *Remington's Pharmaceutical Sciences,* 18th Edition, (1990), Mack Publishing Co., Easton, Pa.; Avis, et al., (eds.) (1993) *Pharmaceutical Dosage Forms: Parenteral Medications* Dekker, New York; Lieberman, et al., (eds.) (1990) *Pharmaceutical Dosage Forms: Tablets* Dekker, New York; and Lieberman, et al., (eds.) (1990), *Pharmaceutical Dosage Forms: Disperse Systems* Dekker, New York, Kenneth A. Walters (ed.) (2002) *Dermatological and Transdermal Formulations* (*Drugs and the Pharmaceutical Sciences*), Vol 119, Marcel Dekker.

Pharmaceutically acceptable carriers are conventional and very well known in the art. Examples include aqueous and nonaqueous carriers, stabilizers, antioxidants, solvents, dispersion media, coatings, antimicrobial agents, buffers, serum proteins, isotonic and absorption delaying agents, and the like that are physiologically compatible. Preferably, the carrier is suitable for injection into a subject's body.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Stabilizers, such as $\alpha,\alpha$-trehalose dihydrate may be included for stabilizing the antibody molecules of the invention from degrading effects of dessication or freeze-drying.

Examples of pharmaceutically-acceptable antioxidants include: water soluble antioxidants such as ascorbic acid, cysteine hydrochloride, sodium bisulfate, sodium metabisulfite, sodium sulfite and the like; and oil-soluble antioxidants such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Prevention of the presence of microorganisms may be ensured both by sterilization procedures, and by the inclusion of various antimicrobial agents such as EDTA, EGTA, paraben, chlorobutanol, phenol sorbic acid, and the like.

Suitable buffers which may be included in the pharmaceutical compositions of the invention include L-histidine based buffers, phosphate based buffers (e.g., phosphate buffered saline, pH≈7), sorbate based buffers or glycine-based buffers.

Serum proteins which may be included in the pharmaceutical compositions of the invention may include human serum albumin.

Isotonic agents, such as sugars, ethanol, polyalcohols (e.g., glycerol, propylene glycol, liquid polyethylene glycol, mannitol or sorbitol), sodium citrate or sodium chloride (e.g., buffered saline) may also be included in the pharmaceutical compositions of the invention.

Prolonged absorption of an injectable pharmaceutical form may be brought about by the inclusion of agents which delay absorption such as aluminum monostearate and/or gelatin.

Dispersions can also be prepared in glycerol, liquid polyethylene glycols, and mixtures thereof and in oils.

Pharmaceutically acceptable carriers include sterile aqueous solutions or dispersions and sterile powders for the extemporaneous preparation of sterile injectable solutions or dispersions. The use of such media and agents for pharmaceutically active substances is well known in the art.

Sterile injectable solutions can be prepared by incorporating the antibody or antigen-binding fragment of the invention in the required amount in an appropriate solvent, optionally with one or a combination of ingredients enumerated above, as required, followed by sterilization microfiltration. Generally, dispersions are prepared by incorporating the antibody molecule into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional, desired ingredient from a previously sterile-filtered solution thereof.

The antibody or antigen-binding fragment of the invention may also be orally administered. Pharmaceutical compositions for oral administration may contain, in addition to the binding composition, additives such as starch (e.g., potato, maize or wheat starch or cellulose), starch derivatives (e.g., microcrystalline cellulose or silica), sugars (e.g., lactose), talc, stearate, magnesium carbonate or calcium phosphate. In order to ensure that oral compositions comprising an antibody or antigen-binding fragment of the invention are well tolerated by the patient's digestive system, mucus formers or resins may be included. It may also be desirable to improve tolerance by formulating the antibody or antigen-binding fragment in a capsule which is insoluble in the gastric juices. An exemplary pharmaceutical composition of this invention in the form of a capsule is prepared by filling a standard two-piece hard gelatin capsule with the antibody or antigen-binding fragment of the invention in powdered form, lactose, talc and magnesium stearate. Oral administration of immunoglobulins has been described (Foster, et al., (2001) Cochrane Database System rev. 3:CD001816)

An antibody or antigen-binding fragment of the invention may also be included in a pharmaceutical composition for topical administration. Formulations suitable for topical administration include liquid or semi-liquid preparations suitable for penetration through the skin to the site where treatment is required, such as liniments, lotions, creams, ointments or pastes, and drops suitable for administration to the eye, ear or nose.

Drops according to the present invention may comprise sterile aqueous or oily solutions or suspensions and may be prepared by dissolving the antibody or antigen-binding fragment in a suitable aqueous solution of a bactericidal and/or fungicidal agent and/or any other suitable preservative, and preferably including a surface active agent. The resulting solution may then be clarified by filtration.

Lotions according to the present invention include those suitable for application to the skin or eye. An eye lotion may comprise a sterile, aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the antibody or antigen-binding fragment of the invention in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

The antibodies and antigen-binding fragments of the invention may also be administered by inhalation. A suitable pharmaceutical composition for inhalation may be an aerosol. An exemplary pharmaceutical composition for inhalation of an antibody or antigen-binding fragment of the invention may include: an aerosol container with a capacity of 15-20 ml comprising the antibody or antigen-binding fragment of the invention, a lubricating agent, such as polysorbate 85 or oleic acid, dispersed in a propellant, such as freon, preferably in a combination of 1,2-dichlorotetrafluoroethane and difluorochloromethane. Preferably, the composition is in an appropriate aerosol container adapted for either intranasal or oral inhalation administration.

In yet another embodiment of the present invention, the pharmaceutical composition can be administered by combination therapy. For example, the combination therapy can include a pharmaceutical composition of the present invention in association with one or more anti-cancer therapeutic agents (e.g., alkylating agents, antimetabolites, anti-tumor antibiotics, mitotic inhibitors, chromatin function inhibitors, anti-angiogenesis agents, anti-estrogens, anti-androgens, antibody therapies or immunomodulators). An "anti-cancer therapeutic agent" is a substance which, when administered to a subject, treats or prevents the development of cancer in the subject's body. The compositions of the invention may be administered in association with one or more anti-cancer therapeutic procedures (e.g., radiation therapy or surgical tumorectomy). An "anti-cancer therapeutic procedure" is a process which is performed on a subject which treats or reduces the incidence of cancer in the subject. When a combination therapy is used, the antibodies or antigen-binding fragments of the invention, or pharmaceutical compositions thereof, may be formulated into a single composition for simultaneous delivery or formulated separately into two or more compositions (e.g., a kit). Furthermore, the antibody or antigen-binding fragment may be administered to a subject at a different time than when the other therapeutic agent or therapeutic procedure is administered; for example, each administration may be given non-simultaneously at several intervals over a given period of time.

"Alkylating agent" refers to any substance which can cross-link or alkylate any molecule, preferably nucleic acid (e.g., DNA), within a cell. Examples of alkylating agents include mechlorethamine, cyclophosphamide, ifosfamide, phenylalanine mustard, melphalen, chlorambucol, uracil mustard, estramustine, thiotepa, busulfan, lomustine, carmustine, streptozocin, dacarbazine, cis-platinum, carboplatin and altretamine.

"Antimetabolites" refer to substances that block cell growth and/or metabolism by interfering with certain activities, usually DNA synthesis. Examples of antimetabolites include methotrexate, 5-fluoruracil, floxuridine, 5-fluorodeoxyuridine, capecitabine, fludarabine, cytosine arabinoside, 6-mercaptopurine, 6-thioguanine, gemcitabine, cladribine, deoxycoformycin and pentostatin.

"Anti-tumor antibiotics" refer to compounds which may prevent or inhibit DNA, RNA and/or protein synthesis. Examples of anti-tumor antibiotics include doxorubicin, daunorubicin, idarubicin, valrubicin, mitoxantrone, dactinomycin, mithramycin, plicamycin, mitomycin C, bleomycin, and procarbazine.

"Mitotic inhibitors" prevent normal progression of the cell cycle and mitosis. In general, microtubule inhibitors such as paclitaxel and docetaxel are capable of inhibiting mitosis. Vinca alkaloids such as vinblastine, vincristine and vinorelbine are also capable of inhibiting mitosis.

"Chromatin function inhibitors" refer to substances which inhibit the normal function of chromatin modeling proteins such as topoisomerase I or topoisomerase II. Examples of chromatin function inhibitors include topotecan, irinotecan, etoposide and teniposide.

"Anti-angiogenesis agent" refers to any drug, compound, substance or agent which inhibits growth of blood vessels. Exemplary anti-angiogenesis agents include, but are by no means limited to, razoxin, marimastat, COL-3, neovastat, BMS-275291, thalidomide, squalamine, endostatin, SU5416, SU6668, interferon-alpha, EMD121974, interleukin-12, IM862, angiostatin and vitaxin.

"Anti-estrogen" or "anti-estrogenic agent" refer to any substance which reduces, antagonizes or inhibits the action of estrogen. Examples of anti-estrogen agents are tamoxifen, toremifene, raloxifene, droloxifene, iodoxyfene, anastrozole, letrozole, and exemestane.

"Anti-androgens" or "anti-androgen agents" refer to any substance which reduces, antagonizes or inhibits the action of an androgen. Examples of anti-androgens are flutamide, nilutamide, bicalutamide, sprironolactone, cyproterone acetate, finasteride and cimitidine.

Antibody therapies which may be administered in conjunction with the antibodies or antigen-binding fragments of the invention include trastuzumab (e.g., herceptin) (see, for example, Sliwkowski, et al., (1999) Semin. Oncol. 26(4 Suppl 12):60-70), vitaxin and rituximab.

"Immunomodulators" are substances which stimulate the immune system. Examples of immunomodulators include denileukin diftitox, levamisole in conjunction with 5-fluorouracil, interferon and interleukin-2.

"Radiotherapy" or "radiation therapy" refers to treating a disease, such as cancer, by administration of ionizing radiation (preferably to a tumor site). Examples of ionizing radiation which may be administered include X-rays, gamma rays (e.g., emitted by radium, uranium or cobalt 60), and particle beam radiation (e.g., protons, neutrons, pions or heavy ions).

Dosage

Preferably, an antibody or antigen-binding fragment of the invention is administered to a subject at a "therapeutically effective dosage" which preferably inhibits a disease or condition which is mediated by IGFR1 (e.g., tumor growth) to any extent-preferably by at least about 20%, more preferably by at least about 40%, even more preferably by at least about 60%, and still more preferably by at least about 80%-100% relative to untreated subjects. The ability of an antibody or antigen-binding fragment of the invention to inhibit cancer can be evaluated in an animal model system predictive of efficacy in human tumors. Alternatively, this property of a composition can be evaluated by examining the ability of an antibody or antigen-binding fragment of the invention to inhibit tumor cell growth in vitro by assays (see below) well-known to the skilled practitioner. One of ordinary skill in the art would be able to determine such amounts based on such factors as the subject's size, the severity of the subject's symptoms, and the particular composition or route of administration selected.

Dosage regimens may be adjusted to provide the optimum desired response (e.g., a therapeutic response). For example, a single bolus may be administered, several divided doses may be administered over time or the dose may be proportionally reduced or increased as indicated by exigencies of the therapeutic situation. It is especially advantageous to formulate parenteral compositions in dosage unit form for ease of administration and uniformity of dosage.

A physician or veterinarian having ordinary skill in the art can readily determine and prescribe the effective amount of the pharmaceutical composition required. For example, the physician or veterinarian could start doses of the antibody or antigen-binding fragment of the invention employed in the pharmaceutical composition at levels lower than that required in order to achieve the desired therapeutic effect and gradually increase the dosage until the desired effect is achieved. In general, a suitable daily dose of a composition of the invention may be that amount of the compound which is the lowest dose effective to produce a therapeutic effect. Such an effective dose will generally depend upon the factors described above. It is preferred that administration be by injection, preferably proximal to the site of the target (e.g., tumor). If desired, the effective daily dose of a pharmaceutical composition may be administered as two, three, four, five, six or more subdoses administered separately at appropriate intervals throughout the day.

Therapeutic Methods and Administration

The antibodies or antigen-binding fragments of the invention and pharmaceutical compositions comprising the antibodies or antigen-binding fragments of the invention may be used for treating or preventing any disease or condition in a subject which is mediated by elevated expression or activity of IGFR1 or by elevated expression of its ligand (e.g., IGF-I or IGF-II) and which may be treated or prevented by modulation of IGFR1 ligand binding, activity or expression. Preferably, the disease or condition is mediated by an increased level of IGFR1, IGF-I or IGF-II and is treated or prevented by decreasing IGFR1 ligand binding, activity (e.g., autophosphorylation activity) or expression. Preferably, the disease or condition is malignant, more preferably a malignancy characterized by a tumor which expresses IGFR1, such as, but not limited to, bladder cancer, Wilm's cancer, bone cancer, prostate cancer, lung cancer, colorectal cancer, breast cancer, cervical cancer, synovial sarcoma, ovarian cancer, pancreatic cancer, benign prostatic hyperplasia (BPH), diarrhea associated with metastatic carcinoid and vasoactive intestinal peptide secreting tumors (e.g., VIPoma or Werner-Morrison syndrome). Acromegaly may also be treated with the antibody molecules of the invention. Antagonism of IGF-I has been reported for treatment of acromegaly (Drake, et al., (2001) Trends Endocrin. Metab. 12: 408-413). Other non-malignant medical conditions which may also be treated, in a subject, by administering an anti-IGFR1 antibody of the invention include gigantism, psoriasis, atherosclerosis, smooth muscle restenosis of blood vessels or inappropriate microvascular proliferation, such as that found as a complication of diabetes, especially of the eye.

The term "subject" may refer to any organism, preferably an animal, more preferably a mammal (e.g., rat, mouse, dog, cat, rabbit) and most preferably a human.

In preferred embodiments, the antibodies and antigen-binding fragments of the invention and pharmaceutical compositions thereof are administered by an invasive route such as by injection (see above). Administration by a non-invasive route (see above) is also within the scope of the present invention.

Compositions can be administered with medical devices known in the art. For example, in a preferred embodiment, a pharmaceutical composition of the invention can be administered by injection with a hypodermic needle.

The pharmaceutical compositions of the invention may also be administered with a needleless hypodermic injection device; such as the devices disclosed in U.S. Pat. Nos. 5,399,163; 5,383,851; 5,312,335; 5,064,413; 4,941,880; 4,790,824 or 4,596,556.

Examples of well-known implants and modules useful in the present invention include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Assays

The anti-IGFR1 antibodies may be used to detect IGFR1 in a biological sample in vitro or in vivo (see, for example, Zola, *Monoclonal Antibodies: A Manual of Techniques*, pp. 147-158 (CRC Press, Inc., 1987)). The anti-IGFR1 antibodies may be used in a conventional immunoassay, including, without limitation, an ELISA, an RIA, FACS, tissue immunohistochemistry, Western blot or immunoprecipitation. The anti-IGFR1 antibodies of the invention may be used to detect IGFR1 from humans. The invention provides a method for detecting IGFR1 in the biological sample comprising contacting the biological sample with an anti-IGFR1 antibody of the invention and detecting the anti-IGFR1 antibody bound to IGFR1, thereby indicating the presence of the IGFR1 in the biological sample. In one embodiment, the anti-IGFR1 antibody is directly labeled with a detectable label and may be detected directly. In another embodiment, the anti-IGFR1 antibody (the first antibody) is unlabeled and a secondary antibody or other molecule that can bind the anti-IGFR1 antibody is labeled. As is well known to one of skill in the art, a secondary antibody is chosen that is able to specifically bind the specific species and class of the first antibody. For example, if the anti-IGFR1 antibody is a human IgG, then the secondary antibody may be an anti-human-IgG. The presence of an anti-IGFR1/IGFR1 complex in the biological sample can be detected by detecting the presence of the labeled secondary antibody. Other molecules that can bind to antibodies (e.g., anti-IGFR1 antibodies) include, without limitation, Protein A and Protein G, both of which are available commercially, e.g., from Pierce Chemical Co. (Rockford, Ill.)

Suitable labels for the anti-IGFR1 antibody or secondary antibody have been disclosed supra, and include various enzymes, prosthetic groups, fluorescent materials, luminescent materials, magnetic agents and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and an example of a magnetic agent includes gadolinium; and examples of suitable radioactive material include $^{125}$I, $^{131}$I, $^{35}$S or $^3$H.

In an alternative embodiment, IGFR1 can be assayed in a biological sample by a competition immunoassay utilizing IGFR1 standards labeled with a detectable substance and an unlabeled anti-IGFR1 antibody. In this assay, the biological sample, the labeled IGFR1 standards and the anti-IGFR1 antibody are combined and the amount of labeled IGFR1 standard bound to the unlabeled antibody is determined. The amount of IGFR1 in the biological sample is inversely proportional to the amount of labeled IGFR1 standard bound to the anti-IGFR1 antibody. One may use the immunoassays disclosed above for a number of purposes. In one embodiment, the anti-IGFR1 antibodies may be used to detect IGFR1 in cells in cell culture. In a preferred embodiment, the anti-IGFR1 antibodies may be used to determine the level of tyrosine phosphorylation, tyrosine autophosphorylation of IGFR1, and/or the amount of IGFR1 on the cell surface after treatment of the cells with various compounds. This method can be used to test compounds that may be used to activate or inhibit IGFR1. In this method, one sample of cells is treated with a test compound for a period of time while another sample is left untreated. If tyrosine autophosphorylation is to be measured, the cells are lysed and tyrosine phosphorylation of the IGFR1 is measured using an immunoassay, for example, as described above. If the total level of IGFR1 is to be measured, the cells are lysed and the total IGFR1 level is measured using one of the immunoassays described above.

A preferred immunoassay for determining IGFR1 tyrosine phosphorylation or for measuring total IGFR1 levels is an ELISA or Western blot. If only the cell surface level of IGFR1 is to be measured, the cells are not lysed, and the cell surface levels of IGFR1 are measured using one of the immunoassays described above. A preferred immunoassay for determining cell surface levels of IGFR1 includes the steps of labeling the cell surface proteins with a detectable label, such as biotin or $^{125}$I, immunoprecipitating the IGFR1 with an anti-IGFR1 antibody and then detecting the labeled IGFR1. Another preferred immunoassay for determining the localization of IGFR1, e.g., cell surface levels, is by using immunohistochemistry. Methods such as ELISA, RIA, Western blot, immunohistochemistry, cell surface labeling of integral membrane proteins and immunoprecipitation are well known in the art. In addition, the immunoassays may be scaled up for high throughput screening in order to test a large number of compounds for either activation or inhibition of IGFR1.

The anti-IGFR1 antibodies of the invention may also be used to determine the levels of IGFR1 in a tissue or in cells derived from the tissue. In a preferred embodiment, the tissue is a diseased tissue. In a more preferred embodiment, the tissue is a tumor or a biopsy thereof. In a preferred embodiment of the method, a tissue or a biopsy thereof is excised from a patient. The tissue or biopsy is then used in an immunoassay to determine, e.g., IGFR1 levels, cell surface levels of IGFR1, levels of tyrosine phosphorylation of IGFR1, or localization of IGFR1 by the methods discussed above. The method can be used to determine if a tumor expresses IGFR1 at a high level.

The above-described diagnostic method can be used to determine whether a tumor expresses high levels of IGFR1, which may be indicative that the tumor will respond well to treatment with anti-IGFR1 antibody. The diagnostic method may also be used to determine whether a tumor is potentially cancerous, if it expresses high levels of IGFR1, or benign, if it expresses low levels of IGFR1. Further, the diagnostic method may also be used to determine whether treatment with anti-IGFR1 antibody is causing a tumor to express lower levels of IGFR1 and/or to exhibit lower levels of tyrosine autophosphorylation, and thus can be used to determine whether the treatment is successful. In general, a method to determine whether an anti-IGFR1 antibody decreases tyrosine phosphorylation comprises the steps of measuring the level of tyrosine phosphorylation in a cell or tissue of interest, incubating the cell or tissue with an anti-IGFR1 antibody or antigen-binding portion thereof, then re-measuring the level of tyrosine phosphorylation in the cell or tissue. The tyrosine phosphorylation of IGFR1 or of another protein(s) may be measured. The diagnostic method may also be used to determine whether a tissue or cell is not expressing high enough levels of IGFR1 or high enough levels of activated IGFR1, which may be the case for individuals with dwarfism, osteoporosis or diabetes. A diagnosis that levels of IGFR1 or active IGFR1 are too low could be used for treatment with activating anti-IGFR1 antibodies, IGF-1, IGF-2 or other therapeutic agents for increasing IGFR1 levels or activity.

The antibodies of the present invention may also be used in vivo to localize tissues and organs that express IGFR1. In a preferred embodiment, the anti-IGFR1 antibodies can be used to localize IGFR1-expressing tumors. The advantage of the anti-IGFR1 antibodies of the present invention is that they will not generate an immune response upon administration. The method comprises the steps of administering an anti-IGFR1 antibody or a pharmaceutical composition thereof to a patient in need of such a diagnostic test and subjecting the patient to imaging analysis to determine the location of the IGFR1-expressing tissues. Imaging analysis is well known in the medical art, and includes, without limitation, x-ray analysis, magnetic resonance imaging (MRI) or computed tomography (CT). In another embodiment of the method, a biopsy is obtained from the patient to determine whether the tissue of interest expresses IGFR1 rather than subjecting the patient to imaging analysis. In a preferred embodiment, the anti-IGFR1 antibodies may be labeled with a detectable agent that can be imaged in a patient. For example, the antibody may be labeled with a contrast agent, such as barium, which can be used for x-ray analysis, or a magnetic contrast agent, such as a gadolinium chelate, which can be used for MRI or CE. Other labeling agents include, without limitation, radioisotopes, such as $^{99}$Tc. In another embodiment, the anti-IGFR1 antibody will be unlabeled and will be imaged by administering a secondary antibody or other molecule that is detectable and that can bind the anti-IGFR1 antibody.

EXAMPLES

The following examples are provided to further describe the present invention and should not be construed to limit the scope of the invention in any way.

Example 1

Construction of Fully Human Anti-IGFR1 Antibodies 1.0. Introduction.

Fully human monoclonal antibodies specific for human insulin-like growth factor receptor 1 (IGFR1) were generated from HuMab mice of the Hco7 genotype (see below), immunized with recombinant sIGFR1 and IGFR1 transfected HEK293 cells. A detailed description of Hco7 mice is provided in U.S. Pat. Nos. 5,545,806; 5,569,825; 5,625,126; 5,633,425; 5,661,016; 5,770,429; 5,789,650; 5,814,318; 5,874,299 and 5,877,397 and in Harding, et al., (1995) Ann. NY Acad. Sci. 764:536-546. Antibodies 1H3, 15H12 and 19D12 were isolated from a HuMab mouse (referred to herein as #23716) which was selected for fusion based on the presence of antigen specific serum IgG titers of 25,600 to the immunizing antigen. The 1H3, 15H12 and 19D121 antibodies were found to bind IGFR1.

2.0 Materials and Methods and Results.

2.1. Antigen.

2.1.1. Mice were immunized with two forms of antigen: (1) live cells (IGFR1 transfected HEK293 cells) and (2) purified protein (sIGFR1; an NSO-expressed recombinant protein encompassing the α-subunit and the extracellular domain of the β-subunit of IGFR1). The biologically active version of this protein is in glycosylated form.

2.1.2. Three immunizations with soluble IGFR1 antigen and final tail vein boosts were performed with a purified IGFR1 preparation at a concentration of 2.67 mg/ml. Soluble IGFR1 was mixed with either complete or incomplete Freund's adjuvant (CFA and IFA) and mice were injected with 0.2 cc (cubic centimeters) prepared antigen into the intraperitoneal cavity. Final tail vein immunizations were performed with soluble IGFR1 in sterile PBS (phosphate buffer saline).

2.1.3. Immunizations were also performed with HEK293 cells transfected with IGFR1 DNA. Specifically, each mouse was immunized, by injection into the intraperitoneal cavity, with 0.2 cc of sterile saline containing $1.0-2.0 \times 10^7$ HEK293 cells expressing IGFR1.

2.2. Transgenic Mice.

2.2.1. Mice were housed in filter cages and were evaluated to be in good physical condition at the time of immunization, at the time of the bleeds and on the day fusions were produced.

2.2.2. The mouse that produced the selected hybridomas was a male (mouse ID #23716) of the (CMD)++; (Hco7) 11952+; (JKD)++; (KCo5) 9272+ genotype. Individual transgene designations are in parentheses, followed by line numbers for randomly integrated transgenes. The symbols ++ and + indicate homozygous or hemizygous; however, because the mice are routinely screened using a PCR-based assay that does not allow us to distinguish between heterozygosity and homozygosity for the randomly integrated human Ig transgenes, a + designation may be given to mice that are actually homozygous for these elements.

2.3. Immunization Procedure and Schedule.

2.3.1. The immunization schedule is shown in the following table.

TABLE 2

Mouse immunization schedule.

| Day | Immunization: adjuvant, antigen | Bleed and Titer[1] |
|---|---|---|
| Day 1 | $1.0 \times 10^7$ live IGFR1 transfected HEK293 cells in saline | |
| Day 15 | CFA adjuvant, sIGFR1 (20 µg) | |
| Day 29 | $1.0 \times 10^7$ live IGFR1 transfected HEK293 cells in saline | |
| Day 37 | | antibody titer measured |
| Day 43 | IFA adjuvant, sIGFR1 (~40 µg) | |
| Day 54 | | antibody titer measured |
| Day 57 | $1.0 \times 10^7$ live IGFR1 transfected HEK293 cells in saline | |
| Day 96 | $1.0 \times 10^7$ live IGFR1 transfected HEK293 cells in saline | |
| Day 103 | | antibody titer measured |
| Day 112 | CFA adjuvant, sIGFR1 (25 µg) | |
| Day 126 | | antibody titer measured |
| Days 128 and 129 | Final tail vein intravenous boosts with sIGFR1[2] | |

[1]Titer information is shown below.
[2]Fusions were performed on day 131.

TABLE 3

Titers of IGFR1 specific antibody during the immunization period of mouse 23716 described in Table 2 (see above).

| Day | Titer |
|---|---|
| 37 | 100 |
| 54 | 800 |
| 103 | 6400 |
| 126 | 25600 |

2.4. Hybridoma Preparation and Testing.

2.4.1. The SP2/0-AG14 myeloma cell line (ATCC CRL 1581) was used for the fusions. The original ATCC vial was thawed and expanded in culture. A seed stock of frozen vials was prepared from this expansion. Cells were maintained in culture for 6-8 weeks and passed twice a week.

2.4.2. High Glucose DMEM containing 10% FBS, Antibiotic-antimycotic (100×), and 0.1% L-glutamine was used to culture myeloma cells. Additional media supplements were added to the hybridoma growth media which included: 5% Origen—Hybridoma Cloning Factor (Fischer Scientific; Suwanee, Ga.), $4.5 \times 10^{-4}$ M sodium Pyruvate, HAT $1.0 \times 10^{-4}$ M Hypoxanthine, $4.0 \times 10^{-7}$ M Aminopterin, $1.6 \times 10^{-5}$ M Thymidine, or HT $1.0 \times 10^{-4}$ M Hypoxanthine, $1.6 \times 10^{-5}$ M Thymidine; and characterized fetal bovine serum.

2.4.3. The spleen from mouse number #23716 was normal in size and yielded $5.73 \times 10^8$ viable cells.

2.4.4. The splenocytes were fused according to the following procedure:

1. Place approximately 10 ml of DMEM+10% FBS into a 50 mL tube.
2. Sacrifice the intravenously boosted mouse.
3. Transfer the mouse into a hood onto a paper towel.
4. Soak the mouse with alcohol, and place onto its right side-left side up.
5. Make a small cut into the skin above the spleen area.
6. Pull skin away from the mouse using both hands.
7. Soak with alcohol again.
8. Use sterile instruments to open the peritoneum.
9. Insert the scissor points under the spleen and open the scissors so as to allow room to grasp the spleen with the forceps.
10. Remove the spleen and place into the tube containing DMEM+10% FBS. Transfer to a sterile tissue culture room.
11. Inside a sterile hood, add approximately 7 mL of DMEM without serum to each of 2 sterile 60 mm culture dishes.
12. Transfer the spleen to the first dish.
13. Remove any adhesions from the spleen using sterile instruments.
14. Place a sterile homogenizer base into a test tube rack (for support).
15. Add the cleaned spleen into the homogenizer.
16. Add approximately 5 mL of DMEM and homogenize 4 passes. Pour off into a sterile 50 mL centrifuge tube.
17. Add another 5-6 mL of DMEM into the homogenizer and make another 3-4 additional passes.
18. Pour off into the same tube as described above.
19. Spin the cells at 1000 rpm for 10 minutes in a centrifuge.
20. Remove the supernatant. Pour off and resuspend pellets in DMEM.
21. Count the spleen cells.
22. Transfer appropriate volume of SP2/0 cells (6 spleen cells per 1 cell of SP2/0) to a 50 mL centrifuge tube. Record volume.
23. Adjust volume of spleen cells with DMEM for more convenient balancing for centrifugation.
24. Spin cells for 10 minutes at 1000 rpm in a centrifuge.
25. Remove supernatants—pour off and resuspend pellets in 30-40 mL of DMEM wash medium (serum free). Combine all cells in one tube.
26. Spin again as above.
27. Pour off supernatant and resuspend pellet.
28. Add approximately 1.2 mL of PEG (polyethylene glycol) at about 1 minute while gently swirling the tube in a beaker containing 37° C. water.
29. Let the tube sit for 90 seconds, then add 15 mL of DMEM wash medium at 3 minutes.
30. Spin the tube as described above.
31. Remove the supernatant and resuspend the pellet gently.
32. Add approximately 10 mL of Hat medium to the tube.
33. Pipette cells into the full volume of HAT medium. Allow the cells to sit for 30-60 minutes in an incubator before plating.
34. Plate cells into 96 well culture plates, 200 µL/well (about $1 \times 10^7$ cells per 96-well plate).
35. Feed cells on day 7 with HT media, 250 µl/well. (HT media, same as HAT media, with Aminopterin removed)

2.4.5. An initial ELISA screen for human IgGκ antibodies was performed 7-10 days post fusion according to the following procedure:
1. Coat plate overnight with anti-hu-κ, 1 µg/mL or anti-hu-γ, 1 µg/mL in 1×PBS, 50 µL/well. Store in refrigerator.
2. Empty plate and block plate in 1×PBST (PBS with Tween)+5% chicken serum for 1 hour at room temperature (100 µL/well).
3. Empty plate and wash manually with wash bottle (3×) or plate washer (3×) using 1×PBST. If wash bottle used, drain plates on paper towels.
4. Standards are used for testing production level of the clones. Make dilutions with unknowns (1:10 in first well and dilute 2 fold across plate). Hu-IgG standards start at 1000 ng/mL and dilute 2 fold across plate. Leave a few wells for blanks: 1×PBST+5% chicken serum which is used for dilutions, 100 µL/well. Incubate at room temperature for 1 hour. Fusion screens and subclones are generally tested diluted 1:2 in blocking buffer. A positive control may also be used when screening fusions and subclones.
5. Repeat wash step #3.
6. Dilute secondary antibody HRP (horse radish peroxidase)-anti-hu IgG-Fc reagent 1:5000 or HRP-anti-hu-κ in 1×PBST+5% chicken serum, add 100 µL/well. Incubate 1 hour at room temperature.
7. Repeat wash step #3. (2×)
8. Develop plate using 10 ml citrate phosphate buffer pH4.0, 80 µL ABTS, 8 µL $H_2O_2$ per plate.
9. Incubate 30 minutes to 1 hour at room temperature. Read plate at $OD_{415\ nm-490\ nm}$.

Solutions:

1×PBST=1×PBS+0.05% tween-20

Citrate phosphate buffer=21 gm/L citric acid, 14.2 gm/L disodium hydrogen phosphate (anhydrous); pH4.0

ABTS=27.8 mg/mL 2,2'-azino-bis(3-ethylbenzthiazoline-6-sulfonic acid) diammonium salt in citrate buffer, freeze 1 mL aliquots.

Plate=96 well assay plate.

A positive ELISA signal was detected in the wells corresponding to hybridomas 1H3, 15H12 and 19D12, demonstrating that these hybridomas produced human IgG antibodies.

2.4.6. Hybridoma supernatants corresponding to human IgGκ positive wells were then screened on soluble IGFR1 coated ELISA plates according to the following procedure:
1. Coat plate overnight with IGFR1 (1.0 µg/mL) in 1×PBS, 50 µL/well. Store in refrigerator. Five milliliters needed for coating plate.
2. Empty plate and block plate in 1×PBST+5% chicken serum for 1 hour at room temperature (100 µL/well).
3. Empty plate and wash manually with wash bottle (3×) or plate washer (3×) using 1×PBST. If wash bottle used, drain plates on paper towels.
4. Use blocking buffer as diluent. Test sera, beginning at 1:50 dilution in the top row of the plate and dilute 2 fold/row down the plate (7×). Incubate at room temperature 1 hour. For subclone screening, a 1:1 dilution of culture supernatant in blocking buffer is used as starting material.

5. Repeat wash step #3.
6. Dilute secondary HRP-anti-hu IgG-Fc specific and/or HRP-anti-hu-κ reagent 1:2500-5000 in 1×PBST +5% chicken serum, add 100 µL/well. Incubate 1 hour at room temperature.
7. Repeat wash step #3. (2×)
8. Develop plate using 10 mL citrate-phosphate buffer pH4.0, 80 µL ABTS, 8 µL $H_2O_2$ per plate.
9. Incubate 30 minutes to 1 hour at room temperature. Read plate at $OD_{415\,nm\text{-}490\,nm}$. Consider twice above background titer limit.

In these assays, hybridomas 15H12 and 19D12 produced a positive ELISA signal. These data demonstrate that the hybridomas produced antibodies which can bind to soluble IGFR1.

Antigen positive hybridomas were then transferred to 24 well plates, and eventually to tissue culture flasks. IGFR1 specific hybridomas were subcloned by limiting dilution to assure monoclonality. Antigen positive hybridomas were preserved at several stages in the development process by freezing cells in Origen DMSO freeze medium (Fischer Scientific; Suwanee, Ga.).

2.4.7. Antibody isotypes were determined according to the following procedure:
1. Coat plate overnight in refrigerator at I µg/ml soluble IGFR1 in 1> PBS, 50 µL/well. Empty plate.
2. Add 1×PBST+5% chicken serum for 1 hour at room temperature. (100 µL/well). Empty plate.
3. Use blocking buffer as a diluent, add supernatant or purified material to be tested in 1 well per secondary antibody to be tested-50 µL/well. Incubate for 90 minutes at room temperature. Empty plate.
4. Empty plate and wash manually with wash bottle (3×) or plate washer (3×) using 1×PBST. If wash bottle used, drain plates on paper towels.
5. Using blocking buffer as a diluent, add secondary antibodies:
HRP-anti-hu-gamma;
HRP-anti-hu kappa;
HRP-anti-human IgGI; or
HRP-anti-human IgG3
diluted 1:1000. Incubate for 45 minutes at room temperature. Empty plate.
6. Repeat wash step #4 (3×).
7. Develop plate using 10 mL citrate-phosphate buffer pH4.0, 80 µL ABTS, 8 µL $H_2O_2$ per plate.
8. Incubate 30 minutes to 1 hour at room temperature. Read plate at $OD_{415\,nm\text{-}490\,nm}$.

The data from these assays is shown, below, in Table 4.

TABLE 4

Isotype ELISA results*.

| | γ 1 | κ 2 | γ1 3 | γ3 4 | 5 | 6 | 7 |
|---|---|---|---|---|---|---|---|
| clone I15H12 | 1.903 | 1.003 | 0.064 | 0.813 | | | |

*Each number represents the magnitude of the ELISA signal observed for each secondary antibody.

These data demonstrate that antibody 15H12 is an IgG3κ antibody.

2.4.8. Hybridoma supernatants (1H3, 15H12 and 19D12) and MAB391 were also tested, in a fixed cell ELISA assay, for the ability to directly bind cells expressing IGFR1. In the assay, MCF-7 cells or HEK293 cells transfected with IGFR1 DNA were used. The assays were performed as follows:
1. Add 50 µg/well of a 20 µg/mL solution of Poly-L-lysine in 1×PBS to each well of a 96 well plate and incubate for 30 minutes at room temperature or overnight at 4° C. Empty plate to remove Poly-L-lysine from the wells and allow to dry at room temperature until use.
2. Wash live cells three times with 1×PBS by centrifugation (1000 RPM/5 minutes). Adjust final cell concentration to $2 \times 10^6$ cells per well in 1×PBS. Add 50 µL per well of this cell suspension.
3. Spin cells 5 minutes at 2000 RPM. Empty buffer.
4. Add 50 µL/well of 0.5% ice cold glutaraldehyde in 1×PBS. Let sit for 15 minutes at room temperature. Empty plate.
5. Add 1×PBST+5% chicken serum and incubate for 1 hour at room temperature (100 µL/well). Empty plate.
6. Wash plate gently using 1×PBST (2×). To avoid cell loss, this step should be done manually in a container avoiding any plate washers.
7. Using blocking buffer as a diluent, test culture supernatant by adding 100 µg of a 1:1 dilution. Incubate 1 hour at room temperature.
8. Repeat step 6 (3×).
9. Dilute secondary HRP anti-hu IgG-Fc specific and/or HRP anti-hu-κ, reagent 1:2500-5000 in 1×PBST+5% chicken serum, add 100 µL/well. Incubate 1 hour at room temperature.
10. Repeat step 6 (3×).
11. Develop plate using 10 ml citrate-phosphate buffer pH4.0, 80 µL, ABTS, 8 µL $H_2O_2$ per plate.
12. Incubate 15-20 minutes at room temperature. Read plate at $OD_{415\,nm\text{-}490\,nm}$.

The results from these assays demonstrated that hybridomas 1H3, 15H12 and 19D12 produced an immunoglobulin which binds to HEK293 cells expressing IGFR1 and that hybridomas 1H3, 15H12 and 19D12 produced an immunoglobulin which binds to MCF-7 cells which express endogenous IGFR1. Additionally, the results demonstrated that MAB391 bound to IGFR1 expressing HEK293 cells and to MCF-7 cells.

2.4.9. The ability of hybridoma supernatants (1H3, 15H12 and 19D12) to block binding of IGF1 to IGFR1 was evaluated by measuring 1) staining intensity of the supernatant on IGFR1 expressing HEK293 cells and on MCF7 cells and 2) the ability of the supernatants to block binding of IGF1-biotin to IGFR1 expressing cells. Initially, biotinylated IGF1 was titrated on IGFR1 expressing HEK293 cells in order to establish the proper concentration to evaluate blocking of IGF1 binding to its receptor by the antibodies of the present invention. This was done by the following procedure:
1. IGFR1 expressing HEK293 cells are harvested from a flask by slapping the flask to loosen the cells which were pipeted in to a conical tube. The cells are then centrifuged at 300×g for 5 minutes to pellet the cells. The medium is then aspirated.
2. The cells are washed in 10-20 mL PBS containing 0.02% sodium azide and resuspended in the same buffer at approximately $2.5 \times 10^6$ cells/mL ($\pm 10^6$ cells). The cells are aliquoted, 200 µL/well into a 96 well microtiter plate in the same buffer at 4° C. The cells are pelleted and the supernatant is aspirated.
3. The cells are stained by adding 50 µL/well serially diluted IGF1-biotin in the same buffer, starting at a 1:5 dilution followed by 4-fold serial dilutions. The plate is tapped or gently vortexed to ensure an even suspension of cells are suspended. The cells are then incubated for 30 minutes at 4° C.
4. The cells are washed 3× by adding 150 µL buffer for the first wash and then pelleted. The supernatant is aspirated and 200 µL buffer is added. Again, the cells are pelleted and the supernatant is aspirated; this wash step is repeated once more. Streptavidin-PE (streptavidin-R-Phycoerythrin) is added and the cells are incubated for 30 minutes at 4° C.
5. The cells are washed once in PBS containing 2% FBS and 0.02% azide and resuspended in the same buffer except containing also 50 µg/mL propidium iodide to exclude dead cells.
6. The cells are analyzed by FACS.

The blocking assays were performed as follows:
1. Harvest MCF7 cells or HEK293/IGFR1 cells from a tissue culture flask by slapping the flask sides to loosen the cells. Pipet the cells into a conical tube. Centrifuge the tube for 5 minutes at 300×g to pellet the cells. Aspirate the medium.
2. Wash the cells in 10-20 mL PBS containing 2% FBS and 0.02% sodium azide (PFA), and resuspend in the same buffer at approximately $2.5 \times 10^6$ ($\pm 1 \times 10^6$). Aliquot 200 µL/well into a 96 well microtiter plate in the same buffer at 4° C. Pellet the cells and aspirate the buffer.
3. Stain the cells with each IGFR1 hybridoma supernatant by adding 100 µL/well, including a medium (negative) control, and MAB391 as a positive control. Tap the plate to ensure even suspension of the cells. Incubate 30-60 minutes at 4° C.
4. Wash the cells 3 times in PFA by adding 100 µL buffer for the first wash, pellet, aspirate, resuspend in 200 µL buffer, pellet, aspirate, resuspend again in 200 µL buffer, divide each sample into two wells and pellet.
5. To one set of wells, add anti-human IgG-FITC diluted 1:100 in PFA (para-formaldehyde) to the supernatant stained samples and the medium control, and anti-mouse IgG-FITC at 1:200 to the MAB391 stained samples, again ensuring even dispersal of the cells (staining assay). Incubate for 30 minutes at 4° C.
6. To the second set of wells, add IGF1-biotin diluted 1:500 in PBS containing 0.02% azide (no FBS) and incubate for 30 minutes at 4° C. Wash the cells 3 times as described in step 4 (but without dividing the sample). Stain these cells by adding streptavidin-PE (streptavidin-R-Phycoerythrin) in PFA (blocking assay). Incubate for 30 minutes at 4° C.
7. Wash all the samples once in PFA, and resuspend in the same buffer except containing also 50 µg/mL propidium iodide to exclude dead cells.
8. Analyze by FACS analysis.

The results from these blocking assays demonstrated that the supernatants from hybridomas 1H3, 15H12 and 19D12 block binding of biotinylated IGF1 to IGFR1, stain MCF7 cells which express endogenous IGFR1 and stain HEK293 cells expressing IGFR1.

2.4.10. The ability of purified antibodies 1H3 and 15H12 to block binding of biotinylated IGF1 to IGFR1 in an ELISA assay and of antibodies 1H3, 15H12 and 19D12 to block binding of biotinylated MAB391 to IGFR1 in an ELISA assay was also evaluated according to the following procedure:
1. Coat plate overnight in a refrigerator with 1 µg/mL soluble IGFR1 in 1×PBS-50 µL/well.
2. Add 1×PBST+5% chicken serum for 1 hour at room temperature-100 µL/well. Empty plate.
3. Wash plate 3× with wash buffer (1×PBS+0.05% tween-20). Slap plate dry.
4. 2 µg/mL 1H3, 15H12 or 19D12 or positive or negative control antibodies are diluted in blocking buffer across the plate. The plates are incubated at room temperature for 1 hour.
5. Wash plates 3× in wash buffer.
6. Biotin-IGF1 or Biotin-MAB391 is added-50 µL/well-and incubated for 30 minutes at room temperature.
7. Wash plate 3×
8. Add 100 µL/well of streptavidin labeled alkaline phosphatase or horse radish peroxidase, incubate for 30 minutes at room temperature.
9. Wash plate 3×. Develop with appropriate reagent depending on the label used.
10. Read after 10-15 minutes.

MAB391 was biotinylated according to the following procedure:
1. Prepare MAB391 in PBS buffer (dialyze or use desalting column to remove unwanted buffers such as Tris or glycine).
2. Prepare a fresh stock solution of Sulfo-NHS-LC-biotin solution just before use. Add 2.0 mg of Sulfo-NHS-LC-biotin to 200 µL distilled water. Add this reagent to MAB391 at a 12-fold molar excess if working with a 10 mg/mL solution of MAB391, or a 20-fold molar excess when working with a dilute preparation of MAB391 (2 mg/mL).
3. Calculation: mmoles MAB391=mg protein/150,000 mmoles×12 or 20=mmoles biotin reagent to add mmoles biotin to add×556=mg biotin reagent to add
For 1 mg/mL:

$1/150000 = 6.6 \times 10^6$ $20 \times 6.6 \times 10^{-6}$ mmoles $= 1/32 \times 10^{-4}$ NHS-LC-biotin $1.32 \times 10^{-4} \times 556 = 0.073$ mg sulfo NHS-LC-biotin From the stock NHS-LC-biotin solution, use 10 µL (100 µg) of solution per mg IgG for 1 or 2 mg.
4. Incubate for 2 hours on ice or for 30 minutes at room temperature. Dialyze against PBS or use desalting column to remove unreacted biotin reagent. Store at 4° C. in PBS 0.1% sodium azide.

In general, 3-5 biotins should be added to each IgG molecule labeled.

The results from these blocking assays demonstrated that antibodies 1H3 and 15H12 blocks binding of biotinylated IGF1 to sIGFR1 and that antibodies 1H3, 15H12 and 19D12 block biotinylated MAB391 binding to sIGFR1.

2.4.11. Binding between IGFR1 and the 1H3, 15H12 and 19D12 antibodies was evaluated in a BIAcore/surface plasmon resonance assay according to the following procedure:
1. IGFR1 is immobilized on a CM-5 chip by amine coupling, to a level of 350.4 response units on flow cells. The concentration of IGFR1 which is used to immobilize is 2.5 µg/mL in sodium acetate buffer and the protein is immobilized at pH 3.5.
2. Antibodies 1H3, 15H12 and 19D12 are purified from hybridoma supernatants over a Protein-A or Protein-G column and tested for purity by SDS-PAGE analysis (4%-12% Tris-Glycine).
3. The antibodies are made to flow over the IGFR1 surface prepared above.

4. The concentration range of antibodies used is 4, 2, 1, 0.5 and 0.25 µg/mL. A blank is also used for background substitution. Samples are prepared in HBS buffer.
5. Injection time (association phase) is 10 minutes, at a flow rate of 20 µL/minute, dissociation time (dissociation phase) is 1 hour at the same flow rate.
6. The assays are run at both 25° C. and 37° C. All experiments are done in duplicate.
7. Data analysis is carried out using Bia-Evaluation software v.3.0.2 (Biacore, Inc; Piscataway, N.J.).
8. All experiments are carried out using a Biacore 3000 surface plasmon resonance instrument (Biacore, Inc; Piscataway, N.J.).

The results for these assays demonstrated that antibodies 15H12 and 19D12 associate with IGFR1 at 25° C. and at 37° C. and that antibody 1H3 associates with IGFR1 at 25° C. The data from these experiments were also used to calculate the affinity and rate constants of 1H3, 15H12 and 19D12 binding to IGFR1 (see Table 5, below).

Example 3

IGFR1 Autophosphorylation Assay

The ability of 1H3, 15H12 and 19D12 to inhibit IGFR1 autophosphorylation was also determined.

Antibodies (1H3, 15H12 or 19D12) were added to cells bearing IGFR1 for various lengths of times. Cells were then stimulated with 10 ng/ml IGF-I for 5 min at 37° C. Cells were washed twice with cold PBS containing 0.1 mM sodium vanadate and lysed in lysis buffer (50 mM HEPES, pH7.4, 150 mM NaCl, 10% glycerol, 1% Triton X-100, 1.5 mM $MgCl_2$, protease inhibitors and 2 mM sodium vanadate). Lysates were incubated on ice for 30 min and then centrifuged at 13,000 RPM for 10 min at 4° C. Protein concentrations of the lysates were measured by a Coomassie colorimetric assay, and subjected to immunoprecipitation and Western blot analysis.

TABLE 5

Affinity and rate constants of antibodies 1H3, 15H12 and 19D12 with IGFR1.

| Temp. | Antibody | Sample size | Assoc. time (min.) | Dissoc. time (min.) | $k_{on}$ (1/Ms) | $k_{off}$ (1/s) | $K_D$ (M) | Half-life (min.)[#] |
|---|---|---|---|---|---|---|---|---|
| 25° C. | 15H12 | 2 | 10 | 60 | $5.0 \times 10^5$ | $2.24 \times 10^{-5}$ | $4.48 \times 10^{-11}$ | 515.73 |
| 25° C. | 19D12 | 2 | 10 | 60 | $4.0 \times 10^5$ | $2.65 \times 10^{-5}$ | $5.92 \times 10^{-11}$ | 435.94 |
| 25° C. | 1H3   | 2 | 10 | 60 | $0.7 \times 10^5$ | $6.50 \times 10^{-5}$ | $86 \times 10^{-11}$ | 177.73 |
| 37° C. | 15H12 | 2 | 10 | 60 | $7.2 \times 10^5$ | $4.01 \times 10^{-5}$ | $5.57 \times 10^{-11}$ | 288.09 |
| 37° C. | 19D12 | 2 | 10 | 60 | $6.8 \times 10^5$ | $4.93 \times 10^{-5}$ | $7.22 \times 10^{-11}$ | 234.33 |

[#]Calculated as Half life = $\ln(2/k_{off})$

Example 2

Cell Based Receptor Binding Assay

A cell based receptor binding assay was used to determine if antibodies 1H3, 15H12 and 19D12 competed with IGF1 for binding to IGFR1.

In the assays, 96 well filter plates (1.2 µm pore) were pre-wet with 0.5% bovine serum albumin (BSA)/PBS for 2 hours at 4° C. The buffer was then removed with a vacuum manifold. Various concentrations of 6× control or test antibody (1H3, 15H12 or 19D12) were added to the wells (25 µL). The [$^{125}$I]-IGF-1 ligand was then added to the wells at a final concentration of 0.375 nM in BSA/PBS. Cells were harvested with cell dissociation solution, counted with trypan blue, and resuspended in 0.5% BSA/PBS to a cell number of $1-3\times10^5$/ml. One hundred µl of cells (10,000-30,000) were added to each well. The plate was shaken at 4° C. for 1 hour. The plate was then aspirated and washed three times with ice cold PBS using a vacuum manifold. The filters were punched out and counted on a gamma counter. Data were analyzed for competitive binding.

The results of these experiments indicated that 1H3, 15H12 and 19D12 were capable of competing with IGF-I for binding to IGFR1.

The results of these assays indicated that antibodies 1H3, 15H12 and 19D12 inhibited IGFR1 autophosphorylation with an $IC_{50}$ of 0.10 nM.

Example 4

Anchorage-Independent Growth (Soft Agar) Assay

The ability of an anti-IGFR1 antibodies 1H3, 15H12, 19D12 and MAB391 to inhibit anchorage-independent growth of various cells, including human breast cancer cell line MCF7, human colorectal cancer cell HT29 and human prostatic cancer cell DU145, was evaluated.

In these experiments, three milliliters of 0.6% agarose in complete MEM medium were added to each well of 6 well tissue culture plates and allowed to solidify (bottom layer). One hundred microliters of antibody 1H3, 15H12, 19D12 or MAB391 (discussed above), at various concentrations, was added to culture tubes. Cells were harvested. Aliquots of the cells (15,000 cells) were added to the culture tubes containing the antibody and incubated at room temperature for 10-15 minutes. Three milliliters of a 0.35% agarose/complete minimal essential media (MEM) layer (top layer) were added to the antibody/cell mixture and then plated onto the solidified bottom layer. The top layer was allowed to solidify. The plates were then incubated for three weeks. MTT (3-(4,5-Dimethyl-2-Thiazolyl)-2,5-Diphenyl-2H-Tetrazolium Bromide) was added to the wells and incubated for 1-2 hours. The plates were scanned and the colonies counted and analyzed using a customized colony counter application program.

The results of these experiments demonstrated that an anti-IGFR1 antibody can inhibit anchorage-independent growth of all three malignant cell lines tested.

Example 5

Cloning of the Variable Regions of an Antibody from Hybridomas

Nucleic acids encoding the 1H3, 15H12 and 19D12 variable regions were obtained from hybridomas according to the following procedure.

Messenger RNA (mRNA) from $2\times10^6$ hybridoma cells was prepared by using a Micro-Fast Track kit (Invitrogen; Carlsbad, Calif.). Cellular DNA (cDNA) encoding the variable region was prepared according the procedure described in "cDNA Cycle" kit (Invitrogen; Carlsbad, Calif.).

The antibody variable regions were PCR amplified using the cDNA as a template using 5'RACE (Clotech; Palo Alto, Calif.) technology. The following 3' primer sequence was used to amplify the heavy chain: 5'-TGCCAGGGGGMGAC-CGATGG-3' (SEQ ID NO: 22) and following 3' primer sequence was used to amplify the light chain: 5'-CGGGM-GATGAAGACAGATG-3' (SEQ ID NO:23). Additionally, 5'-RACE PCR primers (Clotech; Palo Alto, Calif.) were used in each amplification.

The PCR reaction mixture included 2.5 units of Pfu I polymerase in its appropriate buffer (Stratagene; La Joola, Calif.), 0.2 mM of each dNTP, 750 nM of each 5' and 3' primer and cDNA template. Total reaction volume was 50 µl. The following PCR cycling program was performed using a thermocycler:

| | |
|---|---|
| 1X | 94° C., 2 min. |
| 10X | 94° C., 45 sec. |
| | 65° C., 45 sec. Minus 1° C. per cycle |
| | 72° C., 1 min. |
| 25X | 94° C., 45 sec. |
| | 55° C., 45 sec. |
| | 72° C., 1 min. |
| 1X | 72° C., 15 min. |

The resulting PCR amplification product was inserted into the Zero Blunt TOPO PCR cloning vector (Invitrogen; Carlsbad, Calif.). The identity of the insert was verified by restriction enzyme analysis and then the nucleotide sequence of the insert was obtained by sequencing.

Example 6

Recombinant Expression of Antibody Chains

In this example, nucleic acids encoding various anti-IGFR1 antibody chains of the present invention were used to transfect a dhfr⁻ mammalian cell line (CHO-DXB11) wherein the chains were expressed. Transient transfections were carried out by cotransfection of the cell line with various combinations of one heavy (γ1 or γ4) and one light (κ) chain plasmid, selected from plasmids 1-11, listed below. Construction of stable cell lines was performed by transfection by a single plasmid, either 12 or 13, listed below, as follows: The nucleic acids were located in a single plasmid and were operably linked to cytomegalovirus (CMV) promoters. The plasmids also contained DHFR cDNA operably linked to a mouse mammary tumor virus long terminal repeat (MMTV-LTR) which was used for plasmid amplification. The plasmid further included the hygromycin B gene operably linked to the TK promoter for selection in mammalian cells.

Below is a description of the promoter-expression cassette in the 13 plasmids which were constructed. The indicated plasmids (24 and 8-11) were deposited, under the Budapest Treaty, on May 21, 2003 with the American Type Culture Collection (ATCC); 10801 University Boulevard; Manassas, Va. 20110-2209 under the indicated name and accession number:

(1) CMV promoter-15H12/19D12 HC (γ4)
   Insert Sequence: SEQ ID NO: 3;
(2) CMV promoter-15H12/19D12 HCA (γ4)—
   Deposit name: "15H12/19D12 HCA (γ4)"
   ATCC accession No.: PTA-5214
   Insert Sequence: SEQ ID NO: 44;
(3) CMV promoter-15H12/19D12 HCB (γ4)—
   Deposit name: "15H12/19D12 HCB (γ4)"
   ATCC accession No.: PTA-5215
   Insert Sequence: SEQ ID NO: 111;
(4) CMV promoter-15H12/19D12 HCA (γ1)—
   Deposit name: "15H12/19D12 HCA (γ1)";
   ATCC accession No.: PTA-5216
   Insert Sequence: SEQ ID NO: 44;
(5) CMV promoter-15H12/19D12 LC (κ)
   Insert Sequence: SEQ ID NO: 1;
(6) CMV promoter-15H12/19D12 LCA (κ)
   Insert Sequence: SEQ ID NO: 40;
(7) CMV promoter-15H12/19D12 LCB (κ)
   Insert Sequence: SEQ ID NO: 42;
(8) CMV promoter-15H12/19D12 LCC (κ)—
   Deposit name: "15H12/19D12 LCC (κ)";
   ATCC accession No.: PTA-5217
   Insert Sequence: SEQ ID NO: 71;
(9) CMV promoter-15H12/19D12 LCD (κ)—
   Deposit name: "15H12/19D12 LCD (κ)";
   ATCC accession No.: PTA-5218
   Insert Sequence: SEQ ID NO: 73;
(10) CMV promoter-15H12/19D12 LCE (κ)—
   Deposit name: "15H12/19D12 LCE (κ)";
   ATCC accession No.: PTA-5219
   Insert Sequence: SEQ ID NO: 75;
(11) CMV promoter-15H12/19D12 LCF (κ)—
   Deposit name: "15H12/19D12 LCF (κ)";
   ATCC accession No.: PTA-5220
   Insert Sequence: SEQ ID NO: 77;
(12) CMV promoter-15H12/19D12 HC (γ4) and CMV promoter-15H12/19D12 LC (κ);
(13) CMV promoter-15H12/19D12 HCA (γ1) and CMV promoter-15H12/19D12 LC (κ)

All restrictions on access to the plasmids deposited at the ATCC have been irrevocably removed.

The 3' end of each cassette was linked to a beta-globin poly A signal. The variable chains which were expressed were linked to the constant region indicated in parentheses (i.e., γ1, γ4 or κ). Analysis of the transfected cell lines containing each plasmid indicated that the corresponding antibody chain polypeptides were expressed (amino acid sequences of the expression products not confirmed).

Each of the above-referenced plasmids constitutes part of the present invention. Further, the nucleic acid located within each expression cassette, along with the immunoglobulin variable region therein, along with the mature, processed version thereof (i.e., lacking the signal sequence), particularly, SEQ ID NO: 44, mature HCA (nucleotides 58-411 of SEQ ID NO: 44), SEQ ID NO: 111, mature HCB (nucleotides 58-411 of SEQ ID NO: 111), SEQ ID NO: 71, mature LCC (nucleotides 58-384 of SEQ ID NO: 71), SEQ ID NO: 73, mature LCD (nucleotides 58-384 of SEQ ID NO: 73), SEQ ID NO: 75, mature LCE (nucleotides 58-384 of SEQ ID NO: 75), SEQ ID NO: 77 or mature LCF (nucleotides 58-384 of SEQ ID NO: 77), optionally including an immunoglobulin constant region, along with any polypeptide encoded by any of the foregoing nucleic acids, including mature or unprocessed chains, optionally including an immunoglobulin constant region, is a part of the present invention. Moreover, any antibody or antigen-binding fragment thereof comprising one of the encoded polypeptides is part of the present invention.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, Genbank Accession Numbers and publications are cited throughout this application, the disclosures of which are incorporated herein by reference in their entireties.

We claim:

1. An isolated nucleic acid encoding a polypeptide comprising an amino acid sequence selected from the group consisting of:
   (a) amino acids 20-128 of SEQ ID NO: 2;
   (b) amino acids 21-130 of SEQ ID NO: 25;
   (c) amino acids 20-128 of SEQ ID NO: 72;
   (d) amino acids 20-128 of SEQ ID NO: 74;
   (e) amino acids 20-137 of SEQ ID NO: 4;
   (f) amino acids 20-140 of SEQ ID NO: 27;
   (g) amino acids 20-137 of SEQ ID NO: 45;
   (h) amino acids 20-137 of SEQ ID NO: 112;
   (i) amino acids 20-128 of SEQ ID NO: 76; and
   (j) amino acids 20-128 of SEQ ID NO: 78.

2. A nucleic acid of claim 1 comprising a nucleotide sequence selected from the group consisting of:
   (a) nucleotides 58-384 of SEQ ID NO: 1;
   (b) nucleotides 61-390 of SEQ ID NO: 24;
   (c) nucleotides 58-384 of SEQ ID NO: 71;
   (d) nucleotides 58-384 of SEQ ID NO: 73;
   (e) nucleotides 58-411 of SEQ ID NO: 3;
   (f) nucleotides 58-420 of SEQ ID NO: 26;
   (g) nucleotides 58-411 of SEQ ID NO: 44;
   (h) nucleotides 58-411 of SEQ ID NO: 111;
   (i) nucleotides 58-384 of SEQ ID NO: 75; and
   (j) nucleotides 58-384 of SEQ ID NO: 77.

3. An isolated recombinant vector comprising a nucleic acid of claim 1.

4. An isolated host cell comprising a vector of claim 3.

5. An isolated nucleic acid encoding an immunoglobulin polypeptide chain comprising CDR-LI, CDR-L2 and CDR-L3 found in a light chain variable region that comprises the amino acid sequence set forth in SEQ ID NO: 78.

6. The nucleic acid of claim 5 encoding a polypeptide comprising amino acids 20-128 of SEQ ID NO: 78.

7. The nucleic acid of claim 6 wherein the carboxy-terminus of the polypeptide is fused to an immunoglobulin kappa constant chain.

8. The nucleic acid of claim 6 encoding a polypeptide comprising amino acids 1-128 of SEQ ID NO: 78.

9. The nucleic acid of claim 6 comprising nucleotides 58-384 of SEQ ID NO: 77.

10. The nucleic acid of claim 9 comprising nucleotides 1-384 of SEQ ID NO: 77.

11. An isolated nucleic acid encoding an immunoglobulin polypeptide chain comprising CDR-HI, CDR-H2 and CDR-H3 found in a heavy chain variable region that comprises the amino acid sequence set forth in SEQ ID NO: 45.

12. The nucleic acid of claim 1 encoding a polypeptide comprising amino acids 20-137 of SEQ ID NO: 45.

13. The nucleic acid of claim 12 wherein the carboxy-terminus of the polypeptide is fused to an immunoglobulin gamma-1 constant chain.

14. The nucleic acid of claim 12 encoding a polypeptide comprising amino acids 1-137 of SEQ ID NO: 45.

15. The nucleic acid of claim 12 comprising nucleotides 58-411 of SEQ ID NO: 44.

16. The nucleic acid of claim 15 comprising nucleotides 1-411 of SEQ ID NO: 44.

17. The isolated nucleic acid of claim 5 encoding an immunoglobulin polypeptide chain comprising CDR-LI, CDR-L2 and CDR-L3 found in a light chain variable region that comprises the amino acid sequence set forth in SEQ ID NO: 78; and encoding an immunoglobulin polypeptide chain comprising CDR-HI, CDR-H2 and CDR-H3 found in a heavy chain variable region that comprises the amino acid sequence set forth in SEQ ID NO: 45.

18. The nucleic acid of claim 17 wherein the carboxy-terminus of the light chain variable region is fused to an immunoglobulin kappa constant chain; and wherein the carboxy-terminus of the heavy chain variable region is fused to an immunoglobulin gamma-1 constant chain.

19. The nucleic acid of claim 17 comprising an isolated nucleic acid encoding an immunoglobulin polypeptide chain comprising CDR-L1, CDR-L2 and CDR-L3 found in a light chain variable region that comprises the amino acid sequence set forth in SEQ ID NO: 78 or a mature fragment thereof which is operably linked to a promoter; and encoding an immunoglobulin polypeptide chain comprising CDR-H1, CDR-H2 and CDR-H3 found in a heavy chain variable region that comprises the amino acid sequence set forth in SEQ ID NO: 45 or a mature fragment thereof which is operably linked to a promoter.

20. The nucleic acid of claim 19 wherein each of the promoters are CMV promoters.

21. The nucleic acid of claim 20 wherein the carboxy-terminus of the light chain variable region is fused to an immunoglobulin kappa constant chain and operably linked to a CMV promoter; and wherein the carboxy-terminus of the heavy chain variable region is fused to an immunoglobulin gamma-1 constant chain and operably linked to a CMV promoter.

22. An isolated vector comprising the nucleic acid of claim 17.

23. An isolated host cell comprising the vector of claim 22.

24. The host cell of claim 23 which is a Chinese hamster ovary cell.

25. The host cell of claim 24 wherein the vector comprises a DHFR gene operably linked to a mouse mammary tumor virus long terminal repeat promoter; and a hygromycin B gene operably linked to a TK promoter.

26. An isolated plasmid deposited at the American Type Culture Collection under deposit number PTA 5214, PTA-5215, PTA-5216, PTA-5217, PTA-5218, PTA-5219 or PTA-5220.

27. An isolated plasmid of claim 26 deposited at the American Type Culture Collection under deposit number PTA-5216.

28. An isolated plasmid of claim 26 deposited at the American Type Culture Collection under deposit number PTA-5220.

29. An isolated host cell comprising a plasmid of claim 26.

30. A method for producing an immunoglobulin polypeptide chain comprising CDR-LI, CDR-L2 and CDR-L3 found in a light chain variable region that comprises the amino acid sequence set forth in SEQ ID NO: 78; and an immunoglobulin polypeptide chain comprising CDR-HI, CDR-H2 and CDR-H3 found in a heavy chain variable region that comprises the amino acid sequence set forth in SEQ ID NO: 45; comprising culturing a host cell comprising a vector comprising one or more nucleic acids encoding said polypeptides under conditions in which the polypeptides are produced.

31. The method of claim 30 wherein the nucleic acids are each operably associated with promoters.

32. The method of claim 30 further comprising purifying the polypeptides and combining the polypeptides with a pharmaceutically acceptable carrier comprising water, buffer and sugar.

33. The method of claim 32 further comprising administering the polypeptides to a human subject.

34. A method for producing a polypeptide comprising culturing the host cell of claim 4 under conditions in which the polypeptide is produced.

35. The method of claim 34 wherein the nucleic acids encoding the polypeptides are operably associated with promoters.

36. The method of claim 34 further comprising purifying the polypeptides and combining the polypeptides with a pharmaceutically acceptable carrier comprising water, buffer and sugar.

37. A method for producing a polypeptide comprising culturing a host cell comprising the nucleic acid of claim 6 under conditions in which the polypeptide is produced.

38. A method for producing a polypeptide comprising culturing a host cell comprising the nucleic acid of claim 12 under conditions in which the polypeptide is produced.

39. A method for making an antibody comprising culturing a host cell comprising an isolated nucleic acid encoding an immunoglobulin polypeptide light chain comprising the amino acid sequence set forth in SEQ ID NO: 78; and encoding an immunoglobulin polypeptide heavy chain comprising the amino acid sequence set forth in SEQ ID NO: 45, in a culture medium under conditions in which the polypeptides are produced and processed to mature immunoglobulin polypeptides, and associate to form an antibody, and are secreted from the host cell into the culture medium.

40. The method of claim 39 wherein:
(a) the nucleic acid is in a vector;
(b) the host cell is a Chinese hamster ovary cell; and
(c) the immunoglobulin chains are encoded by nucleic acids each operably linked to a CMV promoter.

41. The method of claim 40 further comprising purifying the antibody from the culture medium and combining the antibody with a pharmaceutically acceptable carrier comprising water, buffer and sugar.

42. The method of claim 40 wherein the nucleic acid encoding the heavy chain immunoglobulin is in a plasmid deposited at the American Type Culture Collection under deposit number PTA-5216; and wherein the nucleic acid encoding the light chain immunoglobulin is in a plasmid deposited at the American Type Culture Collection under deposit number PTA-5220.

43. The nucleic acid of claim 1 wherein the polypeptide carboxy-terminus is linked to an immunoglobulin constant region.

44. The nucleic acid of claim 43 encoding a polypeptide comprising an amino acid sequence selected from the group consisting of:
(a) amino acids 20-128 of SEQ ID NO: 2 wherein the carboxy-terminus is fused to an immunoglobulin kappa constant region polypeptide;
(b) amino acids 21-130 of SEQ ID NO: 25 wherein the carboxy-terminus is fused to an immunoglobulin kappa constant region polypeptide;
(c) amino acids 20-128 of SEQ ID NO: 72 wherein the carboxy terminus is fused to an immunoglobulin kappa constant region polypeptide;
(d) amino acids 20-128 of SEQ ID NO: 74 wherein the carboxy-terminus is fused to an immunoglobulin kappa constant region polypeptide;
(e) amino acids 20-137 of SEQ ID NO: 4 wherein the carboxy-terminus is fused to an immunoglobulin gamma-1 constant region polypeptide;
(f) amino acids 20-140 of SEQ ID NO: 27 wherein the carboxy-terminus is fused to an immunoglobulin gamma-1 constant region polypeptide;
(g) amino acids 20-137 of SEQ ID NO: 45 wherein the carboxy-terminus is fused to an immunoglobulin gamma-1 constant region polypeptide;
(h) amino acids 20-137 of SEQ ID NO: 112 wherein the carboxy-terminus is fused to an immunoglobulin gamma-1 constant region polypeptide;
(i) amino acids 20-128 of SEQ ID NO: 76 wherein the carboxy-terminus is fused to an immunoglobulin kappa constant region polypeptide; and
(j) amino acids 20-128 of SEQ ID NO: 78 wherein the carboxy-terminus is fused to an immunoglobulin kappa constant region polypeptide.

45. The nucleic acid of claim 8 encoding a polypeptide comprising amino acids 1-128 of SEQ ID NO: 78 wherein the carboxy-terminus is fused to an immunoglobulin kappa constant region polypeptide.

46. The nucleic acid of claim 14 encoding a polypeptide comprising amino acids 1-137 of SEQ ID NO: 45 wherein the carboxy-terminus is fused to an immunoglobulin gamma-1 constant region polypeptide.

* * * * *

UNITED STATES PATENT AND TRADEMARK OFFICE
CERTIFICATE OF CORRECTION

| | |
|---|---|
| PATENT NO. | : 7,667,021 B2 |
| APPLICATION NO. | : 11/598618 |
| DATED | : February 23, 2010 |
| INVENTOR(S) | : Wang et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 315 days.

Signed and Sealed this

Seventh Day of December, 2010

David J. Kappos
*Director of the United States Patent and Trademark Office*